United States Patent
Strother et al.

(10) Patent No.: US 9,724,526 B2
(45) Date of Patent: Aug. 8, 2017

(54) IMPLANTABLE PULSE GENERATOR SYSTEMS AND METHODS FOR OPERATING THE SAME

(71) Applicant: MEDTRONIC URINARY SOLUTIONS, INC., Minneapolis, MN (US)

(72) Inventors: Robert B. Strother, Cleveland, OH (US); Geoffrey B. Thrope, Cleveland, OH (US); Danny R. Pack, Avon Lake, OH (US)

(73) Assignee: Medtronic Urinary Solutions, Inc., Minneapolis, MN (US)

( * ) Notice: Subject to any disclaimer, the term of this patent is extended or adjusted under 35 U.S.C. 154(b) by 0 days.

(21) Appl. No.: 15/063,073

(22) Filed: Mar. 7, 2016

(65) Prior Publication Data
US 2016/0287884 A1 Oct. 6, 2016

Related U.S. Application Data

(63) Continuation of application No. 11/517,213, filed on Sep. 7, 2006, now Pat. No. 9,308,382, which is a
(Continued)

(51) Int. Cl.
*A61N 1/378* (2006.01)
*A61N 1/36* (2006.01)
(Continued)

(52) U.S. Cl.
CPC ......... *A61N 1/3787* (2013.01); *A61N 1/0551* (2013.01); *A61N 1/3605* (2013.01);
(Continued)

(58) Field of Classification Search
CPC .. A61N 1/3787; A61N 1/37252; A61N 1/375; A61N 1/3758
See application file for complete search history.

(56) References Cited

U.S. PATENT DOCUMENTS

| | | |
|---|---|---|
| 3,421,511 A | 1/1969 | Schwartz et al. |
| 3,654,933 A | 4/1972 | Hagfors |
| | (Continued) | |

FOREIGN PATENT DOCUMENTS

| | | |
|---|---|---|
| CA | 2121219 | 10/1995 |
| WO | WO 0019939 | 4/2000 |
| | (Continued) | |

OTHER PUBLICATIONS

2004 Advanced Bionics Corporation Patient System Handbook, Apr. 27, 2004.
(Continued)

*Primary Examiner* — Tammie K Heller
(74) *Attorney, Agent, or Firm* — Shumaker & Sieffert, P.A.

(57) ABSTRACT

Improved assemblies, systems, and methods provide a stimulation system for prosthetic or therapeutic stimulation of muscles, nerves, or central nervous system tissue, or any combination. The stimulation system includes an implantable pulse generator and a lead sized and configured to be implanted subcutaneously in a tissue region. An external controller includes circuitry adapted for wireless telemetry and a charging coil for generating the radio frequency magnetic field to transcutaneously recharge a rechargeable battery in the pulse generator. Using wireless telemetry, the pulse generator is adapted to transmit status information back to the external controller to allow the external controller to automatically adjust up or down the magnitude of the radio frequency magnetic field and/or to instruct a user to reposition the charging coil, the status information adapted to allow optimal recharging of the pulse generator rechargeable battery.

11 Claims, 24 Drawing Sheets

Related U.S. Application Data continuation-in-part of application No. 11/149,654, filed on Jun. 10, 2005, now Pat. No. 7,565,198, and a continuation-in-part of application No. 11/150,535, filed on Jun. 10, 2005, now Pat. No. 7,813,809, and a continuation-in-part of application No. 11/150,418, filed on Jun. 10, 2005, now Pat. No. 7,239,918.

(60) Provisional application No. 60/801,003, filed on May 17, 2006, provisional application No. 60/680,598, filed on May 13, 2005, provisional application No. 60/599,193, filed on Aug. 5, 2004, provisional application No. 60/578,742, filed on Jun. 10, 2004.

(51) Int. Cl.
*A61N 1/372* (2006.01)
*A61N 1/375* (2006.01)
*A61N 1/05* (2006.01)

(52) U.S. Cl.
CPC ..... *A61N 1/36007* (2013.01); *A61N 1/36071* (2013.01); *A61N 1/375* (2013.01); *A61N 1/3754* (2013.01); *A61N 1/3758* (2013.01); *A61N 1/37229* (2013.01); *A61N 1/37252* (2013.01); *A61N 1/05* (2013.01)

(56) References Cited

U.S. PATENT DOCUMENTS

| | | |
|---|---|---|
| 3,727,616 A | 4/1973 | Lenzkes |
| 3,774,618 A | 11/1973 | Avery |
| 3,870,051 A | 3/1975 | Brindley |
| 3,902,501 A | 9/1975 | Citron et al. |
| 3,926,198 A | 12/1975 | Kolenik |
| 3,939,841 A | 2/1976 | Dohring et al. |
| 3,939,843 A | 2/1976 | Smyth |
| 3,941,136 A | 3/1976 | Bucalo |
| 3,943,932 A | 3/1976 | Woo |
| 3,943,938 A | 3/1976 | Wexler |
| 4,197,850 A | 4/1980 | Schulman et al. |
| 4,232,679 A | 11/1980 | Schulman |
| 4,254,775 A | 3/1981 | Langer |
| 4,257,423 A | 3/1981 | McDonald |
| 4,262,678 A | 4/1981 | Stokes |
| 4,398,545 A | 8/1983 | Wilson |
| 4,406,288 A | 9/1983 | Horwinski et al. |
| 4,407,303 A | 10/1983 | Akerstrom |
| 4,512,351 A | 4/1985 | Pohndorf |
| 4,519,404 A | 5/1985 | Fleischhacker |
| 4,569,351 A | 2/1986 | Tang |
| 4,573,481 A | 3/1986 | Bullara |
| 4,585,005 A | 4/1986 | Lue et al. |
| 4,585,013 A | 4/1986 | Harris |
| 4,590,689 A | 5/1986 | Rosenberg |
| 4,590,946 A | 5/1986 | Loeb |
| 4,592,360 A | 6/1986 | Lesnick |
| 4,602,624 A | 7/1986 | Naples et al. |
| 4,607,639 A | 8/1986 | Tanagho et al. |
| 4,628,942 A | 12/1986 | Sweeney et al. |
| 4,649,936 A | 3/1987 | Ungar et al. |
| 4,658,515 A | 4/1987 | Oatman |
| 4,703,755 A | 11/1987 | Tanagho et al. |
| 4,716,888 A | 1/1988 | Wesner |
| 4,721,118 A | 1/1988 | Harris |
| 4,739,764 A | 4/1988 | Lue et al. |
| 4,741,341 A | 5/1988 | Marach |
| 4,750,499 A | 6/1988 | Hoffer |
| 4,771,779 A | 9/1988 | Tanagho et al. |
| 4,835,372 A | 5/1989 | Gombrich |
| 4,920,979 A | 5/1990 | Bullara |
| 4,926,875 A | 5/1990 | Rabinovitz et al. |
| 4,934,368 A | 6/1990 | Lynch |
| 4,940,065 A | 7/1990 | Tanagho et al. |
| 4,989,617 A | 2/1991 | Memberg et al. |
| 5,095,905 A | 3/1992 | Klepinski |
| 5,113,869 A | 5/1992 | Nappholz et al. |
| 5,154,172 A | 10/1992 | Terry, Jr. et al. |
| 5,215,086 A | 6/1993 | Terry, Jr. et al. |
| 5,222,494 A | 6/1993 | Baker, Jr. |
| D337,820 S | 7/1993 | Hooper et al. |
| 5,235,980 A | 8/1993 | Varrichio et al. |
| 5,257,634 A | 11/1993 | Kroll |
| 5,265,608 A | 11/1993 | Lee et al. |
| 5,282,845 A | 2/1994 | Bush et al. |
| 5,289,821 A | 3/1994 | Swartz |
| 5,300,107 A | 4/1994 | Stokes et al. |
| 5,314,453 A * | 5/1994 | Jeutter ............... A61N 1/3787 607/60 |
| 5,324,322 A | 6/1994 | Grill, Jr. et al. |
| 5,330,515 A | 7/1994 | Rutecki et al. |
| 5,335,664 A | 8/1994 | Nagashima |
| 5,344,439 A | 9/1994 | Otten |
| 5,369,257 A | 11/1994 | Gibbon |
| 5,370,671 A | 12/1994 | Maurer et al. |
| 5,397,338 A | 3/1995 | Grey et al. |
| 5,400,784 A | 3/1995 | Durand et al. |
| 5,411,537 A | 5/1995 | Munshi et al. |
| 5,449,378 A | 9/1995 | Schouenborg |
| 5,454,840 A | 10/1995 | Krakovsky et al. |
| 5,461,256 A | 10/1995 | Yamada et al. |
| 5,476,500 A | 12/1995 | Fain et al. |
| 5,480,416 A | 1/1996 | Garcia et al. |
| 5,487,756 A | 1/1996 | Kallesoe et al. |
| 5,505,201 A | 4/1996 | Grill, Jr. et al. |
| 5,531,778 A | 7/1996 | Maschino et al. |
| 5,540,730 A | 7/1996 | Terry, Jr. et al. |
| 5,562,717 A | 10/1996 | Tippey et al. |
| 5,588,960 A | 12/1996 | Edwards et al. |
| 5,607,461 A | 3/1997 | Lathrop |
| 5,634,462 A | 6/1997 | Tyler et al. |
| 5,645,586 A | 7/1997 | Meltzer |
| 5,669,161 A | 9/1997 | Huang |
| 5,683,432 A * | 11/1997 | Goedeke ............ A61N 1/37223 607/31 |
| 5,683,447 A | 11/1997 | Bush et al. |
| 5,690,693 A | 11/1997 | Wang et al. |
| 5,702,431 A | 12/1997 | Wang et al. |
| 5,713,939 A | 2/1998 | Nedungadi et al. |
| 5,716,384 A | 2/1998 | Snell |
| 5,722,482 A | 3/1998 | Buckley |
| 5,722,999 A | 3/1998 | Snell |
| 5,733,322 A | 3/1998 | Starkebaum |
| 5,741,313 A | 4/1998 | Davis et al. |
| 5,741,319 A | 4/1998 | Woloszko et al. |
| 5,752,977 A | 5/1998 | Grevious et al. |
| 5,755,767 A | 5/1998 | Doan et al. |
| 5,759,199 A | 6/1998 | Snell |
| 5,824,027 A | 10/1998 | Hoffer et al. |
| 5,843,141 A | 12/1998 | Bischoff et al. |
| 5,857,968 A | 1/1999 | Benja-Athon |
| 5,861,015 A | 1/1999 | Benja-Athon |
| 5,861,016 A | 1/1999 | Swing |
| 5,899,933 A | 5/1999 | Bhadra et al. |
| 5,919,220 A | 7/1999 | Stieglitz et al. |
| 5,922,015 A | 7/1999 | Schaldach |
| 5,938,596 A | 8/1999 | Woloszko et al. |
| 5,948,006 A | 9/1999 | Mann |
| 5,957,951 A | 9/1999 | Cazaux et al. |
| 5,984,854 A | 11/1999 | Ishikawa et al. |
| 6,004,662 A | 12/1999 | Buckley |
| 6,016,451 A | 1/2000 | Sanchez-Rodarte |
| 6,026,328 A | 2/2000 | Peckham et al. |
| 6,055,456 A | 4/2000 | Gerber |
| 6,055,457 A | 4/2000 | Bonner |
| 6,061,596 A | 5/2000 | Richmond et al. |
| 6,091,995 A | 7/2000 | Ingle et al. |
| 6,125,645 A | 10/2000 | Horn |
| 6,126,611 A | 10/2000 | Bourgeois et al. |
| 6,166,518 A | 12/2000 | Echarri et al. |
| 6,169,925 B1 | 1/2001 | Villaseca et al. |
| 6,181,965 B1 | 1/2001 | Loeb et al. |
| 6,181,973 B1 | 1/2001 | Ceron et al. |
| 6,185,452 B1 | 2/2001 | Schulman et al. |

(56) References Cited

U.S. PATENT DOCUMENTS

| | | |
|---|---|---|
| 6,200,265 B1 | 3/2001 | Walsh et al. |
| 6,208,894 B1 | 3/2001 | Schulman et al. |
| 6,212,431 B1 | 4/2001 | Hahn et al. |
| 6,216,038 B1 | 4/2001 | Hartlaub et al. |
| 6,240,316 B1 | 5/2001 | Richmond et al. |
| 6,240,317 B1 | 5/2001 | Villaseca et al. |
| 6,257,906 B1 | 7/2001 | Price et al. |
| 6,266,557 B1 | 7/2001 | Roe et al. |
| 6,275,737 B1 | 8/2001 | Mann |
| 6,292,703 B1 | 9/2001 | Meier et al. |
| 6,308,101 B1 | 10/2001 | Faltys et al. |
| 6,308,105 B1 | 10/2001 | Duysens et al. |
| 6,319,208 B1 | 11/2001 | Abita et al. |
| 6,319,599 B1 | 11/2001 | Buckley |
| 6,321,124 B1 | 11/2001 | Cigaina |
| 6,338,347 B1 | 1/2002 | Chung |
| 6,345,202 B2 | 2/2002 | Richmond et al. |
| 6,360,750 B1 | 3/2002 | Gerber et al. |
| 6,370,433 B1 | 4/2002 | Hartlaub et al. |
| 6,381,496 B1 | 4/2002 | Meadows et al. |
| 6,409,675 B1 | 6/2002 | Turcott |
| 6,432,037 B1 | 8/2002 | Eini et al. |
| 6,445,955 B1 | 9/2002 | Michelson et al. |
| 6,449,512 B1 | 9/2002 | Boveja et al. |
| 6,450,172 B1 | 9/2002 | Hartlaub et al. |
| 6,453,198 B1 | 9/2002 | Torgerson et al. |
| 6,456,866 B1 | 9/2002 | Tyler et al. |
| 6,464,672 B1 | 10/2002 | Buckley |
| 6,482,154 B1 | 11/2002 | Haubrich et al. |
| 6,493,587 B1 | 12/2002 | Eckmiller et al. |
| 6,493,881 B1 | 12/2002 | Picotte |
| 6,505,074 B2 | 1/2003 | Boveja et al. |
| 6,505,077 B1 | 1/2003 | Kast et al. |
| 6,510,347 B2 | 1/2003 | Borkan |
| 6,516,227 B1 * | 2/2003 | Meadows ............ A61N 1/0553 607/117 |
| 6,525,512 B2 | 2/2003 | Wuzik et al. |
| 6,539,253 B2 | 3/2003 | Thompson et al. |
| 6,542,776 B1 | 4/2003 | Gordon et al. |
| 6,553,263 B1 | 4/2003 | Meadows et al. |
| 6,567,703 B1 | 5/2003 | Thompson et al. |
| 6,574,510 B2 | 6/2003 | Von Arx et al. |
| 6,580,947 B1 | 6/2003 | Thompson |
| 6,591,137 B1 | 7/2003 | Fischell et al. |
| 6,597,954 B1 | 7/2003 | Pless et al. |
| 6,600,956 B2 | 7/2003 | Maschino et al. |
| 6,607,500 B2 | 8/2003 | DaSilva et al. |
| 6,613,953 B1 | 9/2003 | Altura |
| 6,622,037 B2 | 9/2003 | Kasano |
| 6,622,048 B1 | 9/2003 | Mann et al. |
| 6,641,533 B2 | 11/2003 | Causey, III et al. |
| 6,643,552 B1 | 11/2003 | Edell et al. |
| 6,650,943 B1 | 11/2003 | Whitehurst et al. |
| 6,652,449 B1 | 11/2003 | Gross et al. |
| 6,658,300 B2 | 12/2003 | Govari et al. |
| 6,660,265 B1 | 12/2003 | Chen |
| 6,672,895 B2 | 1/2004 | Scheiner |
| 6,684,109 B1 | 1/2004 | Osypka |
| 6,687,543 B1 | 2/2004 | Isaac |
| 6,701,188 B2 | 3/2004 | Stroebel et al. |
| 6,721,602 B2 | 4/2004 | Engmark et al. |
| 6,735,474 B1 | 5/2004 | Loeb et al. |
| 6,735,475 B1 | 5/2004 | Whitehurst et al. |
| 6,754,538 B2 | 6/2004 | Linberg |
| 6,775,715 B2 | 8/2004 | Spitaels et al. |
| 6,804,558 B2 | 10/2004 | Haller et al. |
| 6,836,684 B1 | 12/2004 | Rijkhoff et al. |
| 6,836,685 B1 | 12/2004 | Fitz |
| 6,845,271 B2 | 1/2005 | Fang et al. |
| 6,850,803 B1 | 2/2005 | Jimenez et al. |
| 6,855,410 B2 | 2/2005 | Buckley |
| 6,856,506 B2 | 2/2005 | Doherty |
| 6,859,364 B2 | 2/2005 | Yuasa et al. |
| 6,862,480 B2 | 3/2005 | Cohen et al. |
| 6,868,288 B2 | 3/2005 | Thompson |
| 6,891,353 B2 | 5/2005 | Tsukamoto |
| 6,893,395 B1 | 5/2005 | Kraus et al. |
| 6,895,280 B2 | 5/2005 | Meadows et al. |
| 6,904,324 B2 | 6/2005 | Bishay |
| 6,907,293 B2 | 6/2005 | Grill et al. |
| 6,907,295 B2 | 6/2005 | Gross et al. |
| 6,920,359 B2 | 7/2005 | Meadows et al. |
| 6,925,330 B2 | 8/2005 | Kleine |
| 6,928,320 B2 | 8/2005 | King |
| 6,931,284 B2 | 8/2005 | Engmark et al. |
| 6,937,894 B1 | 8/2005 | Isaac et al. |
| 6,941,171 B2 | 9/2005 | Mann et al. |
| 6,963,780 B2 | 11/2005 | Ruben et al. |
| 6,974,411 B2 | 12/2005 | Belson |
| 6,985,773 B2 | 1/2006 | Von Arx et al. |
| 6,990,376 B2 | 1/2006 | Tanagho |
| 6,993,393 B2 | 1/2006 | Von Arx et al. |
| 6,999,819 B2 | 2/2006 | Swoyer et al. |
| 7,031,768 B2 | 4/2006 | Anderson et al. |
| 7,047,078 B2 | 5/2006 | Boggs, II et al. |
| 7,078,359 B2 | 7/2006 | Stepanian et al. |
| 7,101,607 B2 | 9/2006 | Mollendorf |
| 7,103,923 B2 | 9/2006 | Picotte |
| 7,118,801 B2 | 10/2006 | Ristic-Lehmann |
| 7,136,695 B2 | 11/2006 | Pless |
| 7,167,756 B1 | 1/2007 | Torgerson et al. |
| 7,177,690 B2 | 2/2007 | Woods et al. |
| 7,177,698 B2 | 2/2007 | Klosterman |
| 7,187,968 B2 | 3/2007 | Wolf |
| 7,187,983 B2 | 3/2007 | Dahlberg et al. |
| 7,191,012 B2 | 3/2007 | Boveja |
| 7,198,603 B2 | 4/2007 | Penner et al. |
| 7,225,032 B2 | 5/2007 | Schmeling et al. |
| 7,239,918 B2 | 7/2007 | Strother et al. |
| 7,254,448 B2 | 8/2007 | Almendinger et al. |
| 7,269,457 B2 | 9/2007 | Shafer et al. |
| 7,280,872 B1 | 10/2007 | Mosesov et al. |
| 7,283,867 B2 | 10/2007 | Strother et al. |
| 7,317,947 B2 | 1/2008 | Wahlstrand |
| 7,328,068 B2 | 2/2008 | Spinelli et al. |
| 7,342,793 B2 | 3/2008 | Ristic-Lehmann |
| 7,343,202 B2 | 3/2008 | Mrva et al. |
| 7,369,897 B2 | 5/2008 | Boveja |
| 7,376,467 B2 | 5/2008 | Thrope |
| 7,437,193 B2 | 10/2008 | Parramon et al. |
| 7,443,057 B2 | 10/2008 | Nunally |
| 7,475,245 B1 | 1/2009 | Healy et al. |
| 7,499,758 B2 | 3/2009 | Cates |
| 7,565,198 B2 | 7/2009 | Bennett |
| 7,813,809 B2 | 10/2010 | Strother et al. |
| 8,165,692 B2 | 4/2012 | Strother et al. |
| 8,195,304 B2 | 6/2012 | Strother et al. |
| 9,205,255 B2 | 12/2015 | Strother et al. |
| 9,308,382 B2 | 4/2016 | Strother et al. |
| 9,480,846 B2 | 11/2016 | Strother et al. |
| 2001/0022719 A1 | 9/2001 | Armitage |
| 2002/0007198 A1 | 1/2002 | Haupert et al. |
| 2002/0019652 A1 | 2/2002 | DaSalva et al. |
| 2002/0026224 A1 | 2/2002 | Thompson et al. |
| 2002/0055761 A1 | 5/2002 | Mann et al. |
| 2002/0055779 A1 | 5/2002 | Andrews |
| 2002/0068956 A1 | 6/2002 | Bloemer et al. |
| 2002/0077572 A1 | 6/2002 | Fang et al. |
| 2002/0077676 A1 | 6/2002 | Schroeppel et al. |
| 2002/0109621 A1 | 8/2002 | Khair et al. |
| 2002/0123672 A1 | 9/2002 | Christophersom et al. |
| 2002/0161403 A1 | 10/2002 | Meadows et al. |
| 2002/0164474 A1 | 11/2002 | Buckley |
| 2003/0018365 A1 | 1/2003 | Loeb |
| 2003/0065368 A1 | 4/2003 | VanDerHoeven |
| 2003/0074030 A1 | 4/2003 | Leyde et al. |
| 2003/0074033 A1 | 4/2003 | Pless et al. |
| 2003/0078633 A1 | 4/2003 | Firlik et al. |
| 2003/0088295 A1 | 5/2003 | Cox et al. |
| 2003/0100930 A1 | 5/2003 | Cohen et al. |
| 2003/0114897 A1 | 6/2003 | Von Arx et al. |
| 2003/0114898 A1 | 6/2003 | Von Arx et al. |
| 2003/0114905 A1 | 6/2003 | Kuzma |
| 2003/0120259 A1 | 6/2003 | Mickley |

(56) References Cited

U.S. PATENT DOCUMENTS

| | | |
|---|---|---|
| 2003/0139783 A1 | 7/2003 | Kilgore et al. |
| 2003/0149459 A1 | 8/2003 | Von Arx et al. |
| 2003/0220673 A1 | 11/2003 | Snell |
| 2004/0030360 A1 | 2/2004 | Eini et al. |
| 2004/0059392 A1 | 3/2004 | Parramon et al. |
| 2004/0082977 A1 | 4/2004 | Engmark et al. |
| 2004/0088024 A1 | 5/2004 | Firlik et al. |
| 2004/0093093 A1 | 5/2004 | Andrews |
| 2004/0098068 A1 | 5/2004 | Carbunaru et al. |
| 2004/0147886 A1 | 7/2004 | Bonni |
| 2004/0150963 A1 | 8/2004 | Holmberg |
| 2004/0204744 A1 | 10/2004 | Penner et al. |
| 2004/0209061 A1 | 10/2004 | Farnworth |
| 2004/0260372 A1 | 12/2004 | Canfield et al. |
| 2005/0004619 A1 | 1/2005 | Wahlstrand et al. |
| 2005/0021108 A1 | 1/2005 | Klosterman et al. |
| 2005/0038491 A1 | 2/2005 | Haack |
| 2005/0055063 A1 | 3/2005 | Loeb et al. |
| 2005/0080463 A1 | 4/2005 | Stahman |
| 2005/0107841 A1 | 5/2005 | Meadows et al. |
| 2005/0131493 A1 | 6/2005 | Boveja et al. |
| 2005/0143787 A1 | 6/2005 | Boveja et al. |
| 2005/0149146 A1 | 7/2005 | Boveja et al. |
| 2005/0175799 A1 | 8/2005 | Farnworth |
| 2005/0192526 A1 | 9/2005 | Biggs et al. |
| 2005/0277844 A1 | 12/2005 | Strother et al. |
| 2005/0277999 A1 | 12/2005 | Strother et al. |
| 2005/0278000 A1 | 12/2005 | Strother et al. |
| 2006/0004421 A1 | 1/2006 | Bennett et al. |
| 2006/0025829 A1 | 2/2006 | Armstrong et al. |
| 2006/0033720 A1 | 2/2006 | Robbins et al. |
| 2006/0035054 A1 | 2/2006 | Stepanian et al. |
| 2006/0085039 A1 | 4/2006 | Hastings et al. |
| 2006/0100673 A1 | 5/2006 | Koinzer |
| 2006/0113955 A1 | 6/2006 | Nunally et al. |
| 2006/0122660 A1 | 6/2006 | Boveja et al. |
| 2006/0173507 A1 | 8/2006 | Mrva et al. |
| 2006/0184208 A1 | 8/2006 | Boggs et al. |
| 2006/0271112 A1 | 11/2006 | Martinson et al. |
| 2007/0060967 A1 | 3/2007 | Strother et al. |
| 2007/0060980 A1 | 3/2007 | Strother et al. |
| 2007/0100411 A1 | 5/2007 | Bonde |
| 2007/0123952 A1 | 5/2007 | Strother |
| 2007/0239224 A1 | 10/2007 | Bennett et al. |
| 2008/0071322 A1 | 3/2008 | Mrva et al. |
| 2008/0097564 A1 | 4/2008 | Lathrop |
| 2008/0132969 A1 | 6/2008 | Bennett et al. |
| 2011/0004269 A1 | 1/2011 | Strother et al. |

FOREIGN PATENT DOCUMENTS

| | | |
|---|---|---|
| WO | WO 0183029 | 4/2000 |
| WO | WO 03092227 | 4/2003 |
| WO | WO 2006055547 | 5/2006 |
| WO | WO 2009058984 | 5/2009 |

OTHER PUBLICATIONS

2004 Advanced Bionics Corporation Physician Implant Manual.
2004 Advanced Bionics Corporation Summary of Safety and Effectiveness, pp. 1-18.
2005 Advanced Neuromodulation systems, Inc.; ANS Medical—Determining Chronic Pain Causes and Treatments Website: http://www.ans-medical.com/medicalprofessional/physician/rechargeablejpgsystems.cfm.
Nissenkorn, et al., 2005 Biocontrol Medical Article: "Lower Urinary Tract," Mar. 12, 2005, pp. 1253-1258.
2005 Cyberonics VNS Therapy website: http://www.vnstherapy.com/epilspsy/hcp/forsurgeons/implantedcomponents.aspx.
A Breakthrough in Advanced Materials, Aspen Aerogels, Inc. (1 pg), retrieved on Nov. 4, 2009 from, www.aerogels.com, 2003.
Aug. 2002 Physician's Manual: Cyberonics Models 100 and 101 NeuroCybernetic Prosthesis System, NCP Pulse Generator, pp. 1-92.
Bemelmans, et al., "Neuromodulation by Implant for Treating Lower Urinary Tract Symptoms and Dysfunction," Eur. Urol. Aug. 1999; 36(2): 81-91.
Bower, et al., "A Urodynamic Study of Surface Neuromodulation versus Sham in Detrusor Instability and Sensory Urgency", J. Urology; Dec. 1998; 160: 2133-2136.
Brindley, et al., "Sacral Anterior Root Stimulators for Bladder Control in Paraplegia", Paraplegia, Dec. 20, 1982; 20(6):365-381.
Bushan Kuma Purushotharnan, "Development of Batteries for Implantable Applications," Case Western Reserve University, Department of Chemical Engineering, Aug. 2006 (272 pgs.).
Caldwell, (1971) Multielectrode Electrical Stimulation of Nerve, in Development of Orthotic Systems using Functional Electrical Stimulation and Myoelectric Control, Final Report Project #19-P-58391-F-01, University of Lublinana, Faculty of Electrical Engineering, Lubjiana, Yugoslavia.
Corbett, http://crisp.cit.nih.gov/ Abstract, High-Density Liquid Crystal Polymer Cochlear Electrodes, downloaded Sep. 18, 2006.
Craggs, et al., "Neuromodulation of the Lower Urinary Tract," Experimental Physiology, 84, 149-160; Jan. 1999.
Craggs, et al., "Aberrant reflexes and function of the pelvic organs following spinal cord injury in man", Autonomic Neuroscience: Basic & Clinical, 126-127; May 2006, 355-370.
Crampon et al., "Nerve Cuff Electrode with Shape Memory Alloy Armature: Design and Fabrication", Bio-Medical Materials and Engineering 12, Jan. 2002, 397-410.
Crampon et al., "New Easy to Install Nerve Cuff Electrode Using Shape Memory Alloy Armature", Artificial Organs, 23(5):392-395, May 1999.
Dalmose, et al., "Conditional Stimulation of the Dorsal Penile/Clitoral Nerve", Neurourol Urodyn; Feb. 2003; 22(2):130-137.
Datasheet for Microchip MCP73841/2/3/4 Lithium-ion/ Lithium-Polymer Charge Management Controllers. 2004, 24 pp.
Edell, PhD, Boston Healthcare Research Device, Feb. 15, 2006, 3 pp.
Fossberg, et al. "Maximal Electrical Stimulation in the Treatment of Unstable Detrusor and Urge Incontinence", Eur Urol 1990; 18:120-123.
Grill, et al., "Emerging clinical applications of electrical stimulation: opportunities for restoration of function", Journal of Rehabilitation Research and Development, vol. 38, No. 6, Nov./Dec. 2001.
Grill, et al., Quantification of recruitment properties of multiple contact cuff electrodes, IEEE Transactions on Rehabilitation Engineering 4(2):49-62; Jun. 1996.
Grill, "Selective Activation of the Nervous System for Motor System Neural Prosthesis" in Intelligent Systems and Technologies in Rehabilitation Engineering, H-N.L. Teodorescu, L. C. Jain, Eds., CRC Press, May 2001, pp. 211-241.
Gustafson, K., et al. "A Urethral Afferent Mediated Excitatory Bladder Reflex Exists in Humans", Neurosci Letters; Apr. 2004: 360(1-2):9-12.
Gustafson, et al., "A Catheter Based Method to Activate Urethral Sensory Nerve Fibers", J Urol; Jul. 2003: 170(1):126-129.
Jezernik, "Electrical Stimulation for the Treatment of Bladder Dysfunction: Current Status and Future Possibilities", Neurol. Res. Jul. 2002: 24:413-30.
Jezernik, et al., "Detection and inhibition of hyper-reflexia-like bladder contractions in the cat by sacral nerve root recording and electrical stimulation," Neurourology and Urodynamics, 20(2), 215-230 (2001).
Jiang, et al., "Prolonged Increase in Micturition Threshold Volume by Anogenital Afferent Stimulation in the Rat", Br J. Urol. Sep. 1998: 82(3):398-403.
Jiang, et al., "Prolonged enhancement of the micturition reflex in the cat by repetitive stimulation of bladder afferents," Journal of Physiology, 517.2 599-605, Jun. 1999.
Juenemann, et al., Clinical Significance of Sacral and Pudendal Nerve Anatomy: J. Urol. Jan. 1988; 139(1):74-80.
Lee, et al., "Self-Controlled dorsal penile nerve stimulation to inhibit bladder hyperreflexia in incomplete spinal injury: A case report," Arch Phys Med Rehabil., 83, 273-7; Feb. 2002.

(56) References Cited

OTHER PUBLICATIONS

Loeb et al., "Cuff Electrodes for Chronic Stimulation and Recording of Peripheral Nerve Activity", *Journal of Neuroscience Methods*, 64, Jan. 1996, 95-103.
Madersbacher, Urinary Urge and Reflex Incontinence: Urologe A. Jul. 1991: 30(4): 215-222 (Abstract only, article in German).
Mar. 2002 Physician's Manual: Cyberonics Model 201 NeuroCybernetic Presthesis (NCP) Programming Wand, pp. 1-18.
Mazieres, et al., "Bladder Parasympathetic Response to Electrical Stimulation of Urethral Afferents in the Cat", Neurol Urodynam 1997; 16:471-472.
Mazieres, et al., "The C Fibre Reflex of the Cat Urinary Bladder", J. Physiol Dec. 1998; 513 (Pt 2):531-541.
McNeal, D.R., Dec. 1973-Nov. 1974; Selective Stimulation, in Annual Reports of Progress, Rehabilitation Engineering Center, Ranchio Los Amigos Hospital, Downey, CA, pp. 24-25.
McNeal, D.R., May 1985; Selective activation of muscles using peripheral nerve electrodes. Med. and Biol. Eng. and Comp., 23:249-253.
Modern Plastics Worldwide, Notables: 10 Waves of the Future by Modern Plastics Editorial Staff, Sample Molding in Progress, Sep. 1, 2005.
Nakamura, et al., "Bladder Inhibition by Penile Electrical Stimulation", Br J Urol Aug. 1984: 56:413-415.
Naples, et al., "A Spiral Nerve Cuff Electrode for Peripheral Nerve Stimulation", *IEEE Transactions on Biomedical Engineering*, vol. 35, No. 11, Nov. 1988.
NeuroControl Corp., The NeuroControl StiM System, "World's First Miniturized Multi-Channel Programmable Neuromuscular Stimulator" brochure, Jan. 2000.
Nov. 21, 2001 Advanced Nueromodulation Systems, Inc. (ANS) Summary of Safety and Effectiveness Data, 17 pp.
Oct. 2001 Advanced Neuromodulation Systems, Inc., ANS Genesis Neurostimulation System Programmer User's Guide.
Oliver, et al., "Measuring the Sensations of Urge and Bladder Filling During Cystometry in Urge Incontinence and the Effects of Neuromodulation", Neurourol Urodyn Jan. 2003: 22:7-16.
Previnaire, "Short-Term Effect of Pudendal Nerve Electrical Stimulation on Detrusor Hyperreflexia in Spinal Cord Injury Patients: Importance of Current Strength", Paraplegia Feb. 1996: 34:95-99.
Rijkhoff, et al., "Urinary Bladder Control by Electrical Stimulation: Review of Electrical Stimulation Techniques in Spinal Cord Injury", Neurourol Urodyn, Feb. 1997; 16(1):39-53.
Riley, PhD, www.flipchips.com, Advanced Packaging—Water Level Hermetic Cavity Packaging, originally published in Advanced Packaging Magazine, May 2004.
Riley, PhD, www.flipchips.com, Tutorial 31—Jun. 2003, A survey of Water Level Hermetic Cavity Chip Scale Packages for RF Applications.
Romero et al., "Neural Morphological Effects of Long-Term Implantation of the Self-Sizing Spiral Cuff Nerve Electrode", *Medical & Biological Engineering & Computing*, Jan. 2001, vol. 39, pp. 90-100.
Sahin et al., "Spiral Nerve Cuff Electrode for Recordings of Respiratory Output", *The Spiral Nerve Cuff Electrode*, Jul. 1997 American Physiological Society, pp. 317-322.
Schmidt, R.A., "Applications of Neurostimulation in Urology", Jul. 1988; 7:585-92.
Spinelli, et al., "A New Minimally Invasive Procedure for Pudendal Nerve Stimulation to Treat Neurogenic Bladder: Description of the Method and Preliminary Data", Neurourol and Urodyn. Jun. 2005: 24:305-309.

Starbuck, et al., (1966) "An implantable electrodes system for nerve stimulation," Proc $19^{th}$ Ann. Conf. on Eng. in Med. and Biol. 8:38
Starbuck, "Myo-electric control of paralyzed muscles," IEEE Transactions on Biomedical Engineering 12(3):169-172, Jul.-Oct. 1965.
Sundin, et al., "Detrusor inhibition induced from mechanical stimulation of the anal region and from electrical stimulation of pudendal nerve afferents," Investigative Urology, 5, 374-8; Mar. 1974.
Sweeney, et al., "A Nerve Cuff Technique for Selective Excitation of Peripheral Nerve Trunk Regions", *IEEE Transactions on Biomedical Engineering*, vol. 37, No. 7, Jul. 1990.
Talaat, M., "Afferent Impulses in the Nerves Supplying the Urinary Bladder", Journal of Physiology Jul. 1937: 89-1-13.
Tanagho, et al. "Electrical Stimulation in the Clinical Management of the Neurogenic Bladder", J. Urol. Dec. 1988; 140:1331-1339.
Tyler, et al., "Chronic Response of the Rat Sciatic Nerve to the Flat Interface Nerve Electrode", *Annals of Biomedical Engineering*, vol. 31, pp. 633-642, Jun. 2003.
Veraart, et al., "Selective control of muscle activation with a multipolar nerve cuff electrode," IEEE Trans. Biomed. Engineering 40:640-653, Jul. 1993.
Vodusek, D.B., et al. "Detrusor Inhibition Induced by Stimulation of Pudendal Nerve Afferents", Neuroul and Urodyn., Jul./Oct. 1986; 5:381-389.
Wheeler, et al., "Bladder inhibition by penile nerve stimulation in spinal cord injury patients", The Journal of Urology, 147(1), 100-3; Jan. 1992.
Wheeler, et al., "Management of Incontinent SCI patients with Penile Stimulation; Preliminary Results," J. Am. Paraplegia Soc. Apr. 1994: 17(2):55-9.
www.devicelink.com, MPMN, May 2004, Liquid-Crystal Polymer Meets the Challenges of RF Power Packaging; The plastic air-cavity packages are hermetically sealed using a proprietary process, Susan Wallace.
www.foster-miller.com, Project Examples, Packaging for Implantable Electronics, Foster-Miller, Inc., Feb. 15, 2006.
www.machinedesign.texterity.com, Vacuum-Formed Films for Fit and Function, High-Performance Films can Replace Injection-Molded Plastics When Space is at a Premium, David Midgley, Welch Fluorocarbon Inc., Dover, NH, Oct. 7, 2004.
Yang, et al., "Peripheral Distribution of the Human Dorsal Nerve of the Penis", J. Urol Jun. 1998; 159(6):1912-6, discussion 1916.
U.S. Appl. No. 11/824,931, filed Jul. 3, 2007, by Robert B. Strothers.
U.S. Appl. No. 11/516,890, filed Sep. 7, 2006, by Strothers et al.
Supplemental European Search Report dated Apr. 21, 2011 for European Application No. 07777090.7 (6 pgs.).
Examination Report from counterpart European Application No. 07777090.7, dated Feb. 9, 2012, 5 pp.
International Search Report and Written Opinion from International Application No. PCT/US08/081762, dated Feb. 2, 2009, 17 pp.
International Preliminary Report on Patentability from International Application No. PCT/US07/014396, dated Jun. 26, 2009, 7 pp.
Reply to Written Opinion dated Nov. 11, 2008 from International Application No. PCT/US07/014396, 13 pp.
Prosecution History from U.S. Appl. No. 11/150,535, dated from Feb. 23, 2007 through Jun. 22, 2010, 163 pp.
Prosecution History from U.S. Appl. No. 11/517,213, dated from Sep. 9, 2009 through Feb. 26, 2016, 314 pp.
Prosecution History from U.S. Appl. No. 11/712,379, dated from Dec. 22, 2008 through Jun. 15, 2016, 185 pp.
Prosecution History from U.S. Appl. No. 15/339,596, dated from Dec. 31, 2016 through Feb. 10, 2017, 49 pp.

* cited by examiner

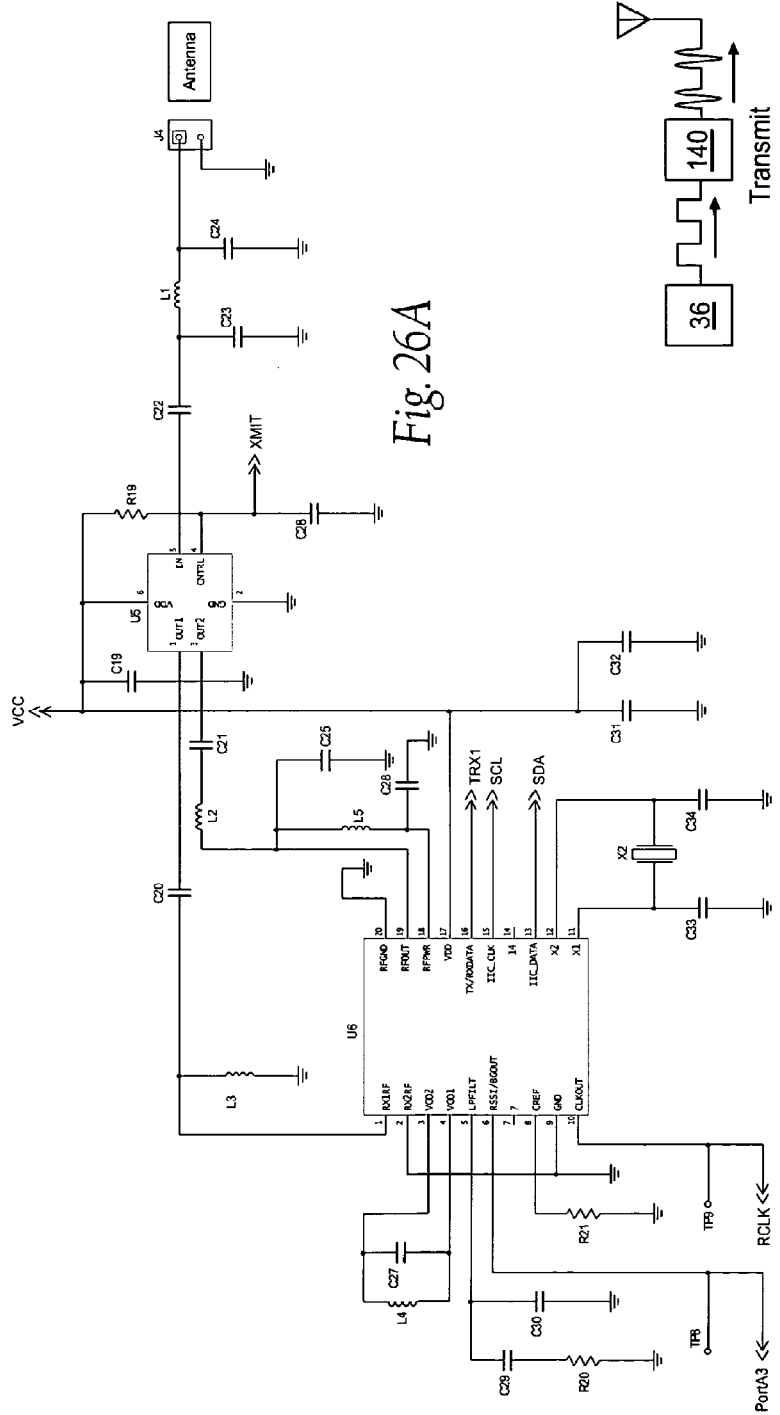
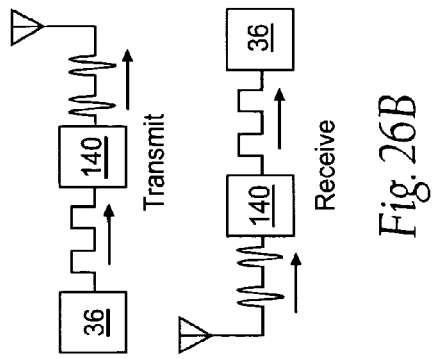
Fig. 26A
Fig. 26B

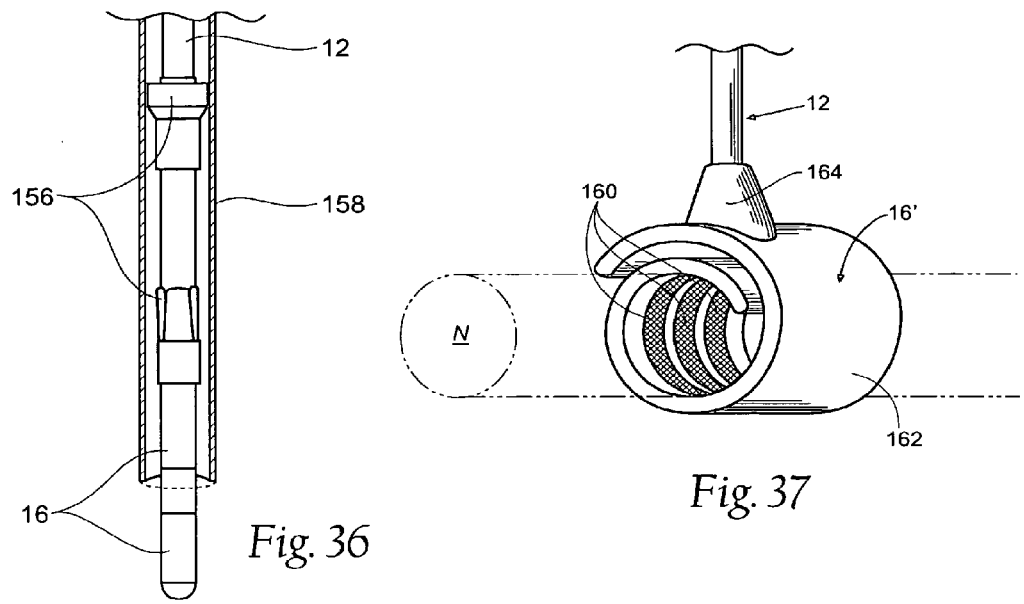
Fig. 36
Fig. 37
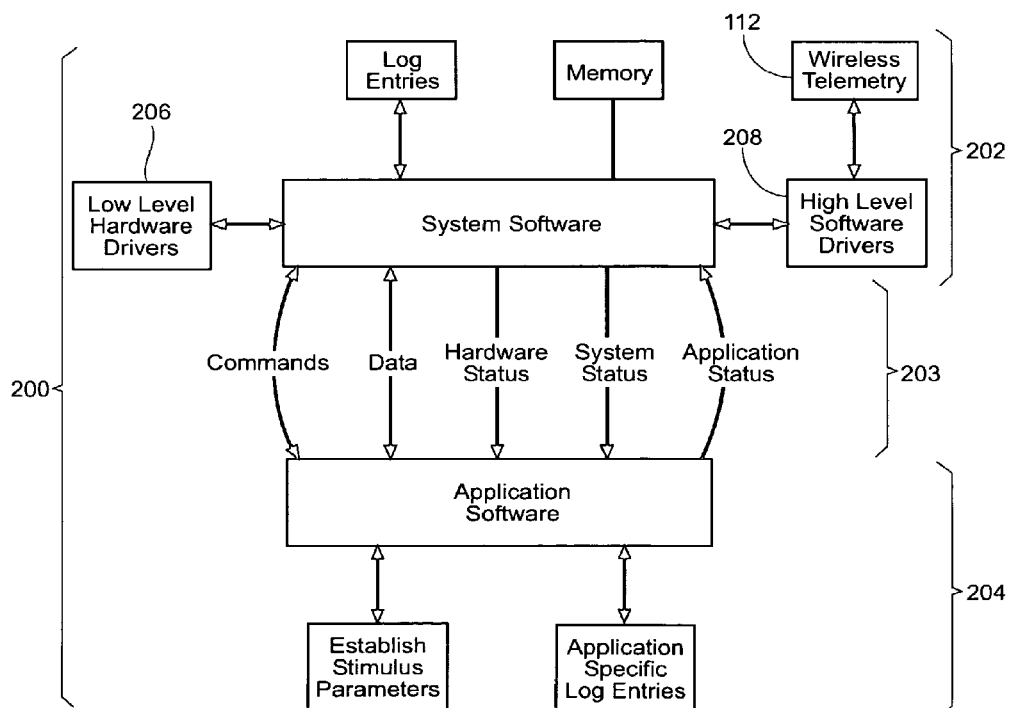
Fig. 38

IMPLANTABLE PULSE GENERATOR SYSTEMS AND METHODS FOR OPERATING THE SAME

RELATED APPLICATIONS

This application is a continuation of U.S. application Ser. No. 11/517,213, filed Sep. 7, 2006, granted as U.S. Pat. No. 9,308,382, which claims the benefit of U.S. Provisional Patent Application Ser. No. 60/801,003, filed 17 May 2006, and entitled "Implantable Pulse Generator for Providing Functional and/or Therapeutic Stimulation of Muscle and/or Nerves and/or Central Nervous System Tissue." The entire content of each of these applications is incorporated herein by reference.

U.S. application Ser. No. 11/517,213 is a continuation-in-part of U.S. patent application Ser. No. 11/149,654, filed 10 Jun. 2005, granted as U.S. Pat. No. 7,565,198, and entitled "Systems and Methods for Bilateral Stimulation of Left and Right Branches of the Dorsal Genital Nerves to Treat Dysfunctions, Such as Urinary Incontinence," which claims the benefit of U.S. Provisional Patent Application Ser. No. 60/578,742, filed Jun. 10, 2004, and entitled "Systems and Methods for Bilateral Stimulation of Left and Right Branches of the Dorsal Genital Nerves to Treat Dysfunctions, Such as Urinary Incontinence." The entire content of each of these applications is incorporated herein by reference.

U.S. application Ser. No. 11/517,213 is also a continuation-in-part of U.S. patent application Ser. No. 11/150,418, filed 10 Jun. 2005, granted as U.S. Pat. No. 7,239,918, and entitled "Implantable Pulse Generator for Providing Functional and/or Therapeutic Stimulation of Muscles and/or Nerves and/or Central Nervous System Tissue," which claims the benefit of U.S. Provisional Patent Application Ser. No. 60/599,193, filed Aug. 5, 2004, and entitled "Implantable Pulse Generator for Providing Functional and/or Therapeutic Stimulation of Muscles and/or Nerves,." The entire content of each of these applications is incorporated herein by reference.

U.S. application Ser. No. 11/517,213 is also a continuation-in-part of U.S. patent application Ser. No. 11/150,535, filed 10 Jun. 2005, granted as U.S. Pat. No. 7,813,809, and entitled "Implantable Pulse Generator for Providing Functional and/or Therapeutic Stimulation of Muscles and/or Nerves and/or Central Nervous System Tissue," which claims the benefit of U.S. Provisional Patent Application Ser. No. 60/680,598, filed May 13, 2005, and entitled "Implantable Pulse Generator for Providing Functional and/or Therapeutic Stimulation of Muscles and/or Nerves and/or Central Nervous System Tissue." The entire content of each of these applications is incorporated herein by reference.

FIELD OF THE INVENTION

The invention relates to systems and methods for providing stimulation of central nervous system tissue, muscles, or nerves, or combinations thereof.

BACKGROUND OF THE INVENTION

Neuromuscular stimulation (the electrical excitation of nerves and/or muscle to directly elicit the contraction of muscles) and neuromodulation stimulation (the electrical excitation of nerves, often afferent nerves, to indirectly affect the stability or performance of a physiological system) and brain stimulation (the stimulation of cerebral or other central nervous system tissue) can provide functional and/or therapeutic outcomes. While existing systems and methods can provide remarkable benefits to individuals requiring neuromuscular or neuromodulation stimulation, many limitations and issues still remain. For example, existing systems often can perform only a single, dedicated stimulation function.

Today there are a wide variety of implantable medical devices that can be used to provide beneficial results in diverse therapeutic and functional restorations indications. For example, implantable pulse generators can provide therapeutic and functional restoration outcomes in the field of urology, such as for the treatment of (i) urinary and fecal incontinence; (ii) micturition/retention; (iii) restoration of sexual function; (iv) defecation/constipation; (v) pelvic floor muscle activity; and/or (vi) pelvic pain. Implantable pulse generators can also be used for deep brain stimulation, compensation for various cardiac dysfunctions, pain management by interfering with or blocking pain signals, vagal nerve stimulation for control of epilepsy, depression, or other mood/psychiatric disorders, the treatment of obstructive sleep apnea, for gastric stimulation to prevent reflux or to reduce appetite or food consumption, and can be used in functional restorations indications such as the restoration of motor control.

There exists both external and implantable devices for providing beneficial results in diverse therapeutic and functional restorations indications. The operation of these devices typically includes the use of an electrode placed either on the external surface of the skin, a vaginal or anal electrode, or a surgically implanted electrode. Although these modalities have shown the ability to provide a neurological stimulation with positive effects, they have received limited acceptance by patients because of their limitations of portability, limitations of treatment regimes, and limitations of ease of use and user control.

Implantable devices have provided an improvement in the portability of neurological stimulation devices, but there remains the need for continued improvement. Implantable stimulators described in the art have additional limitations in that they are challenging to surgically implant because they are relatively large, they require direct skin contact for programming and for turning on and off, and only provide a single dedicated stimulation function. In addition, current implantable stimulators are expensive, owing in part to their limited scope of usage.

These implantable devices are also limited in their ability to provide sufficient power which limits their use in a wide range of stimulation applications, requires surgical replacement of the device when the batteries fail, and limits their acceptance by patients. Rechargeable batteries have been used but are limited by the need to recharge a power supply frequently (e.g., daily), and the inconvenience of special recharge methods.

More recently, small, implantable microstimulators have been introduced that can be injected into soft tissues through a cannula or needle. Although these small implantable stimulation devices have a reduced physical size, their application to a wide range of simulation applications is limited. Their micro size extremely limits their ability to maintain adequate stimulation strength for an extended period without the need for frequent recharging of their internal power supply (battery). Additionally, their very small size limits the tissue volumes through which stimulus currents can flow at a charge density adequate to elicit neural excitation. This, in turn, limits or excludes many applications.

For each of these examples, the medical device (i.e., an implantable pulse generator), is often controlled using microprocessors with resident operating system software (code). This operating system software may be further broken down into subgroups including system software and application software. The system software controls the operation of the medical device while the application software interacts with the system software to instruct the system software on what actions to take to control the medical device based upon the actual application of the medical device (i.e., to control incontinence or the restoration of a specific motor control).

As the diverse therapeutic and functional uses of implantable medical devices increases, and become more complex, system software having a versatile interface is needed to play an increasingly important role. This interface allows the system software to remain generally consistent based upon the particular medical device, and allows the application software to vary greatly depending upon the particular application. As long as the application software is written so it can interact with the interface, and in turn the system software, the particular medical device can be used in a wide variety of applications with only changes to application specific software. This allows a platform device to be manufactured in large, more cost effective quantities, with application specific customization occurring at a later time.

It is time that systems and methods for providing neurological stimulation address not only specific prosthetic or therapeutic objections, but also address the quality of life of the individual requiring the beneficial stimulation. In addition, there remains the need for improved size, operation, and power considerations of implantable medical devices that will improve the quality of life issues for the user.

SUMMARY OF THE INVENTION

The invention provides improved assemblies, systems, and methods for providing prosthetic or therapeutic stimulation of central nervous system tissue, muscles, or nerves, or muscles and nerves.

One aspect of the invention provides an implantable pulse generator system. The system comprises a pulse generator including a housing sized and configured for implantation in subcutaneous tissue, circuitry carried within the housing and adapted for wireless telemetry, a rechargeable battery coupled to the circuitry and carried within the housing, the battery having a voltage, a power receiving coil carried within the housing and coupled to the circuitry, the power receiving coil for transcutaneously receiving an externally generated radio frequency magnetic field to recharge the rechargeable battery, and an external controller including circuitry adapted for wireless telemetry, and a charging coil for generating the radio frequency magnetic field to transcutaneously recharge the rechargeable battery.

Another aspect of the invention provides a pulse generator system where the power receiving coil includes a maximum outside dimension X, and wherein the pulse generator is adapted to be implanted in subcutaneous tissue at an implant depth D, such that the ratio of X/D is between about 0.8 to 1 and about 4 to 1. The outer surface of the housing maintains a two degrees Celsius or less temperature rise during the time period in which the power receiving coil is transcutaneously receiving the externally generated radio frequency magnetic field. In one embodiment, the implant depth D is between about five millimeters and about twenty millimeters. The housing of the implantable pulse generator may be sized to have a thickness of between about 5 mm and 15 mm, a width of between about 30 mm and 60 mm, and a length of between about 45 mm and 60 mm, and the circuitry carried within the housing is operable for generating electrical stimulation pulses and/or sensing myoelectric signals.

During a battery recharge period, and using wireless telemetry, the pulse generator is adapted to transmit status information back to the external controller to allow the external controller to automatically adjust up or down the magnitude of the radio frequency magnetic field and/or to instruct a user to reposition the charging coil, the status information adapted to allow optimal recharging of the pulse generator rechargeable battery. The instruction to the user may be a visual instruction and/or an audio instruction. The adjustment of the magnitude of the radio frequency magnetic field may be an adjustment of up to about 300 percent of the initial magnitude. The status information can include an indication of the battery charge status and an indication of the magnitude of power recovered by the receive coil. The status information can also include a magnitude of the battery voltage and a magnitude of a DC voltage recovered from the radio frequency magnetic field. The radio frequency magnetic field comprises a frequency between about 30 KHz and about 300 KHz.

Another aspect of the invention provides an implantable pulse generator system where the pulse generator is exclusively the wireless telemetry communications slave, with all wireless telemetry communications initiated by the external controller. The wireless telemetry communication between the external controller and the pulse generator operates in the MICS (Medical Implant Communications Service) band at between about 402 MHz to about 405 MHz.

Yet another aspect of the invention provides an implantable pulse generator system where the external controller's charging coil may be coupled via a cable to the external controller. The charging coil comprises an outside diameter in the range of about 40 millimeters to about 70 millimeters, and a thickness as measured perpendicular to the diameter in the range of about three millimeters to about eleven millimeters. The charging coil is adapted to maintain a temperature at or below about 41 degrees Celsius during a charging period.

Yet another aspect of the invention includes an implantable pulse generator system where the rechargeable battery of the implantable pulse generator comprises a capacity of at least 30 mA-hr and recharging of the rechargeable battery is required less than weekly. When the rechargeable battery has only a safety margin charge remaining, it can be recharged in a time period of not more than six hours.

Another aspect of the invention provides an implantable pulse generator system, the system comprising a housing sized and configured for implantation in subcutaneous tissue, circuitry carried within the housing and adapted for wireless telemetry, a rechargeable battery coupled to the circuitry and carried within the housing, a power receiving coil carried within the housing and coupled to the circuitry, the power receiving coil for transcutaneously receiving an externally generated radio frequency magnetic field to recharge the rechargeable battery, and an external controller including circuitry adapted for wireless telemetry, and a charging coil for generating the radio frequency magnetic field to transcutaneously recharge the rechargeable battery.

The pulse generator wireless telemetry circuitry includes a transceiver chip, the transceiver chip adapted to be off about 99 percent or more of the time for efficient power management, and is pulsed on periodically to search for a command from the external controller. The wireless telemetry is configured to have the external controller issue commands to the pulse generator at timed intervals to confirm that the generated radio frequency magnetic field is adequate for recharging the rechargeable battery.

The circuitry within the housing further includes power management circuitry, the power management circuitry comprising at least three operating modes relating to the operation of the pulse generator, the operating modes including pulse generator active, pulse generator dormant, and pulse generator active and charging. The circuitry also includes a microcontroller, the microcontroller adapted to generate a serial data stream, the serial data stream being converted by the pulse generator wireless telemetry circuitry into a pulsing carrier signal during a transmit process, and the pulse generator wireless telemetry circuitry adapted to convert a varying radio frequency signal strength into a serial data stream during a receive process.

Still another aspect of the invention provides an implantable pulse generator system, the system comprising a pulse generator including a housing sized and configured for implantation in subcutaneous tissue, circuitry carried within the housing and adapted for wireless telemetry, a rechargeable battery coupled to the circuitry and carried within the housing, and a power receiving coil carried within the housing and coupled to the circuitry, the power receiving coil for transcutaneously receiving an externally generated radio frequency magnetic field to recharge the rechargeable battery. The system also comprises an external controller including circuitry, a rechargeable battery coupled to the circuitry, and the circuitry adapted for wireless telemetry, and a charging coil coupled to the external controller for generating the radio frequency magnetic field to transcutaneously recharge the rechargeable battery. During a rechargeable battery recharge period, the external controller is adapted to be carried by a user with no connection to a power main to allow the user to be completely mobile.

Another aspect of the invention provides an implantable pulse generator including a stimulation component having an on state to generate a stimulation pulse and an off state, a receiver component selectively enabled to receive information using wireless telemetry, and a controller coupled to the stimulation component and the receiver component to enable operation of the receiver component only when the stimulation component is in the off state.

Yet another aspect of the invention provides an implantable pulse generator including a case, a rechargeable battery positioned within the case to provide operating power, charge management circuitry positioned within the case and coupled to the rechargeable battery, the charge management circuitry implementing a constant current phase and a constant voltage phase charge regime, a controller positioned within the case and coupled to the charge management circuitry, the controller for timing the constant voltage phase of the rechargeable battery charge regime, and a receive coil positioned in the case and coupled to the rechargeable battery, the receive coil receiving externally generated energy from a recharger to recharge the rechargeable battery.

The pulse generator is adapted to recharge a fully discharged rechargeable battery in less than about six hours. The controller further monitors the rechargeable battery voltage and terminates the charge regime after the rechargeable battery voltage has been in the constant voltage phase for greater than a predetermined time period. The controller terminates the charge regime by wireless telemetry communication with the recharger and instructing the recharger to stop recharging.

Another aspect of the invention provides a method of wireless telemetry communication of status information between an implanted pulse generator and an external controller including the steps of providing a pulse generator, the pulse generator comprising a housing sized and configured for implantation in subcutaneous tissue, circuitry carried within the housing and adapted for wireless telemetry, a rechargeable battery coupled to the circuitry and carried within the housing, the battery having a voltage, and a power receiving coil carried within the housing and coupled to the circuitry, the power receiving coil for transcutaneously receiving an externally generated radio frequency magnetic field to recharge the rechargeable battery.

The steps further including providing an external controller including circuitry adapted for wireless telemetry, and a charging coil for generating the radio frequency magnetic field to transcutaneously recharge the rechargeable battery, and during a battery recharge period and using wireless telemetry, the pulse generator transmitting status information back to the external controller to allow the external controller to automatically adjust up or down the magnitude of the radio frequency magnetic field and/or to instruct a user to reposition the charging coil, the status information adapted to allow optimal recharging of the pulse generator rechargeable battery. The instruction to the user may be a visual instruction and/or an audio instruction.

The steps may further may further include providing an instruction sheet to the user, the instruction sheet defining how to reposition the charging coil for optimal recharging based on the visual and/or audio indication provided by the external controller.

BRIEF DESCRIPTION OF THE DRAWINGS

FIG. 26A is a circuit diagram showing a possible circuit for the wireless telemetry feature used with the implantable pulse generator shown in FIGS. 3A through 3D.

FIG. 26B is a graphical view of the wireless telemetry transmit and receive process incorporated in the circuit diagram of FIG. 26A.

FIG. 36 is an elevation view, in partial section, of a lead and electrode of the type shown in FIG. 33 residing within an introducer sheath for implantation in a targeted tissue region, the anchoring members being shown retracted within the sheath.

FIG. 37 is a perspective view of a molded cuff electrode positioned about a target nerve N.

FIG. 38 is a diagrammatic view of the custom operating system software, including system software and application software.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENT

The various aspects of the invention will be described in connection with providing stimulation of central nervous system tissue, muscles, or nerves, or muscles and nerves for prosthetic or therapeutic purposes. That is because the features and advantages that arise due to the invention are well suited to this purpose. Still, it should be appreciated that the various aspects of the invention can be applied to achieve other objectives as well.

I. The Implantable Pulse Generator System

Figure 1:
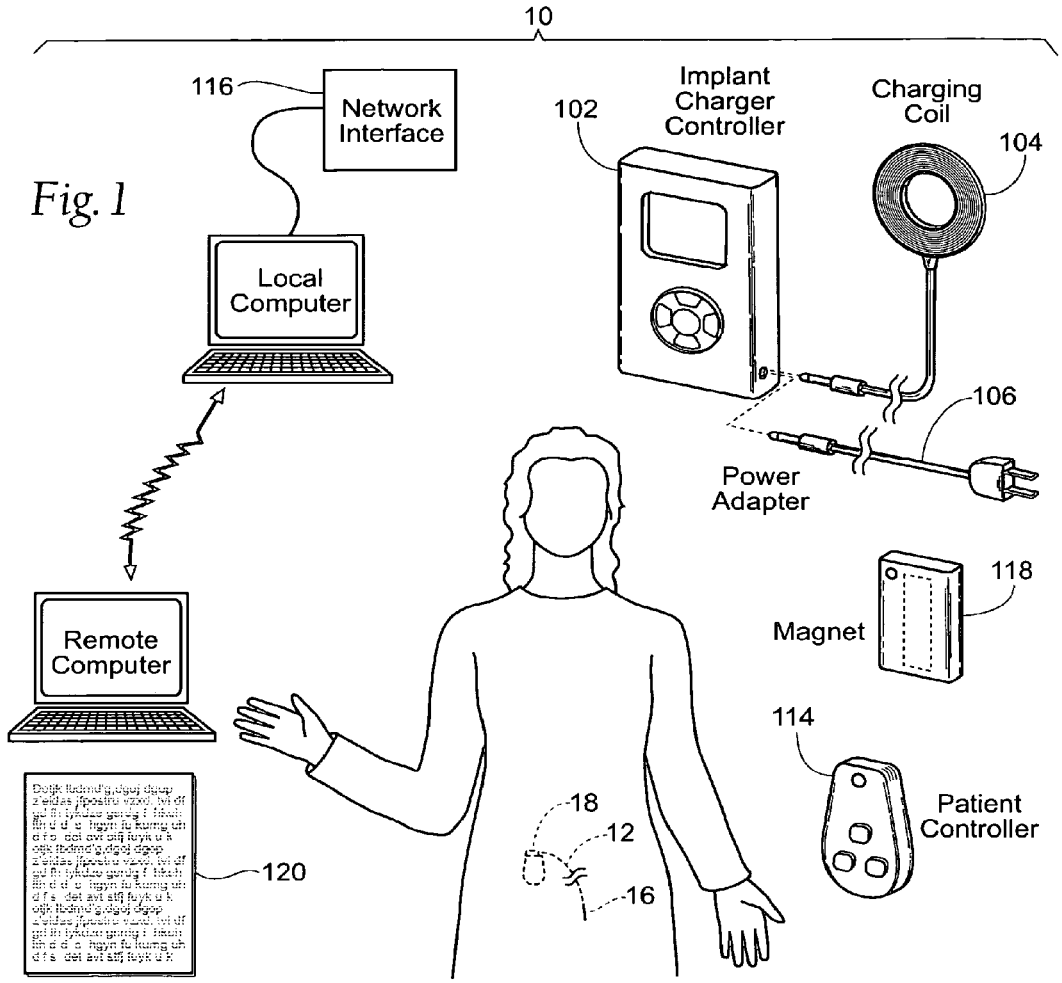
FIG. 1 is a diagrammatic view of a stimulation system that provides electrical stimulation to central nervous system tissue, muscles and/or nerves inside the body using a general purpose implantable pulse generator, the system including internal and external components that embody the features of the invention.
Figure 1:
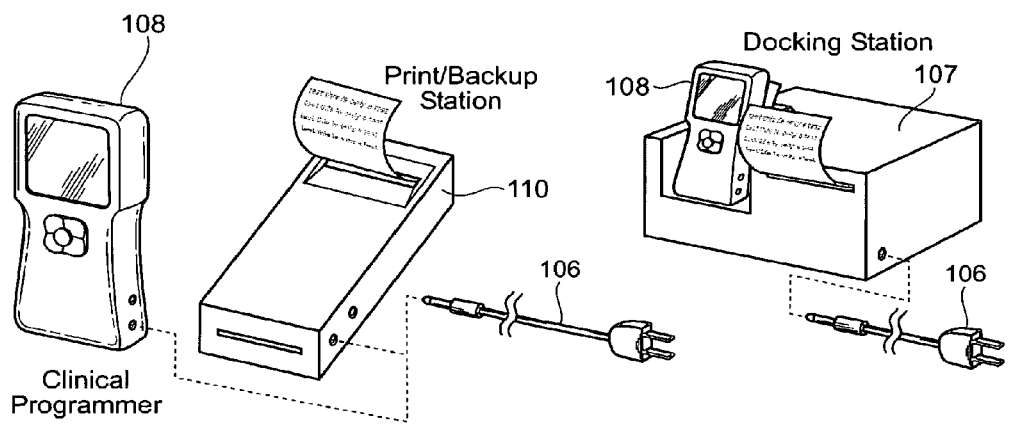

FIG. 1 shows in diagrammatic form an implantable pulse generator system 10. The implantable pulse generator system 10 can be used for stimulating a central nervous system tissue, nerve, or a muscle, or a nerve and a muscle to achieve a variety of therapeutic (treatment) or functional (restoration) purposes.

The implantable pulse generator system 10 may include both implantable components and external components. The implantable components may include, but are not limited to: an implantable pulse generator 18 coupled to a lead 12 and an electrode 16. The external components may include, but are not limited to: a clinical programmer 108, a print/backup station 110, a docking station 107, a network interface 116 (external controller derivative), an implant charger controller 102, a charging coil 104, a power adapter 106, a patient controller 114, an instruction sheet 120, and a magnet 118. Each of these components of the system 10 will be described in greater detail below.

As an exemplary embodiment, the implantable pulse generator may be used to provide therapeutic restoration for urinary urge incontinence by stimulation of afferent nerves. In this application, a sequence (regime) of nerve stimulation is provided to maintain a level of nervous system mediation that prevents spasms of the bladder-sensory reflex. The predefined stimulus regime may include: a programmable period of no stimulation (a gap), a transition from no stimulation to full stimulation (ramp up), a period of constant, full stimulation (burst), and transition back to no stimulation (ramp down). This cycle repeats indefinitely; except as may be modified by a clinician or patient request for higher or lower stimulus strength. That request may be made using a clinical programmer 108, the implant charger controller 102, or the patient controller 114, for example, using the wireless telemetry 112. Instructions 120 may be provided to describe operation and usage for all components and all users (i.e., clinician and patient).

A. Implantable Pulse Generator Components

Figure 2A:
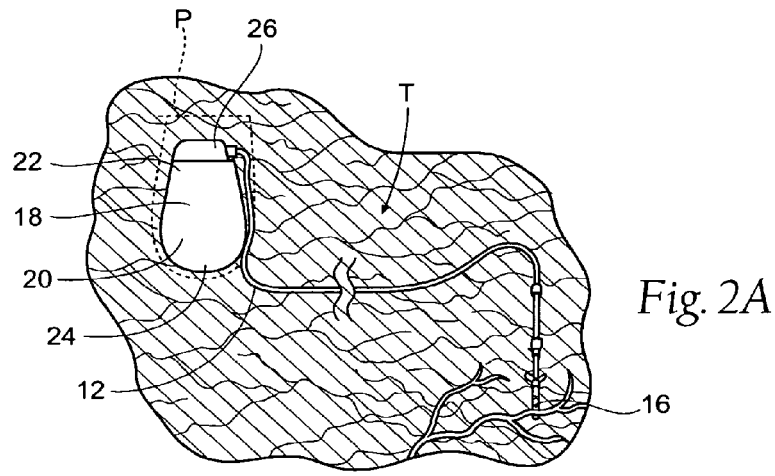
FIG. 2A is an anatomical view showing an implantable pulse generator with a lead and electrode implanted in tissue.

FIG. 2A shows the implantable pulse generator 18 coupled to the implantable lead 12. The distal end of the lead 12 includes at least one electrically conductive surface, which will in shorthand be called an electrode 16. The electrode 16 may also be positioned along the length of the lead 12. The electrode 16 is implanted in electrical conductive contact with at least one functional grouping of nerve tissue, muscle, or at least one nerve, or at least one muscle and nerve, depending on the desired functional and/or therapeutic outcome desired. The lead 12, electrode 16, and the implantable pulse generator 18 are shown implanted within a tissue region T of a human or animal body.

The implantable pulse generator 18 is housed within an electrically conductive titanium case or housing 20 which can also serve as a return electrode for the electrical stimulus current introduced by the lead/electrode when operated in a monopolar configuration. The implantable pulse generator 18 includes a connection header 26 that desirably carries a plug-in receptacle for the lead 12. In this way, the lead 12 electrically connects the electrode 16 to the implantable pulse generator 18. The case 20 is desirably shaped with a smaller end 22 and a wider end 24, with the header 26 coupled to the smaller end 22. As FIG. 2A shows, this geometry allows the smaller end 22 of the case 20 (including the header 26), to be placed into the skin pocket P first, with the wider end 24 being pushed in last.

Figure 39:
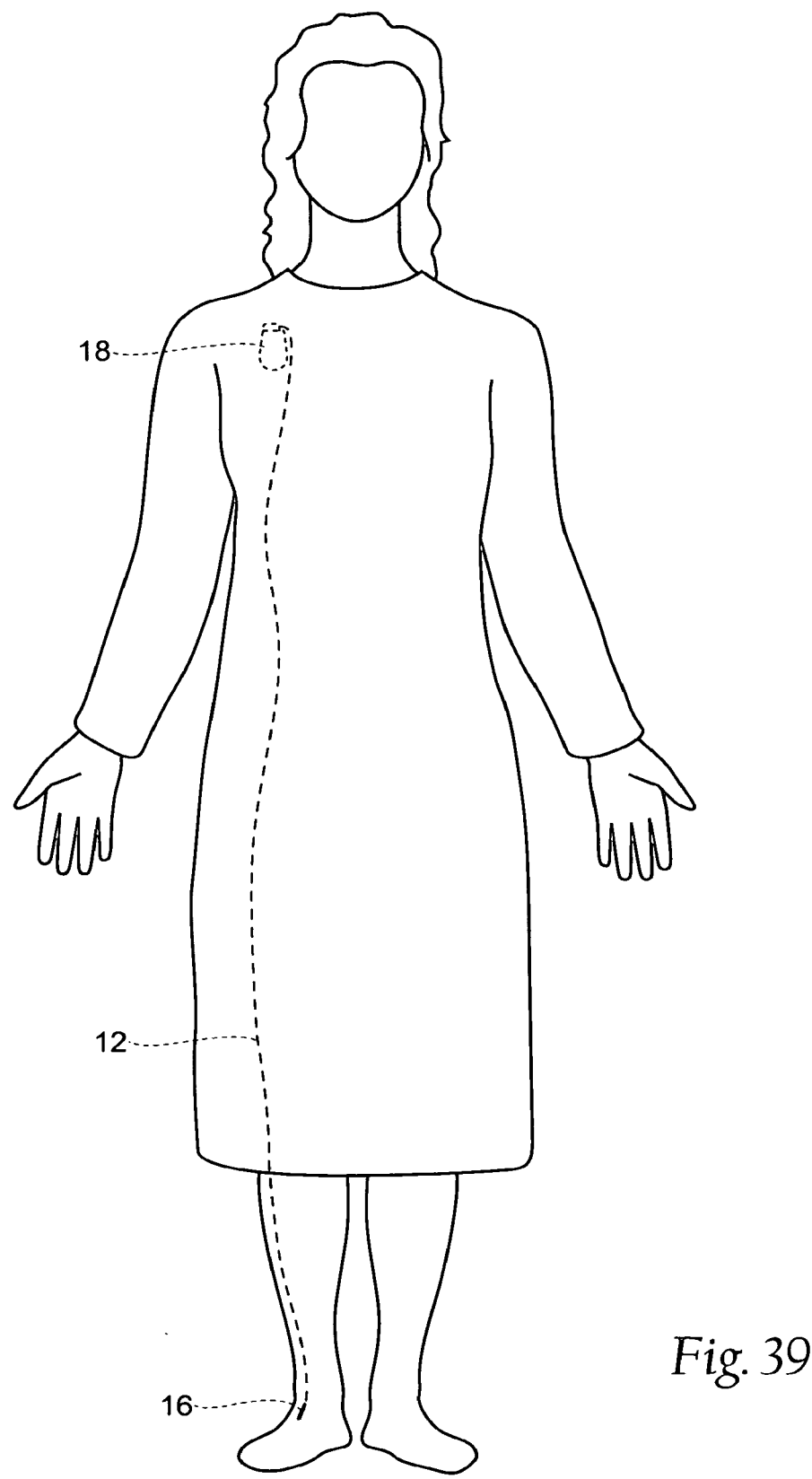
FIG. 39 is an anatomic view showing the long lead length feature of the implantable pulse generator, the lead capable of extending an anatomical furthest distance to deliver electrical stimulation.

The implantable pulse generator 18 is sized and configured to be implanted subcutaneously in tissue, desirably in a subcutaneous pocket P, which can be remote from the electrode 16, as FIG. 2A shows. The implantable pulse generator 18 is capable of driving large electrical resistance occurring in long lead lengths, e.g., the lead 12 is capable of extending an anatomical furthest distance. The anatomical furthest distance may be the full length of the body; from head to toe in a human. For example, the implantable pulse generator could be implanted in an upper chest region and the lead could extend down to the foot (see FIG. 39). This capability allows the implantable pulse generator placement to be selected conveniently and not be constrained by the location of the electrode.

In order to accomplish driving the generated electrical stimulation current or pulses from the implantable pulse generator 18 through the lead 12 extending the anatomic furthest distance, the implantable pulse generator includes a software programmable VHH power supply 134 (to be described in greater detail later) that can produce the necessary higher voltages. This power supply is software programmable to provide a voltage large enough to drive the requested stimulation current through the lead 12 and electrode 16 circuit resistance/impedance. The VHH power supply 134 can be adjusted up to about 27 VDC. This relatively large voltage allows the delivery of cathodic phase currents up to about 20 mA into long lead lengths or into higher impedance electrodes.

In an exemplary application, (an intramuscular stimulating electrode 16 with the case 20 as the return electrode, for example), the total tissue access resistance of the electrode-to-tissue interface is between about 100 ohms and 500 ohms. The lead 12 connecting the electrode(s) 16 to the implantable pulse generator 18 have resistances that are roughly proportional to the length of the lead. Typical leads have resistances in the range of about 2 ohms to 5 ohms of electrical resistance for every centimeter of lead length. Thus, a relatively long lead, 70 cm for example, may have about 350 ohms of lead resistance. Combined with about 500 ohms of tissue access resistance, this gives a total patient circuit resistance of up to about 850 ohms. To drive 20 mA through this circuit, the VHH power supply 134 would be programmed to provide about 17 VDC.

Desirably, the implantable pulse generator 18 is sized and configured to be implanted using a minimally invasive surgical procedure. The surgical procedure may be completed in a number of steps. For example, once a local anesthesia is established, the electrode 16 is positioned at the target site. Next, a subcutaneous pocket P is made and sized to accept the implantable pulse generator 18. A finger dissection, e.g., the clinician's thumb, for example, may be used to form the pocket P after an initial incision has been made. The pocket P is formed remote from the electrode 16. Having developed the subcutaneous pocket P for the implantable pulse generator 18, a subcutaneous tunnel is formed for connecting the lead 12 and electrode 16 to the implantable pulse generator 18. The lead 12 is routed through the subcutaneous tunnel to the pocket site P where the implantable pulse generator 18 is to be implanted. The lead 12 is then coupled to the implantable pulse generator 18, and both the lead 12 and implantable pulse generator 18 are placed into the subcutaneous pocket, which is sutured closed.

Figure 4A:
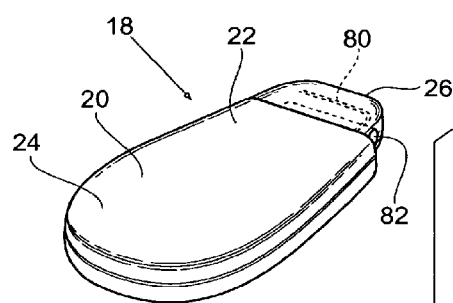
FIG. 4A is a perspective view of the general purpose implantable pulse generator as shown in FIG. 1, without a lead and electrode.
Figure 4C:
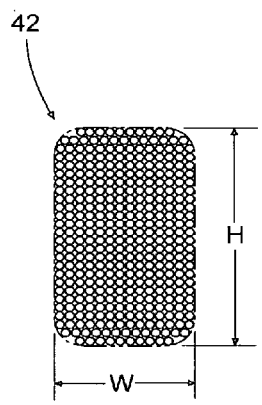
FIG. 4C is a section view of the receive coil taken generally along line 4C-4C in FIG. 4B.
Figure 4D:
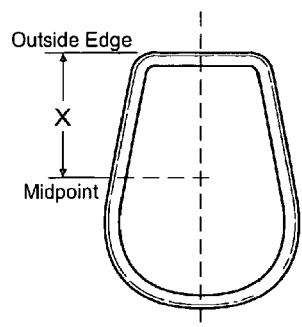
FIG. 4D is a top plan view of the receive coil shown in FIG. 4C, showing the maximum outside dimension.
Figure 4B:
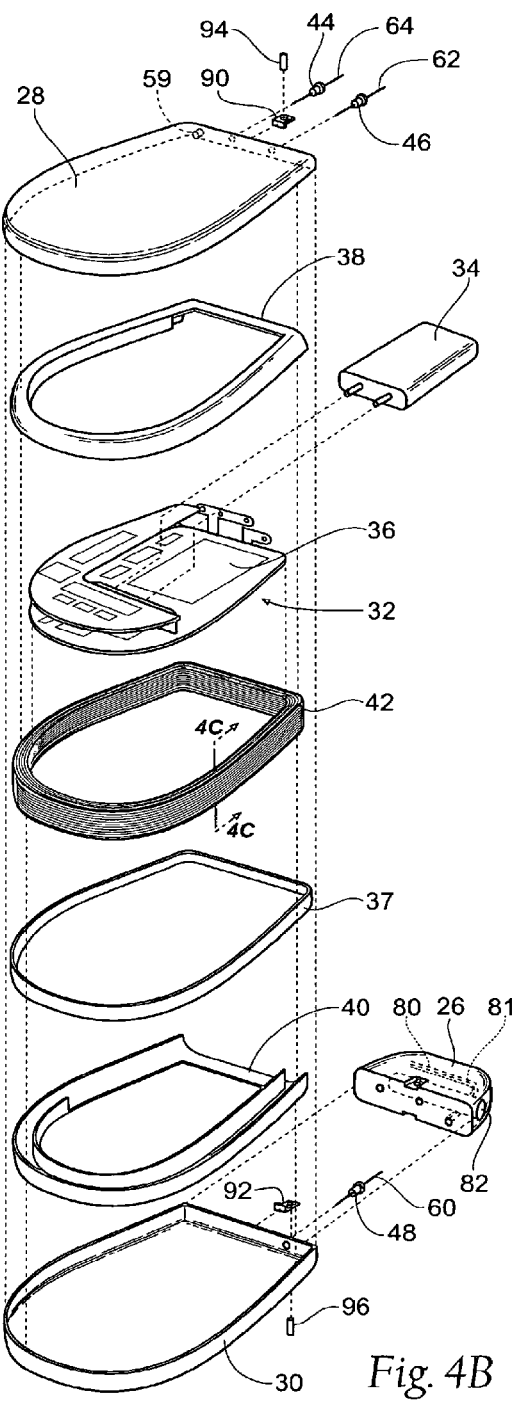
FIG. 4B is an exploded view of the implantable pulse generator as shown in FIG. 4A, showing the general components that make up the implantable pulse generator.

FIG. 4B shows an exploded view of the implantable pulse generator 18 shown in FIG. 4A. As shown in FIG. 4B, the case 20 includes a bottom case component 28 and a top case component 30. Within the bottom case 28 and top case 30 is positioned a circuit 32 for generating the electrical stimulation waveforms. An on-board, primary or rechargeable battery 34 desirably provides the power. The implantable pulse generator 18 also desirably includes an on-board, programmable microcontroller 36, which carries operating system code. The code expresses pre-programmed rules or algorithms under which the desired electrical stimulation waveforms are generated by the circuit 32.

According to its programmed rules, when switched on, the implantable pulse generator 18 generates prescribed stimulation waveforms through the lead 12 and to the electrode 16. These stimulation waveforms stimulate the central nervous system tissue, muscle, nerve, or both nerve and muscle tissue that lay in electrical conductive contact (i.e., within close proximity to the electrode surface where the current densities are high) with the electrode 16, in a manner that achieves the desired therapeutic (treatment) or functional restoration result. Examples of desirable therapeutic (treatment) or functional restoration indications will be described in greater detail in section III.

Within the case 20 is also positioned a bottom nest 38 and a top nest 40. The plastic nests 38 and 40 provide support for the circuitry 32, a weld band 37, and a receive coil 42. A number of feed-thrus 44, 46, 48 are coupled to the bottom case 28 and/or top case 30 and provide electrical connectivity between the circuitry within the case and a header 26 while maintaining the hermetic seal of the case. The header 26 is positioned over the feed-thrus 44, 46, 48 at the smaller end 22 of the case 20.

1. Implantable Pulse Generator Assembly

Figure 5:
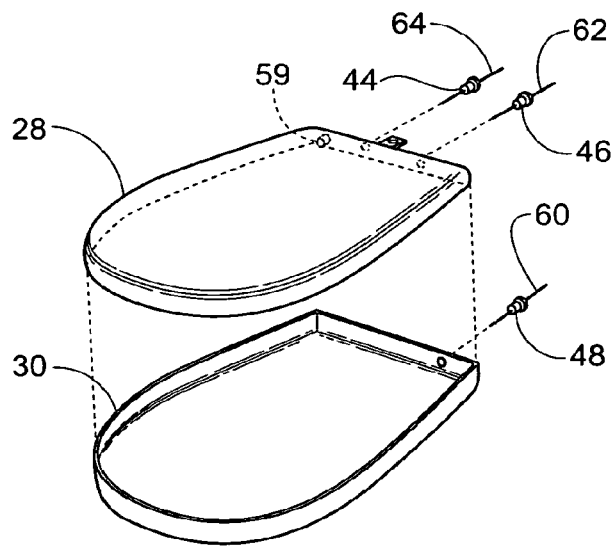
FIGS. 5 through 15 are perspective views showing possible steps for assembling the implantable pulse generator shown in FIG. 4B.
Figure 6:
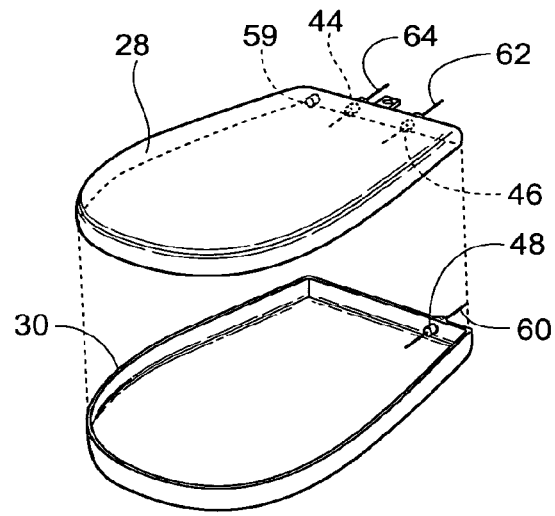

A representative process for assembling the implantable pulse generator 18 will now be described. It is to be appreciated that the process for assembling the implantable pulse generator 18 is not intended to be limiting, but merely an example to describe the interrelation of the implantable pulse generator 18 components shown in FIG. 4B. As FIGS. 5 and 6 shows, the feed-thrus 44, 46, 48 are coupled (e.g., welded or braised), to preexisting apertures in the bottom case 28 and top case 30. As shown, feed-thru 44 and 46 are coupled to the bottom case 28 and feed-thru 48 is coupled to the top case 30.

As shown in FIG. 4B, feed-thru 48 is coupled to the wireless telemetry antenna 80. The antenna 80 may be a conductor separate from conductor 60 (see FIG. 7), or it may be the same conductor. If a separate conductor is used (for example because a metal with better electrical conductivity is deemed desirable for operation of the antenna), then there will be a coupling between the two conductors (60 & 80). It is likely that this coupling will be a crimp connection or a weld, although not limited to only these coupling configurations.

Figure 7:
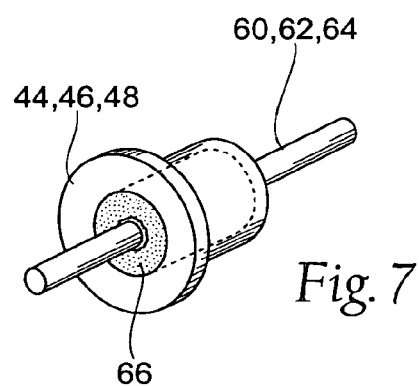

Each feed-thru 44, 46, 48, includes a feed-thru conductor 64, 62, 60 respectively, to be coupled to the circuitry 32 and the header 26. FIG. 7 shows feed-thru 48 in detail. As can be seen, a conductor 60 passes through a glass or ceramic insulator 66 of the feed-thru.

Figure 8A:
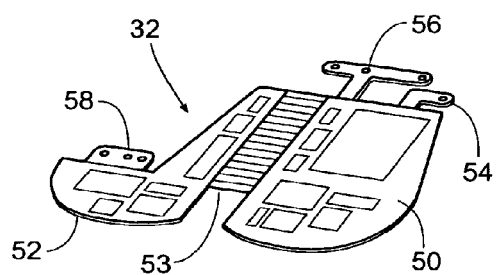
Figure 8B:
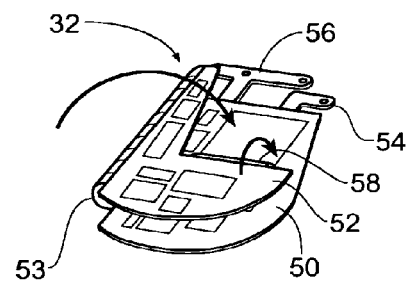
Figure 8C:
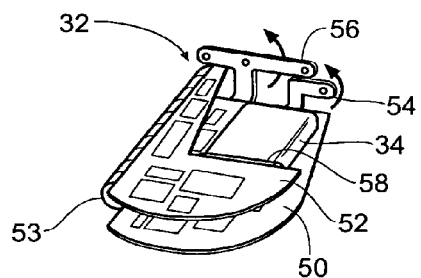

The circuitry 32 is sized and configured to precisely fit within the top nest 40 and bottom nest 38, which in turn precisely fit within the top case 30 and bottom case 28. As can be seen in FIG. 8A, the circuitry 32 first comprises a generally flat configuration using flexible circuit board technology. The circuitry 32 comprises a top circuit portion 50 electrically coupled to a bottom circuit portion 52 by way of a flexible hinge portion 53. The top circuit 50 includes an antenna tab 54 and a lead tab 56. The bottom circuit 52 includes a battery tab 58. In order to fit the circuitry 32 within the case 20, the bottom circuit 52 is folded over the top circuit 50 and the battery tab 58 is folded inward toward the top circuit 50, as can be seen in FIG. 8B. The battery 34 may then be positioned and coupled (e.g., soldered), to the inward facing battery tab 58. The lead tab 56 may then be folded upward and inward toward the bottom circuit 52, and the antenna tab 54 may be folded upward and inward toward the bottom circuit, as can be seen in FIG. 8C. The circuitry 32, including the battery 34, may now be positioned within the bottom case 28 and top case 30.

The bottom case 28 and the top case 30 may be positioned in a fixture (not shown) to aid with the assembly process. The antenna tab 54 and the lead tab 56 are electrically coupled to their respective feed-thrus in the bottom case 28 and top case 30.

Figure 9:
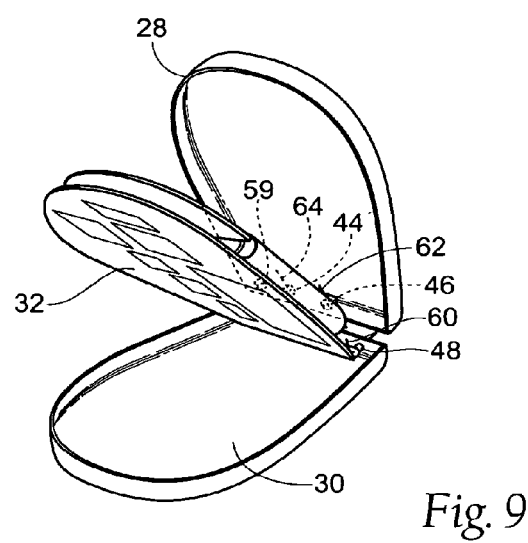

As shown in FIG. 9, conductor 60 of feed-thru 48 is coupled to the antenna tab 54, and conductors 62 and 64 of feed-thrus 46 and 44 respectively are coupled to lead tab 56. Lead tab 56 is also coupled to a ground pin 59 coupled to the inside of the bottom cover 28.

Figure 10:
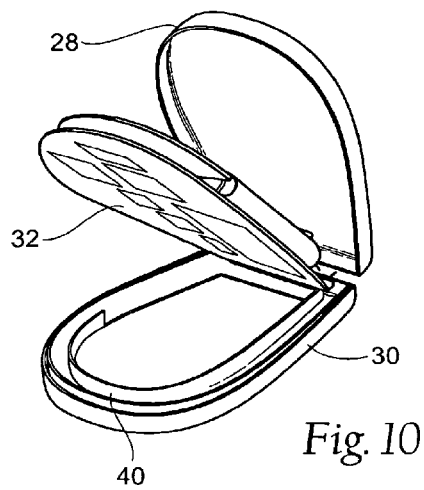
Figure 11:
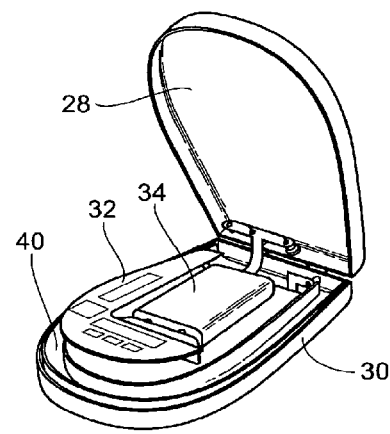
Figure 12:
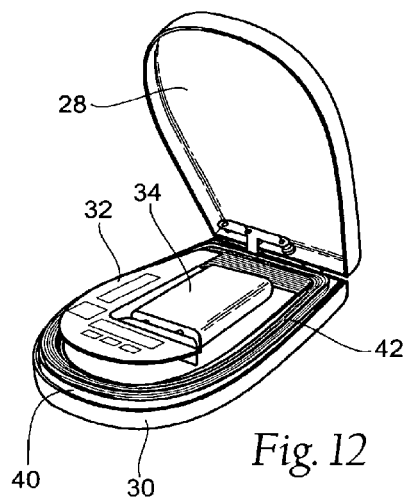
Figure 14:
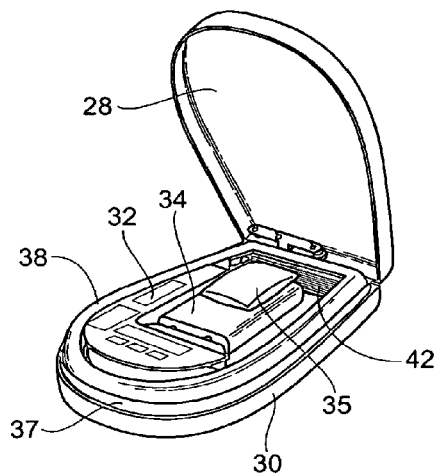
Figure 15:
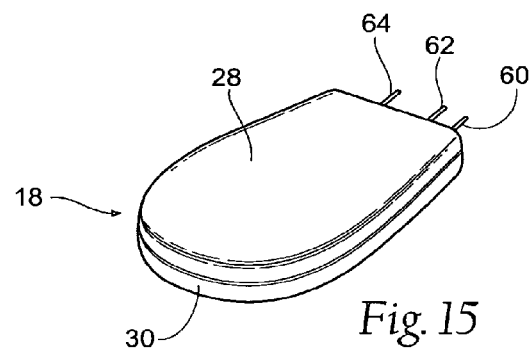

Next, the top nest 40 is positioned within the top case 30 (see FIG. 10). The circuitry 32 is then positioned within the top case 30 and the top nest 40. The receive coil 42 is then seated within the top nest 40 and electrically coupled to the circuitry 32 (see FIGS. 11 and 12). The bottom nest 38 is then seated over the receive coil 42 and the circuitry 32 (see FIG. 13), and the weld band 37 is secured over the top nest 40 and bottom nest 38 (see FIG. 14). A "getter" 35 may be positioned within the bottom case 28 and the top case 30 at any time prior to putting the case pieces together. The getter 35 helps to eliminate any moisture or other undesirable vapors that may remain in the case 20 after the case has been sealed. The bottom case 28 can then be positioned on the top case 30 (see FIGS. 15 and 16).

Figure 17:
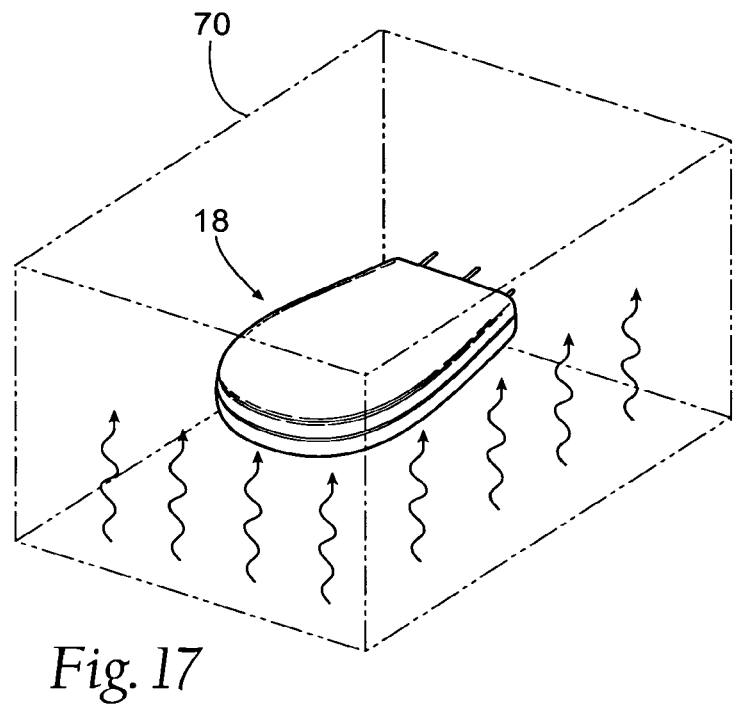
FIG. 17 is a perspective view of the implantable pulse generator during a vacuum bake-out process and prior to assembling the header.
Figure 18:
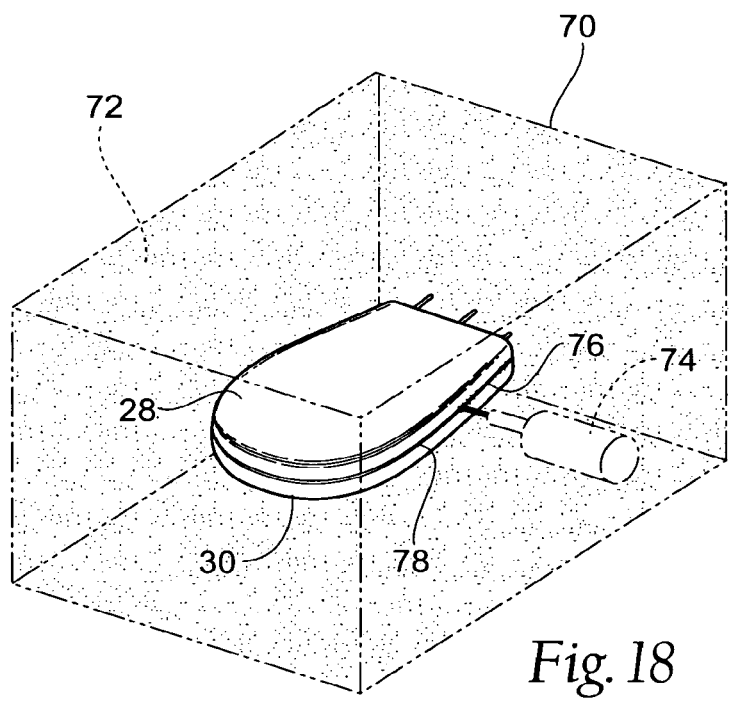
FIG. 18 is a perspective view of the implantable pulse generator during the backfill and welding process and prior to assembling the header.

Next, the assembled implantable pulse generator 18 is subjected to a vacuum bake-out process in chamber 70 (see FIG. 17). The vacuum bake-out process drives out any moisture content within the unsealed implantable pulse generator 18 and drives out any other volatile contaminants in preparation for the final sealing of the implantable pulse generator 18. After a predetermined bake-out period (e.g., 45 degrees Celsius to 100 degrees Celsius, and for 24 to 48 hours), the chamber 70 is then backfilled with an inert gas or gas mixture 72, such as helium-argon (see FIG. 18). A laser welder 74 then applies a weld 76 to the seam 78 where the bottom case 28 and top case 30 come together. The weld band 37 protects the components within the case 20 during the laser welding process.

Figure 16:
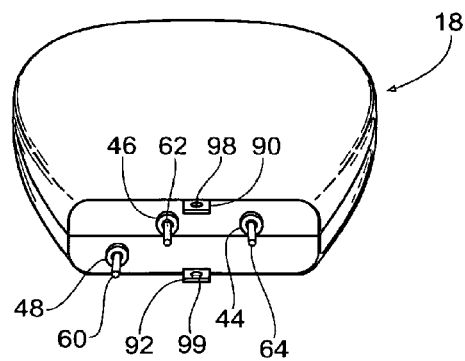
FIG. 16 is a perspective view of the smaller end of the implantable pulse generator shown in FIG. 4A prior to assembling the header to the implantable pulse generator.
Figure 19:
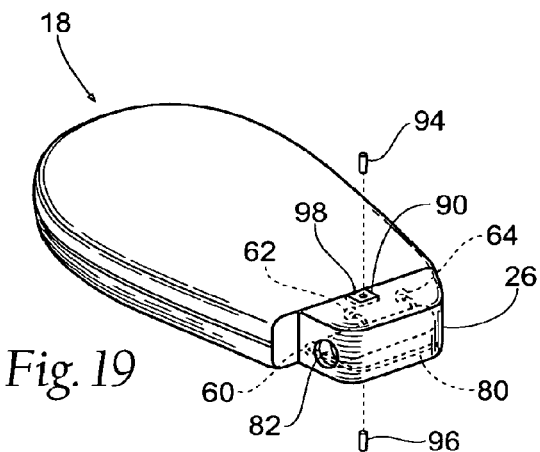
FIG. 19 is a perspective view of the implantable pulse generator shown in FIG. 4A with the header positioned for attachment.

A final assembly process may include coupling the header 26 to the smaller end 22 of the case 20 and the exposed electrical conductors 60, 62, 64 (see FIGS. 16 and 19). The header 26 includes connector blocks for the IS-1 connector inserted or molded within. The header 26 also has slots or passages molded within for holding the antenna 80, an antenna insert 81, the conductors 62 and 64 of feed-thrus 44 and 46, and the header brackets 98 and 99 (see FIG. 4B). The thin plastic antenna insert 81 is used to guide the bending of the antenna 80 and to secure the antenna 80 inside the header 26.

With the antenna 80 bent around the antenna insert 81, and the other feed-thru conductors 62 and 64 sticking out straight, the header 26 is slipped onto the flat face of the welded case (the flat face as shown in FIG. 16). The antenna 80, the antenna insert 81, the feed-thru conductors 62 and 64, and the header brackets 98 and 99, all slip into slots or passages molded into the header 26 as the header fits flush against the case. The feed-thru conductors 62 and 64 are then welded to the connector blocks inside the header through slots or apertures molded in the header. Anchor pins 94 and 96 are slipped through the apertures 98 and 99 in the header brackets 90 and 92 and into anchor pin slots or apertures molded into the header 26. The anchor pins 94 and 96 are welded to the header brackets 90 and 92 and mechanically secure the header to the case through the header brackets.

Any remaining space between the header 26 and the case 20 may also be backfilled with an adhesive, such as silicone, to seal the header 26 to the case 20 and fill any remaining gaps. Similarly, the holes through which the anchor pins were installed and the holes through which the feed-thru conductors were welded to the connector blocks are also backfilled with adhesive, such as silicone. The final result is a hermetically sealed implantable pulse generator 18, as seen in FIGS. 20 and 21.

Figure 20:
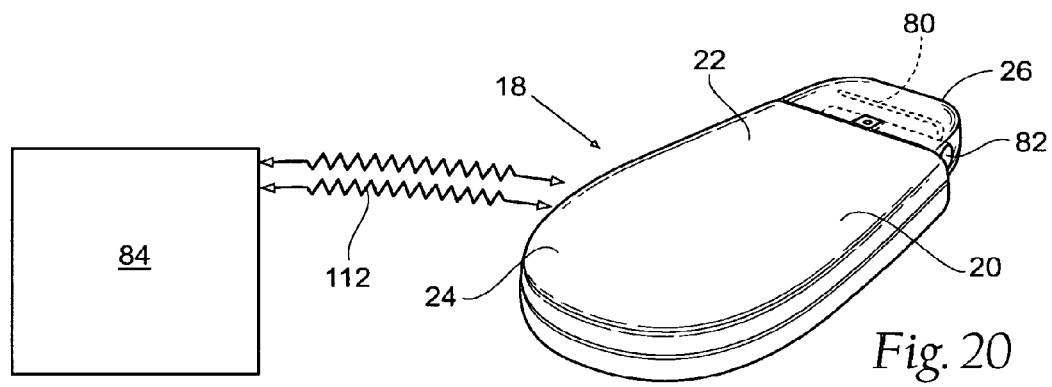
FIG. 20 is a diagrammatic view showing operating system software being downloaded to the implantable pulse generator using wireless telemetry.
Figure 21:
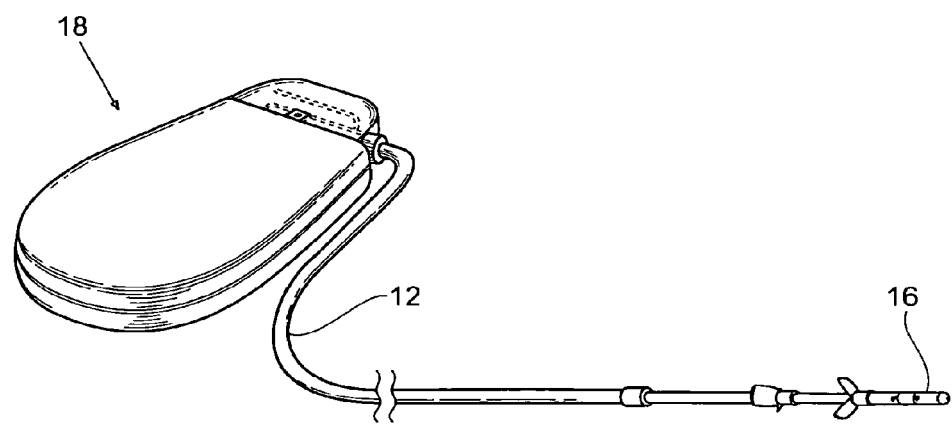
FIG. 21 is a perspective view of the implantable pulse generator shown in FIG. 4A, including a lead and electrode.

FIG. 20 also shows programming the implantable pulse generator 18 with operating system software, system software, and/or application software. A programmer 84 may be used to download system software, which may or may not include the application software, to the implantable pulse generator 18. This feature of programming, or reprogramming, the implantable pulse generator 18 allows the implantable pulse generator to be manufactured and partially or fully programmed. The implantable pulse generator may then be put into storage until it is to be implanted, or until it is known what application software is to be installed. The downloading of the application software or changes to the application software can take place anytime prior to implantation. This feature makes use of a set of software which was programmed into the microcontroller during the manufacturing process. The programmer 84 may be similar to the clinical programmer 108 or a modified clinical programmer, except with added features to allow for the programming or reprogramming of the implantable pulse generator 18.

B. Implantable Pulse Generator Features

Desirably, the size and configuration of the implantable pulse generator 18 makes possible its use as a general purpose or universal device (i.e., creating a platform technology), which can be used for many specific clinical indications requiring the application of pulse trains to central nervous system tissue, muscle and/or nervous tissue for therapeutic (treatment) or functional restoration purposes. Most of the components of the implantable pulse generator 18 are desirably sized and configured so that they can accommodate several different indications, without major change or modification. Examples of components that desirably remains unchanged for different indications include the case 20, the battery 34, the power management circuitry 130, the microcontroller 36, much of the operating system software (firmware) of the embedded code, and the stimulus power supply (VHH and VCC). Thus, a new indication may require only changes to the programming of the microcontroller 36. Most desirably, the particular code may be remotely embedded in the microcontroller 36 after final assembly, packaging, and sterilization of the implantable pulse generator 18.

Certain components of the implantable pulse generator 18 may be expected to change as the indication changes; for example, due to differences in leads and electrodes, the connection header 26 and associated receptacle(s) for the lead may be configured differently for different indications. Other aspects of the circuit 32 may also be modified to accommodate a different indication; for example, the stimulator output stage(s), or the inclusion of sensor(s) and/or sensor interface circuitry for sensing myoelectric signals.

In this way, the implantable pulse generator 18 is well suited for use for diverse indications. The implantable pulse generator 18 thereby accommodates coupling to a lead 12 and an electrode 16 implanted in diverse tissue regions, which are targeted depending upon the therapeutic (treatment) or functional restoration results desired. The implantable pulse generator 18 also accommodates coupling to a lead 12 and an electrode 16 having diverse forms and configurations, again depending upon the therapeutic or functional effects desired. For this reason, the implantable pulse generator can be considered to be general purpose or "universal."

1. Desirable Technical Features

The implantable pulse generator 18 can incorporate various technical features to enhance its universality.

a. Small, Composite Case

Figure 3A:
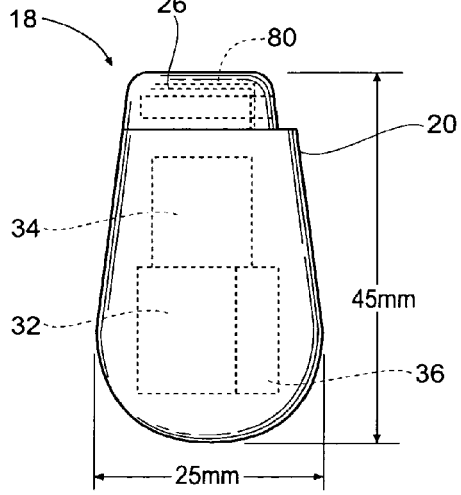
FIGS. 3A and 3B are front and side views of the general purpose implantable pulse generator as shown in FIG. 1, which is powered by a rechargeable battery.
Figure 3B:
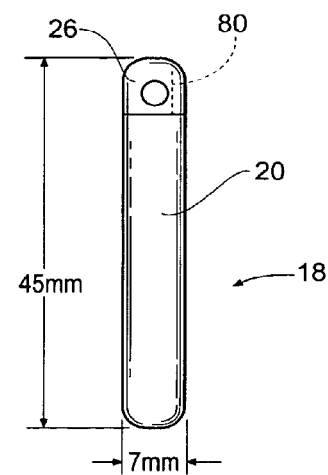

According to one desirable technical feature, the implantable pulse generator 18 can be sized small enough to be implanted (or replaced) with only local anesthesia. As FIGS. 3A and 3B show, the functional elements of the implantable pulse generator 18 (e.g., circuit 32, the microcontroller 36, the battery 34, and the connection header 26) are integrated into a small, composite case 20. As can be seen, the case 20 defines a small cross section; e.g., about (5 mm to 12 mm thick)×(15 mm to 40 mm wide)×(40 mm to 60 mm long). The overall weight of the implantable pulse generator 18 may be approximately eight to fifteen grams. These dimensions make possible implantation of the case 20 with a small incision; i.e., suitable for minimally invasive implantation. Additionally, a larger, and possibly similarly shaped implantable pulse generator might be required for applications with more stimulus channels (thus requiring a large connection header) and or a larger internal battery.

Figure 3C:
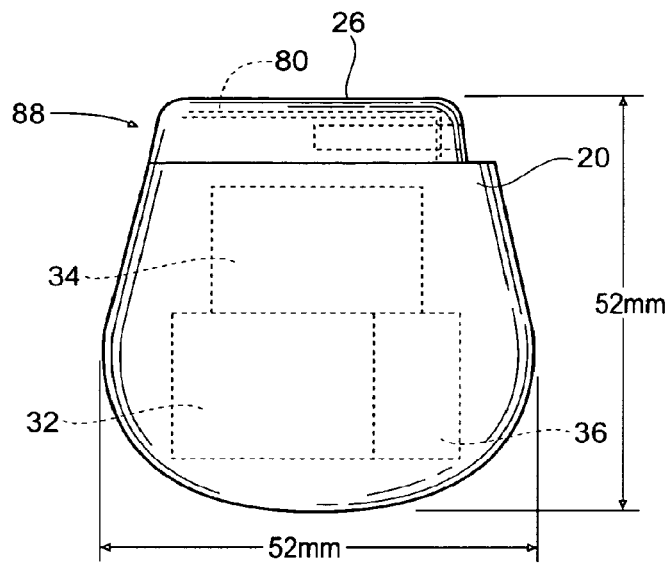
FIGS. 3C and 3D are front and side views of an alternative embodiment of a general purpose implantable pulse generator as shown in FIG. 1, which is powered using a primary battery.
Figure 3D:
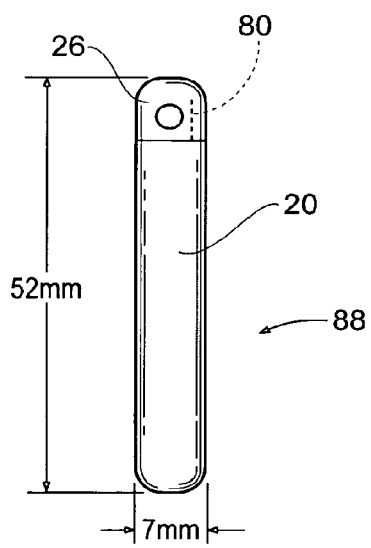

FIGS. 3C and 3D illustrate an alternative embodiment 88 of the implantable pulse generator 18. The implantable pulse generator 88 utilizes a primary battery 34. The implantable pulse generator 18 shares many features of the primary cell implantable pulse generator 88. Like structural elements are therefore assigned like numerals. As can be seen in FIGS. 3C and 3D, the implantable pulse generator 88 may comprise a case 20 having a small cross section, e.g., about (5 mm to 15 mm thick)×(45 mm to 60 mm wide)×(45 mm to 60 mm long). The overall weight of the implantable pulse generator 88 may be approximately fifteen to thirty grams These dimensions make possible implantation of the case 20 with a small incision; i.e., suitable for minimally invasive implantation.

The case 20 of the implantable pulse generator 18 is desirably shaped with a smaller end 22 and a larger end 24. As FIG. 2A shows, this geometry allows the smaller end 22 of the case 20 to be placed into the skin pocket P first, with the larger end 22 being pushed in last.

As previously described, the case 20 for the implantable pulse generator 18 comprises a laser welded titanium material. This construction offers high reliability with a low manufacturing cost. The clam shell construction has two stamped or successively drawn titanium case halves 28, 30 that are laser welded around the internal components and feed-thrus 44, 46, 48. The molded plastic spacing nests 38, 40 is used to hold the battery 34, the circuit 32, and the power recovery (receive) coil 42 together and secure them within the titanium case 20.

Figure 2B:
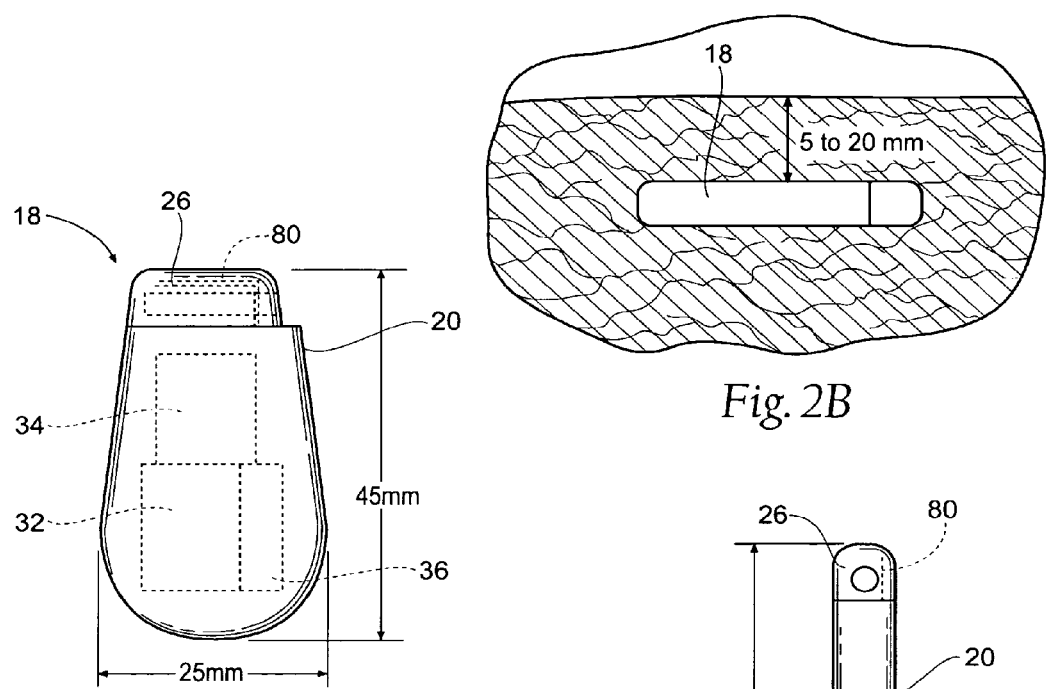
FIG. 2B is a side view showing a representative implant depth of the implantable pulse generator in tissue.

As can be seen in FIG. 2B, the implantable pulse generator 18 may be implanted at a target implant depth of not less than about five millimeters beneath the skin, and not more than about twenty millimeters beneath the skin, although this implant depth may change due to the particular application, or the implant depth may change over time based on physical conditions of the patient. The targeted implant depth is the depth from the external tissue surface to the closest facing surface of the implantable pulse generator 18.

The thickness of the titanium for the case 20 is selected to provide adequate mechanical strength while balancing the greater power absorption and shielding effects to the low to medium frequency magnetic field 100 used to transcutaneously recharge the implantable rechargeable battery 34 with thicker case material (the competing factors are poor transformer action at low frequencies—due to the very low transfer impedances at low frequencies—and the high shielding losses at high frequencies). The selection of the titanium alloy and its thickness ensures that the titanium case allows adequate power coupling to recharge the secondary power source (described below) of the implantable pulse generator 18 at the target implant depth using a low to medium frequency radio frequency (RF) magnetic field 100 from an implant charger controller 102 and associated charging coil 104 positioned over or near the implantable pulse generator 18 (see FIGS. 22A and 22B).

b. Internal Power Source

According to one desirable technical feature, the implantable pulse generator 18 desirably possesses an internal battery capacity or charge sufficient to allow operation with a recharging duty cycle of not more frequently than once per week for many or most clinical applications. The battery 34 of the implantable pulse generator 18 desirably can be recharged in less than approximately six hours with a recharging mechanism that allows the patient to sleep in bed or carry on most normal daily activities while recharging the battery 34 of the implantable pulse generator 18. The implantable pulse generator 18 desirably has a service life of greater than three years with the stimulus being a high duty cycle, e.g., virtually continuous, low frequency, low current stimulus pulses, or alternatively, the stimulus being higher frequency and amplitude stimulus pulses that are used only intermittently, e.g., a very low duty cycle.

To achieve this feature, the battery 34 of the implantable pulse generator 18 desirably comprises a secondary (rechargeable) power source; most desirably a Lithium Ion battery 34. Given the average quiescent operating current (estimated at 8 µA plus 35 µA for a wireless telemetry receiver pulsing on twice every second) and a seventy percent efficiency of the stimulus power supply, a 1.0 Amp-hr primary cell battery can provide a service life of less than two years, which is too short to be clinically or commercially viable for most indications. Therefore, the implantable pulse generator 18 desirably incorporates a secondary battery, e.g., a Lithium Ion rechargeable battery that can be recharged transcutaneously. Given representative desirable stimulation parameters (which will be described later), a Lithium Ion secondary battery with a capacity of at least 30 mA-hr will operate for over three years. Lithium Ion implant grade batteries are available from a domestic supplier. A representative battery capacity for one embodiment having a capacity of up to four stimulus channels provides about 130 to about 250 milliWatt-hr (approximately 30 milliAmp-hr to 65 milliAmp-hr) in a package configuration that is of appropriate size and shape to fit within the implantable pulse generator 18. For an alternative embodiment having a capacity of eight or more stimulus channels, a representative battery capacity provides about 250 to about 500 milliWatt-hr (approximately 66 milliAmp-hr to 131 milliAmp-hr).

The implantable pulse generator 18 desirably incorporates circuitry and/or programming to assure that the implantable pulse generator 18 will suspend stimulation at a first remaining battery capacity and as the remaining capacity decreases, eventually suspend all operations when only a safety margin of battery capacity remains. For example, the implantable pulse generator 18 may be adapted to suspend stimulation at the first remaining battery capacity (e.g., about fifteen percent to about thirty percent of battery capacity remaining), and perhaps fall-back to only very low rate telemetry, and eventually suspends all operations when the battery 34 has reached the safety margin, i.e., a second remaining battery capacity (e.g., about five percent to about twenty percent of battery capacity remaining). At this second remaining battery capacity, the battery 34 has discharged the majority of its capacity, described as a fully discharged battery, and only the safety margin charge remains. Once in this Dormant mode, the implantable pulse generator 18 is temporarily inoperable and inert. The safety margin charge ensures that the implantable pulse generator may be able to remain in the Dormant mode and go without recharging for at least six months. A delay in recharging for at least six months will not cause permanent damage or permanent loss of capacity to the lithium battery 34. If the battery 34 goes without charging for much longer than six months, the battery's self-discharge may cause a loss of battery capacity and/or permanent damage.

Figure 22A:
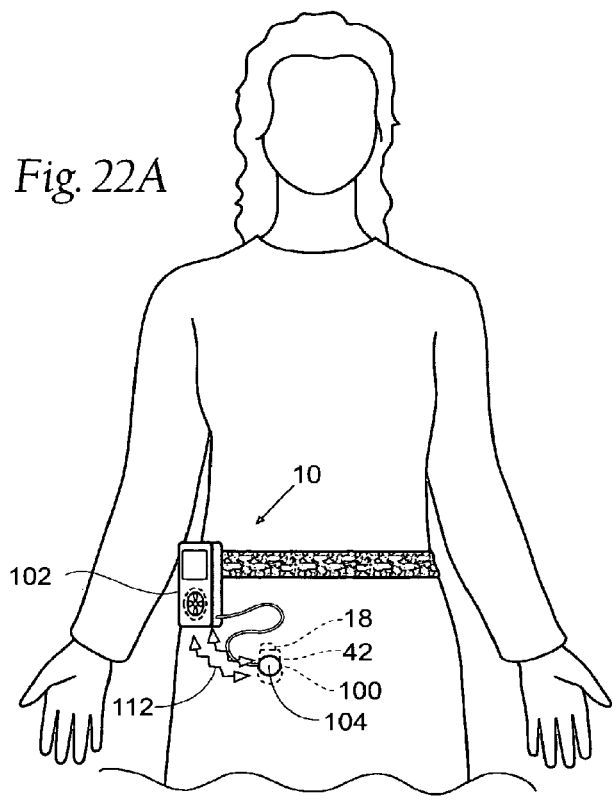
FIG. 22A is an anatomic view showing the implantable pulse generator shown in FIGS. 3A and 3B having a rechargeable battery and shown in association with a transcutaneous implant charger controller (battery charger) including a separate, cable coupled charging coil which generates the RF magnetic field, and also showing the implant charger controller using wireless telemetry to communicate with the implantable pulse generator during the charging process.
Figure 22B:
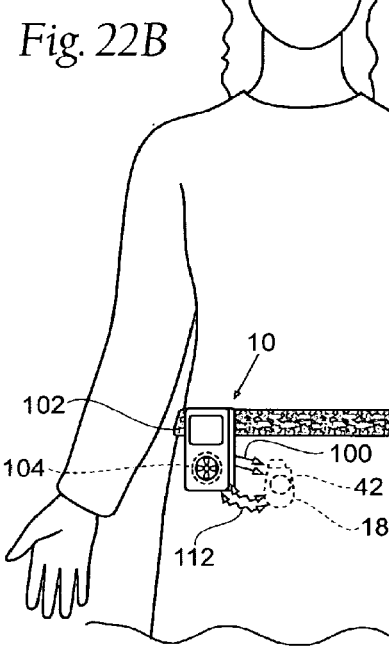
FIG. 22B is an anatomic view showing the transcutaneous implant charger controller as shown in FIG. 22A, including an integral charging coil which generates the RF magnetic field, and also showing the implant charger controller using wireless telemetry to communicate with the implantable pulse generator.

The power for recharging the battery 34 of the implantable pulse generator 18 is provided through the application of a low frequency (e.g., 30 KHz to 300 KHz) RF magnetic field 100 applied by a skin or clothing mounted implant charger controller 102 placed over or near the implantable pulse generator (see FIGS. 22A and 22B). The implant charger controller 102 might use a separate RF magnetic coupling coil (charging coil) 104 which is placed and/or secured on the skin or clothing over the implantable pulse generator 18 and connected by cable to the implant charger controller 102 (circuitry and battery in a housing) that is worn on a belt or clipped to the clothing (see FIG. 22A). In an alternative application, it is anticipated that the user would wear the implant charger controller 102, including an internal RF magnetic coupling coil (charging coil) 104, over the implantable pulse generator 18 to recharge the implantable pulse generator 18 (see FIG. 22B). The implant charger controller 102 allows the patient the freedom to move about and continue with most normal daily activities while recharging the implantable pulse generator.

The charging coil 104 preferably includes a predetermined construction, e.g., desirably 150 to 250 turns, and more desirably 200 turns of six strands of #36 enameled magnetic wire (all six strands being wound next to each other and electrically connected in parallel), or the like. Additionally, the charging coil outside diameter is in a range of about 40 millimeters to about 70 millimeters, and desirably about 65 millimeters, although the diameter may vary. The thickness of the charging coil 104 as measured perpendicular to the mounting plane is to be significantly less than the diameter, e.g., about three millimeters to about eleven millimeters, so as to allow the coil to be embedded or laminated in a sheet to facilitate placement on or near the skin. Such a construction will allow for efficient power transfer and will allow the charging coil 104 to maintain a temperature at or below about 41 degrees Celsius.

The implant charger controller 102 preferably includes its own internal batteries which may be recharged from the power mains, for example. A power adapter 106 may be included to provide for convenient recharging of the system's operative components, including the implant charger controller and the implant charger controller's internal batteries (see FIG. 22C). The implant charger controller 102 may not be used to recharge the implantable pulse generator 18 while plugged into the power mains.

Desirably, the implantable pulse generator 18 may be recharged while it is operating and the outer surface of the case 20 will not increase in temperature by more than two degrees Celsius above the surrounding tissue during the recharging. It is desirable that for most applications the recharging of the fully discharged battery 34 requires not more than six hours, and a recharging would be required between once per month to once per week depending upon the power requirements of the stimulus regime used.

c. Wireless Telemetry

According to one desirable technical feature, the assembly or system 10 includes an implantable pulse generator 18, which desirably incorporates wireless telemetry (rather that an inductively coupled telemetry) for a variety of functions able to be performed within arm's reach of the patient, the functions including receipt of programming and clinical (e.g., stimulus) parameters and settings from the clinical programmer 108, communicating usage history and battery status to the clinical programmer, providing user control of the implantable pulse generator 18, and for controlling the RF magnetic field 100 generated by the implant charger controller 102.

Each implantable pulse generator may also have a unique signature, (e.g., a serial number, which may include a model and/or series number, stored in non-volatile memory), that limits communication (secure communications) to only the dedicated controllers (e.g., the matched implant charger controller 102, patient controller 114, or a clinical programmer 108 configured with the serial number for the implantable pulse generator in question). The clinical programmer may be configured for use (i.e., wireless telemetry) with many patients by configuring the clinical programmer with a desired serial number to select a specific implantable pulse generator.

Figure 24:
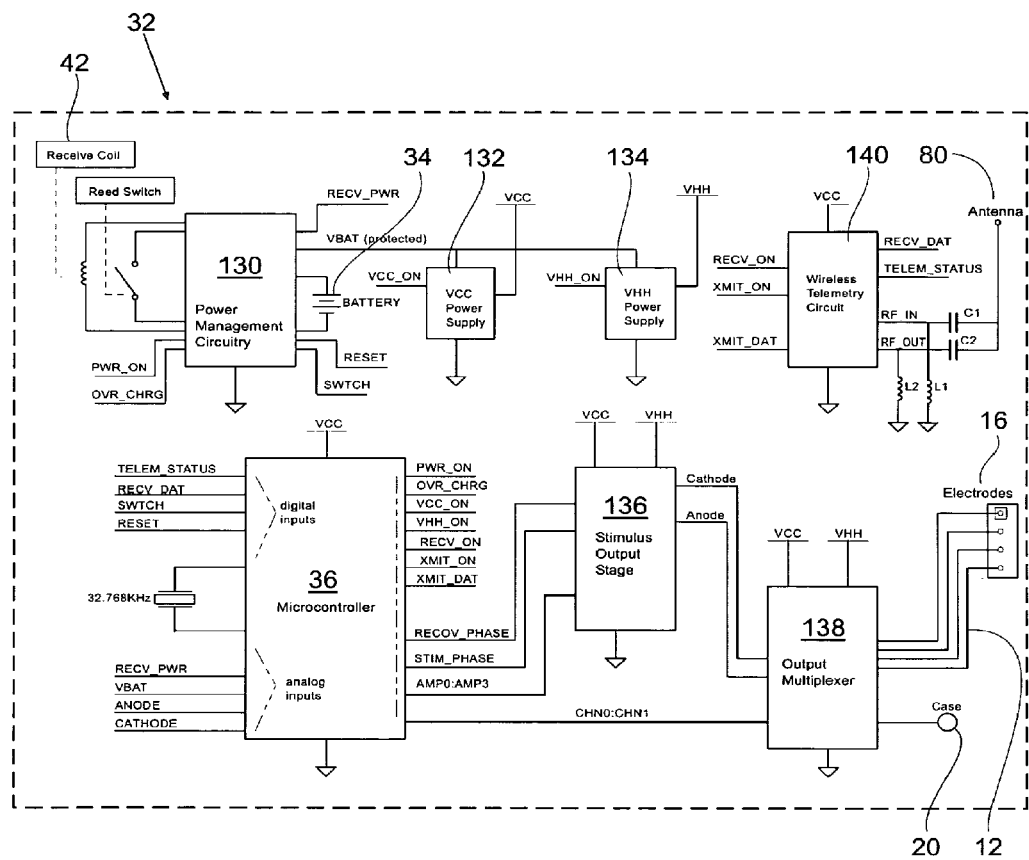
FIG. 24 is a block diagram of a circuit that the implantable pulse generator shown in FIGS. 3A and 3B may utilize.

The implantable pulse generator 18 desirably incorporates wireless telemetry as an element of the implantable pulse generator circuit 32 shown in FIG. 24. A circuit diagram showing a desired configuration for the wireless telemetry feature is shown in FIG. 26A. It is to be appreciated that modifications to this circuit diagram configuration which produce the same or similar functions as described are within the scope of the invention.

Figure 23A:
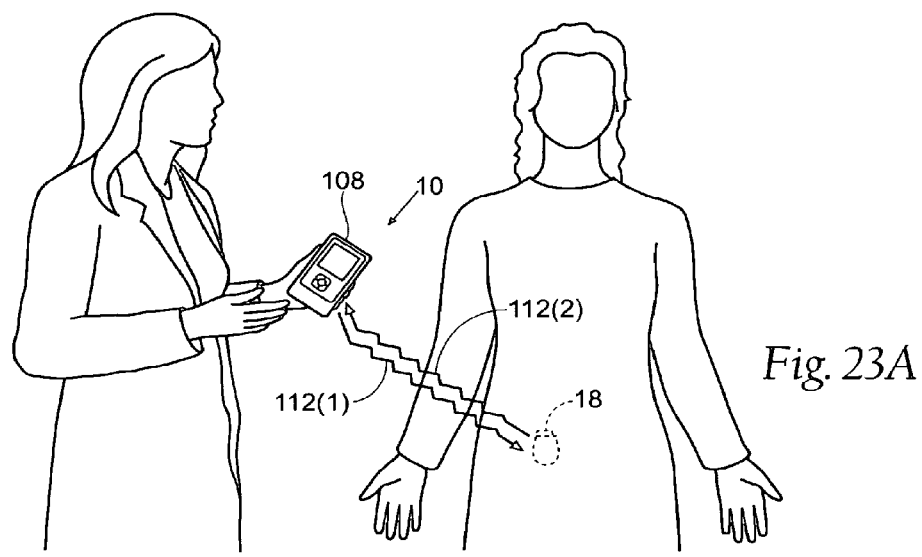
FIG. 23A is an anatomic view showing the implantable pulse generator shown in FIGS. 3A through 3D in association with a clinical programmer that relies upon wireless telemetry, and showing the programmer's capability of communicating with the implantable pulse generator up to an arm's length away from the implantable pulse generator.

As shown in FIG. 23A, the system 10 desirably includes an external controller, such as the clinical programmer 108 that, through a wireless telemetry 112, transfers commands, data, and programs into the implantable pulse generator 18 and retrieves status and data out of the implantable pulse generator 18. In some configurations, the clinical programmer may communicate with more than one implantable pulse generator implanted in the same user. Timing constraints imposed on the external controller and the implantable pulse generator 18 prevents two or more implantable pulse generators or two or more external controllers from communicating at nearly the same time. This eliminates the possibility that a response from one implantable pulse generator will be misinterpreted as the response from another implantable pulse generator.

The clinical programmer 108 initiates the wireless telemetry communication 112(1) to the implantable pulse generator 18, the communication including the implantable pulse generator's unique serial number and data elements that indicate the communication is a command from an external controller, e.g., data elements in a packet header. Only the implantable pulse generator 18 having the unique serial number responds 112(2) to the clinical programmer's communication. The communication response 112(2) includes data elements that indicate the communication is a response to a command from an external controller, and not a command from an external controller.

An external controller such as the clinical programmer 108 may also include provisions to seek out implantable pulse generators within communication range without knowing a unique serial number. To accomplish this, the clinical programmer may search for a range of serial numbers, such as 1 to 1000, as a non-limiting example.

The clinical programmer 108 may incorporate a custom programmed general purpose digital device; e.g., a custom program, industry standard handheld computing platform or other personal digital assistant (PDA). The clinical programmer 108 can also include an on-board microcontroller powered by a rechargeable battery. The rechargeable battery of the clinical programmer 108 may be recharged when connected via a cable to the print/backup station 110, or docked on the docking station 107 (a combined print/backup station and recharge cradle)(see FIG. 1). In addition to recharging the battery of the clinical programmer, the docking station 107 and/or the print/backup station 110 may also provide backup, retrieve, and print features. The docking station 107 and/or the print/backup station 110 may include memory space to allow the clinical programmer to download or upload (via wireless communication, a cable, and/or a portable memory device) any and all information stored on the clinical programmer 108 (backup and retrieve feature), and also allow the information from the clinical programmer 108 to be printed in a desired format (print feature).

Figure 22C:
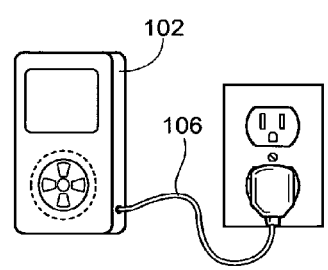
FIG. 22C is a perspective view of the implant charger controller of the type shown in FIGS. 22A and 22B, with the charger shown connected to the power mains to recharge the power supply within the implant charger controller.

In addition, the rechargeable battery of the clinical programmer 108 may be recharged in the same or similar manner as described and shown in FIG. 22C for the implant charger controller 102, i.e., connected to the power mains with a power adapter 106 (see FIG. 1); or the custom electronics of the clinical programmer 108 may receive power from the connected pocket PC or PDA.

Figure 23B:
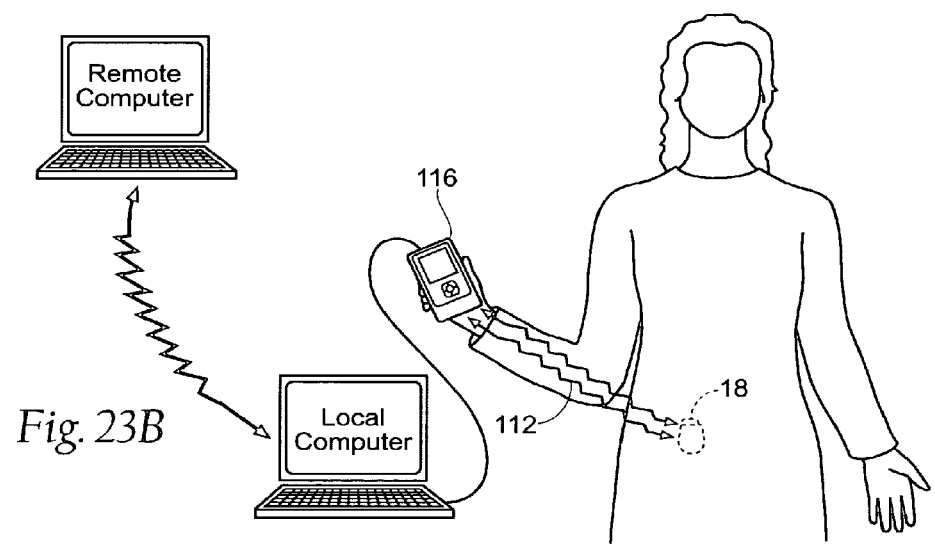
FIG. 23B is a system view of an implantable pulse generator system incorporating a network interface and showing the system's capability of communicating and transferring data over a network, including a remote network.

The microcontroller carries embedded code which may include pre-programmed rules or algorithms that allow a clinician to remotely download program stimulus parameters and stimulus sequences parameters into the implantable pulse generator 18. The microcontroller of the clinical programmer 108 is also desirably able to interrogate the implantable pulse generator and upload usage data from the implantable pulse generator. FIG. 23A shows one possible application where the clinician is using the programmer 108 to interrogate the implantable pulse generator. FIG. 23B shows an alternative application where the clinical programmer, or a network interface 116 intended for remote programming applications and having the same or similar functionality as the clinical programmer 108 or the implant charger controller 102, is used to interrogate the implantable pulse generator. As can be seen, the network interface 116 is connected to a local computer, allowing for remote interrogation via a local area network, wide area network, or Internet connection, for example.

Using subsets of the clinical programmer software, features of the clinical programmer 108 or network interface 116 may also include the ability for the clinician or physician to remotely monitor and adjust parameters using the Internet or other known or future developed networking schemes. The network interface 116 would desirably connect to the patient's computer in their home through an industry standard network such as the Universal Serial Bus (USB), where in turn an applet downloaded from the clinician's server would contain the necessary code to establish a reliable transport level connection between the implantable pulse generator 18 and the clinician's client software, using the network interface 116 as a bridge. Such a connection may also be established through separately installed software. The clinician or physician could then view relevant diagnostic information, such as the health of the unit or its current settings, and then modify the stimulus settings in the implantable pulse generator or direct the patient to take the appropriate action. Such a feature would save the clinician, the patient and the health care system substantial time and money by reducing the number of office visits during the life of the implant.

Other features of the clinical programmer, based on an industry standard platform, such as personal digital assistant (PDA) or pocket PC, might include the ability to connect to the clinician's computer system in his or hers office. Such features may take advantage of the PDA system software for network communications. Such a connection then would transfer relevant patient data to the host computer or server for electronic processing and archiving. With a feature as described here, the clinical programmer then becomes an integral link in an electronic chain that provides better patient service by reducing the amount of paperwork that the physician's office needs to process on each office visit. It also improves the reliability of the service since it reduces the chance of mis-entered or misplaced information, such as the record of the parameter setting adjusted during the visit.

With the use of either the implant charger controller 102, or a patient controller 114 (see FIG. 23C), the wireless link 112 allows a patient to control certain predefined parameters of the implantable pulse generator within a predefined limited range. The parameters may include the operating modes/states, increasing/decreasing or optimizing stimulus patterns, or providing open or closed loop feedback from an external sensor or control source. The wireless telemetry 112 also desirably allows the user to interrogate the implantable pulse generator 18 as to the status of its internal battery 34. The full ranges within which these parameters may be adjusted by the user are controlled, adjusted, and limited by a clinician, so the user may not be allowed the full range of possible adjustments.

Figure 23C:
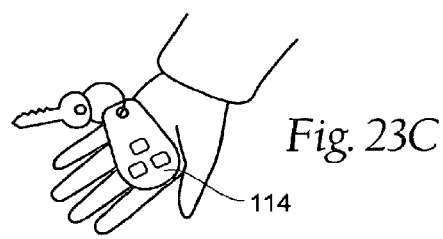
FIG. 23C is a graphical view of one possible type of patient controller that may be used with the implantable pulse generator shown in FIGS. 3A through 3D.

In one embodiment, the patient controller 114 is sized and configured to couple to a key chain, as seen in FIG. 23C. It is to be appreciated that the patient controller 114 may take on any convenient shape, such as a ring on a finger, or a watch on a wrist, or an attachment to a belt, for example. It may also be desirable to separate the functions of the implant charger controller 102 into a charger and a patient controller.

The wireless telemetry may incorporate a suitable, low power wireless telemetry transceiver (radio) chip set that can operate in the MICS (Medical Implant Communications Service) band (402 MHz to 405 MHz) or other VHF/UHF low power, unlicensed bands. A wireless telemetry link not only makes the task of communicating with the implantable pulse generator 18 easier, but it also makes the link suitable for use in motor control applications where the user issues a command to the implantable pulse generator to produce muscle contractions to achieve a functional goal (e.g., to stimulate ankle flexion to aid in the gait of an individual after a stroke) without requiring a coil or other component taped or placed on the skin over the implanted implantable pulse generator.

Appropriate use of power management techniques is important to the effective use of wireless telemetry. Desirably, the implantable pulse generator is exclusively the communications slave, with all communications initiated by the external controller (the communications master). The receiver chip of the implantable pulse generator is OFF about 99% or more of the time and is pulsed on periodically to search for a command from an external controller, including but not limited to the clinical programmer 108, the patient controller 114, the network interface 116, and the implant charger controller 102. When the implantable pulse generator 18 operates at a low rate of wireless telemetry because of a low battery, the transceiver chip may be pulsed on less frequently, such as about every five seconds to about ten seconds, to search for a command from an external controller.

Communications protocols include appropriate received message integrity testing and message acknowledgment handshaking to assure the necessary accuracy and completeness of every message. Some operations (such as reprogramming or changing stimulus parameters) require rigorous message accuracy testing and acknowledgement. Other operations, such as a single user command value in a string of many consecutive values, might require less rigorous checking and no acknowledgement or a more loosely coupled acknowledgement.

The timing with which the implantable pulse generator enables its transceiver to search for RF telemetry from an external controller is precisely controlled (using a time base established by a quartz crystal) at a relatively low rate, e.g., the implantable pulse generator may look for commands from the external controller for about two milliseconds at a rate of two (2) Hz or less. This equates to a monitoring interval of about ½ second or less. It is to be appreciated that implantable pulse generator's enabled transceiver rate and the monitoring rate may vary faster or slower depending on the application. This precise timing allows the external controller to synchronize its next command with the time that the implantable pulse generator will be listening for commands. This, in turn, allows commands issued within a short time (seconds to minutes) of the last command to be captured and acted upon without having to 'broadcast' an idle or pause signal for a full received monitoring interval before actually issuing the command in order to know that the implantable pulse generator will have enabled its receiver and be ready to receive the command. Similarly, the communications sequence is configured to have the external controller issue commands in synchronization with the implantable pulse generator listening for commands. Similarly, the command set implemented is selected to minimize the number of messages necessary and the length of each message consistent with the appropriate level of error detection and message integrity monitoring. It is to be appreciated that the monitoring rate and level of message integrity monitoring may vary faster or slower depending on the application, and may vary over time within a given application.

A suitable radio chip is used for the half duplex wireless communications, e.g., the AMIS-52100 (AMI Semiconductor; Pocatello, Id.). This transceiver chip is designed specifically for the MICS and its European counter-part the ULP-AMI (Ultra Low Power-Active Medical Implant) band. This chip set is optimized by micro-power operation with rapid start-up, and RF 'sniffing' circuitry.

The implant charger controller 102 and the implantable pulse generator 18, as shown in FIGS. 22A and 22B may also use wireless telemetry to provide a "smart charge" feature to indicate that charging is occurring and to make corrections to allow for optimal recharging and protect against overcharging. During a battery recharge period, the smart charge causes the implant charger controller 102 to issue commands to the implantable pulse generator 18 at timed intervals, e.g., every thirty seconds, to instruct the implantable pulse generator to confirm that the generated RF magnetic field is being received and is adequate for recharging the rechargeable battery. If the implant charger controller 102 does not receive a response from the implantable pulse generator 18 to confirm that the generated RF magnetic field is being received, the implant charger controller may stop generating the RF magnetic field.

During the battery recharge period, the implantable pulse generator 18 will transmit status information, e.g., an indication of the battery 34 charge status and an indication of the magnitude of power recovered by the receive coil 42, back to the implant charger controller 102.

Based on the magnitude of the power recovered, the smart charge allows the implant charger controller 102 to automatically adjust up or down the magnitude of the magnetic field 100 and/or to instruct the user to reposition the charging coil 104 based on the status information to allow optimal recharging of the implantable pulse generator battery 34 while minimizing unnecessary power consumption by the implant charger controller 102 and power dissipation in the implantable pulse generator 18 (through circuit losses and/or through absorption by the implantable pulse generator case 20 and other components). The magnitude of the RF magnetic field 100 may be automatically adjusted up to about 300 percent or more of the initial magnitude of the RF magnetic field and adjusted down until the implant charger controller stops generating the RF magnetic field.

The instructions to the user to reposition the charging coil 104 may be a visual instruction, such as a bar graph on the implant charger controller 102, or a display on the implant charger controller showing relative positions of the charging coil 104 and the implantable pulse generator 18, or an audio instruction, such as a varying tone to indicate relative position, or a combination of instructions.

The smart charge allows for the outer surface of the case 20 of the implantable pulse generator 18 to maintain a two degree Celsius or less temperature rise during the time period in which the receive coil 42 is transcutaneously receiving externally generated power, i.e., RF magnetic field.

In cases where two implant charger controllers 102 could be erroneously swapped, or where two or more implantable pulse generators 18 may be within wireless telemetry range of each other, e.g., when two users live in the same home, a first implantable pulse generator 18 could communicate with its implant charger controller 102 even when the charging coil 104 is erroneously positioned over another implantable pulse generator 18. The implant charger controller 102 is configured to communicate and charge a specifically identified implantable pulse generator (identified by the unique signature/serial number). Because the first implantable pulse generator, the one communicating with the implant charger controller 102, does not sense the RF magnetic charging field 100 when the charging coil 104 is positioned over another implantable pulse generator, the first implantable pulse generator communicates with the implant charger controller 102 to increase the magnitude of the RF magnetic field 100. This communication may continue until the magnitude of the RF magnetic field is at its maximum.

In order to stop an implant charger controller 102 from attempting to charge the incorrect implantable pulse generator 18, the implant charger controller periodically decreases the magnitude of the RF magnetic field 100 and communicates with its (identified by the unique signature/serial number) implantable pulse generator to confirm/determine that the implantable pulse generator 18 sensed the decrease in the magnitude. If the charging coil is erroneously positioned over another implantable pulse generator 18, the correct implantable pulse generator will not sense the decrease and will indicate to the implant charger controller 102 that it did not sense the decrease. The implant charger controller 102 will then restore the original RF magnetic field strength and retry the reduced RF magnetic field test. Multiple failures of the test will cause the implant charger controller 102 to suspend charging and notify the user of the error. Similarly, should the implanted pulse generator not recover usable power from the RF magnetic field 100 after a few minutes, the implant charger controller 102 will suspend charging and notify the user of the error.

d. Stimulus Output Stage

According to one desirable technical feature, the implantable pulse generator 18 desirably uses a single stimulus output stage 136 (generator) that is directed to one or more output channels (electrode surfaces) by analog switch(es) or analog multiplexer(s). Desirably, the implantable pulse generator 18 will deliver at least one channel of stimulation via a lead/electrode. For applications requiring more stimulus channels, several channels (perhaps up to four) can be generated by a single output stage. In turn, two or more output stages could be used, each with separate multiplexing to multiple channels, to allow an implantable pulse generator with eight or more stimulus channels. As a representative example, the stimulation desirably has a biphasic waveform (net DC current less than 10 microAmps), adjustable from about 0.5 mA to about 20 mA based on electrode type and the tissue type being stimulated, and pulse durations adjustable from about 5 microseconds or less up to 500 microseconds or more. The stimulus current (amplitude) and pulse duration being programmable on a channel to channel basis and adjustable over time based on a clinically programmed sequence or regime or based on user (patient) commands received via the wireless communications link.

Figure 27:
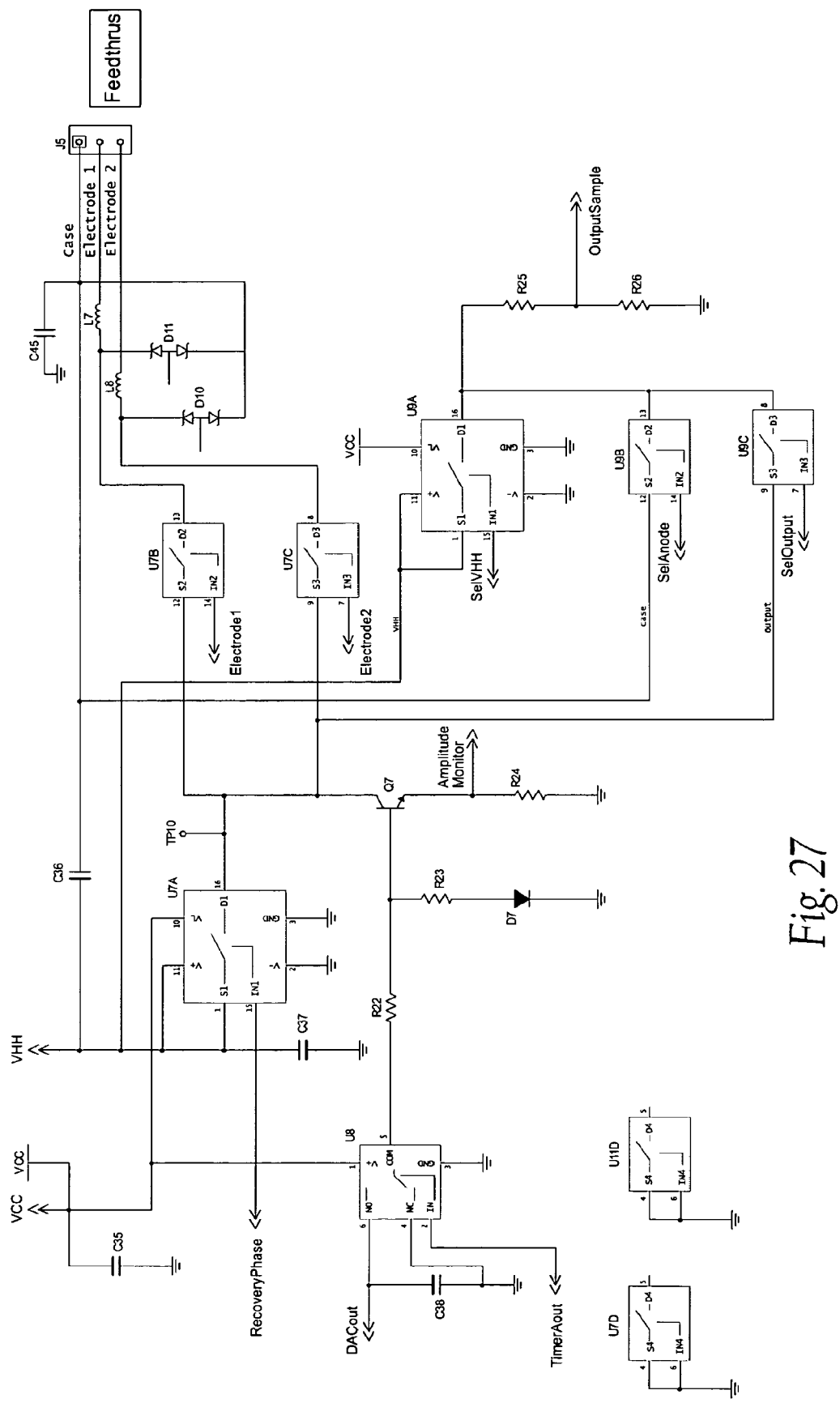
FIG. 27 is a circuit diagram showing a possible circuit for the stimulus output stage and output multiplexing features used with the implantable pulse generator shown in FIGS. 3A through 3D.

A circuit diagram showing a desired configuration for the stimulus output stage feature is shown in FIG. 27. It is to be appreciated that modifications to this circuit diagram configuration which produce the same or similar functions as described are within the scope of the invention.

For neuromodulation/central nervous system applications, the implantable pulse generator 18 may have the capability of applying stimulation twenty-four hours per day. A typical stimulus regime for such applications might have a constant stimulus phase, a no stimulus phase, and ramping of stimulus levels between these phases. For Functional Electrical Stimulation (FES), the intensity and timing of the stimulation may vary with user inputs via switches or sensors.

Figure 28:
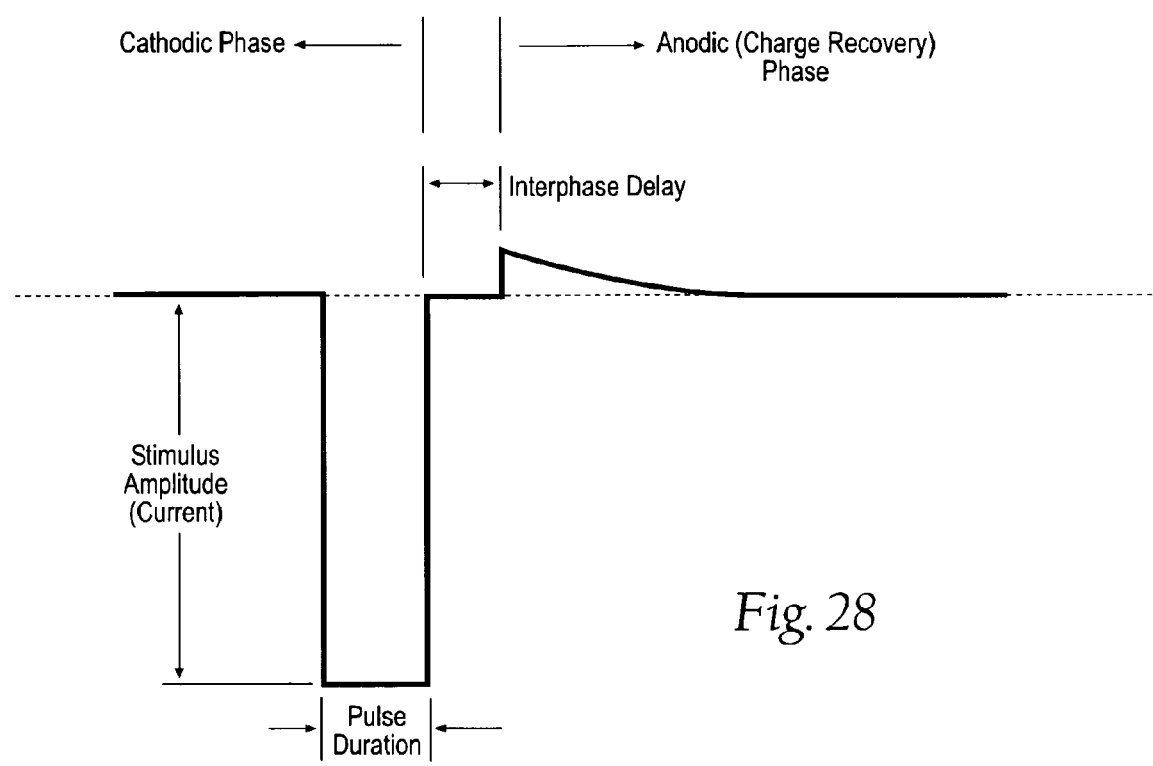
FIG. 28 is a graphical view of a desirable biphasic stimulus pulse output of the implantable pulse generator for use with the system shown in FIG. 1.

Desirably, the implantable pulse generator 18 includes a single stimulus generator (with its associated DC current blocking output capacitor) which is multiplexed to a number of output channels; or a small number of such stimulus generators each being multiplexed to a number of output channels. This circuit architecture allows multiple output channels with very little additional circuitry. A typical, biphasic stimulus pulse is shown in FIG. 28. Note that the stimulus output stage circuitry 136 may incorporate a mechanism to limit the recovery phase current to a small value (perhaps 0.5 mA). Also note that the stimulus generator (and the associated timing of control signals generated by the microcontroller) may provide a delay (typically of the order of 100 microseconds) between the cathodic phase and the recovery phase to limit the recovery phase diminution of the cathodic phase effective at eliciting a neural excitation. The charge recovery phase for any electrode (cathode) must be long enough to assure that all of the charge delivered in the cathodic phase has been returned in the recovery phase, e.g., greater than or equal to five time constants are allowed for the recovery phase. This will allow the stimulus stage to be used for the next electrode while assuring there is no net DC current transfer to any electrode. Thus, the single stimulus generator having this characteristic would be limited to four channels (electrodes), each with a maximum frequency of 30 Hz to 50 Hz. This operating frequency exceeds the needs of many indications for which the implantable pulse generator is well suited. For applications requiring more channels (or higher composite operating frequencies), two or more separate output stages might each be multiplexed to multiple (e.g., four) electrodes. Alternatively, the output multiplexer/switch stage might allow each output channel to have its own output coupling capacitor.

e. The Lead Connection Header

According to one desirable technical feature, the implantable pulse generator 18 desirably includes a lead connection header 26 for connecting the lead(s) 12 that will enable reliable and easy replacement of the lead/electrode (see FIGS. 3A and 3B), and includes a small antenna 80 for use with the wireless telemetry feature.

The implantable pulse generator desirably incorporates a connection header (top header) 26 having a conventional connector 82 that is easy to use, reliable, and robust enough to allow multiple replacements of the implantable pulse generator after many years (e.g., more than ten years) of use. The surgical complexity of replacing an implantable pulse generator is usually low compared to the surgical complexity of correctly placing the implantable lead 12/electrode 16 in proximity to the target nerve/tissue and routing the lead 12 to the implantable pulse generator. Accordingly, the lead 12 and electrode 16 desirably has a service life of at least ten years with a probable service life of fifteen years or more. Based on the clinical application, the implantable pulse generator may not have this long a service life. The implantable pulse generator service life is largely determined by the power capacity of the Lithium Ion battery 34, and is likely to be three to ten years, based on the usage of the device. Desirably, the implantable pulse generator 18 has a service life of at least five years.

As described above, the implantable pulse generator preferably will use a laser welded titanium case. As with other active implantable medical devices using this construction, the implantable lead(s) 12 connect to the implantable pulse generator through the molded or cast polymeric connection header 26. Metal-ceramic or metal-glass feed-thrus 44, 46, 48 (see FIGS. 7 and 16), maintain the hermetic seal of the titanium capsule while providing electrical contact to the electrical contacts of the lead 12/electrode 16.

The standard implantable connectors may be similar in design and construction to the low-profile IS-1 connector system (per ISO 5841-3). The IS-1 connectors have been in use since the late 1980s and have been shown to be reliable and provide easy release and re-connection over several implantable pulse generator replacements during the service life of a single pacing lead. Full compatibility with the IS-1 standard, and mating with pacemaker leads, is not a requirement for the implantable pulse generator.

The implantable pulse generator connection system may include a modification of the conventional IS-1 connector system, which shrinks the axial length dimensions or adds a third or more electrical contact "rings" or "bands" while keeping the general format and radial dimensions of the IS-1. For application with more than two electrode conductors, the top header 26 may incorporate one or more connection receptacles each of which accommodate leads with typically four conductors. When two or more leads are accommodated by the header, these lead may exit the connection header in the same or opposite directions (i.e., from opposite sides of the header).

These connectors can be similar to the banded axial connectors used by other multi-polar implantable pulse generators or may follow the guidance of the draft IS-4 implantable connector standard. The design of the implantable pulse generator case 20 and header 26 preferably includes provisions for adding the additional feed-thrus and larger headers for such indications.

The inclusion of the UHF antenna 80 for the wireless telemetry inside the connection header 26 is necessary as the shielding offered by the titanium case will severely limit (effectively eliminate) radio wave propagation through the case. The antenna 80 connection will be made through feed-thru 48 similar to that used for the electrode connections 44, 46. Alternatively, the wireless telemetry signal may be coupled inside the implantable pulse generator onto a stimulus output channel and coupled to the antenna 80 with passive filtering/coupling elements/methods in the connection header 26.

f. The Microcontroller

According to one desirable technical feature, the implantable pulse generator 18 desirably uses a standard, commercially available micro-power, flash (in-circuit programmable) programmable microcontroller 36 or processor core in an application specific integrated circuit (ASIC). This device (or possibly more than one such device for a computationally complex application with sensor input processing) and other large semiconductor components may have custom packaging such as chip-on-board, solder flip chip, or adhesive flip chip to reduce circuit board real estate needs.

Figure 29:
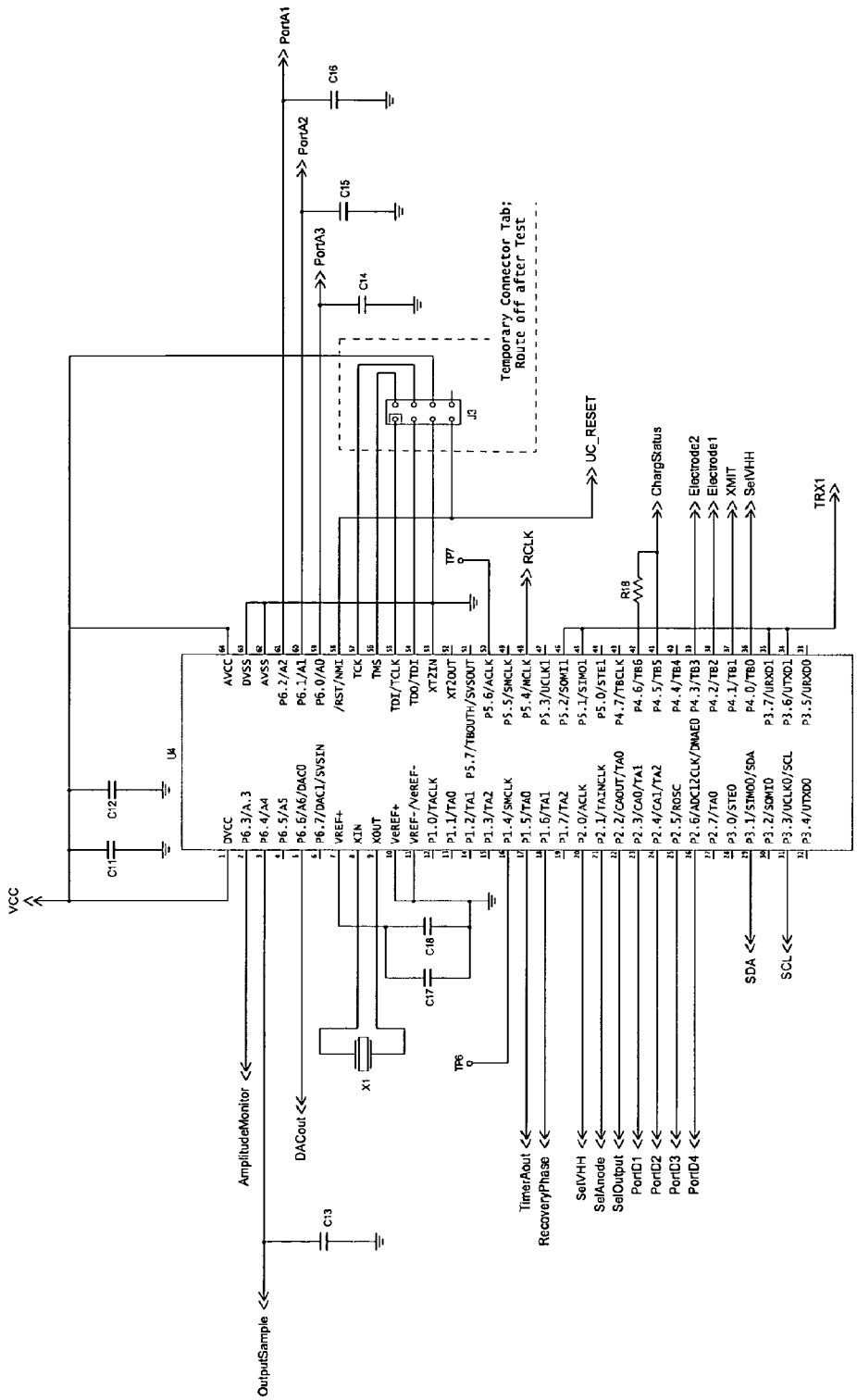
FIG. 29 is a circuit diagram showing a possible circuit for the microcontroller used with the implantable pulse generator shown in FIGS. 3A through 3D.

A circuit diagram showing a desired configuration for the microcontroller 36 is shown in FIG. 29. It is to be appreciated that modifications to this circuit diagram configuration which produce the same or similar functions as described are within the scope of the invention.

g. Power Management Circuitry

Figure 30:
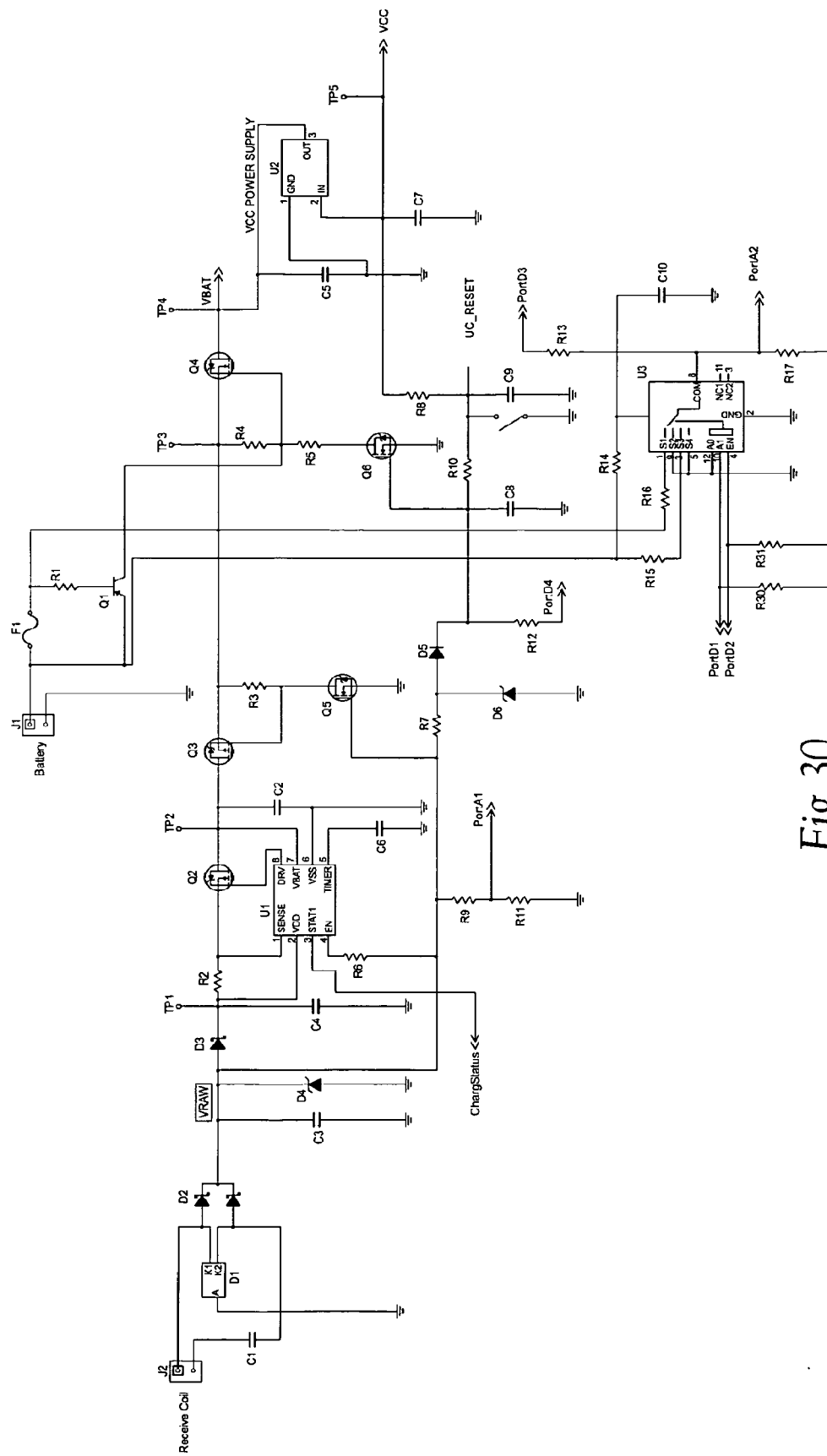
FIG. 30 is a circuit diagram showing one possible option for a power management sub-circuit where the sub-circuit includes MOSFET isolation between the battery and charger circuit, the power management sub-circuit being a part of the implantable pulse generator circuit shown in FIG. 24.
Figure 31:
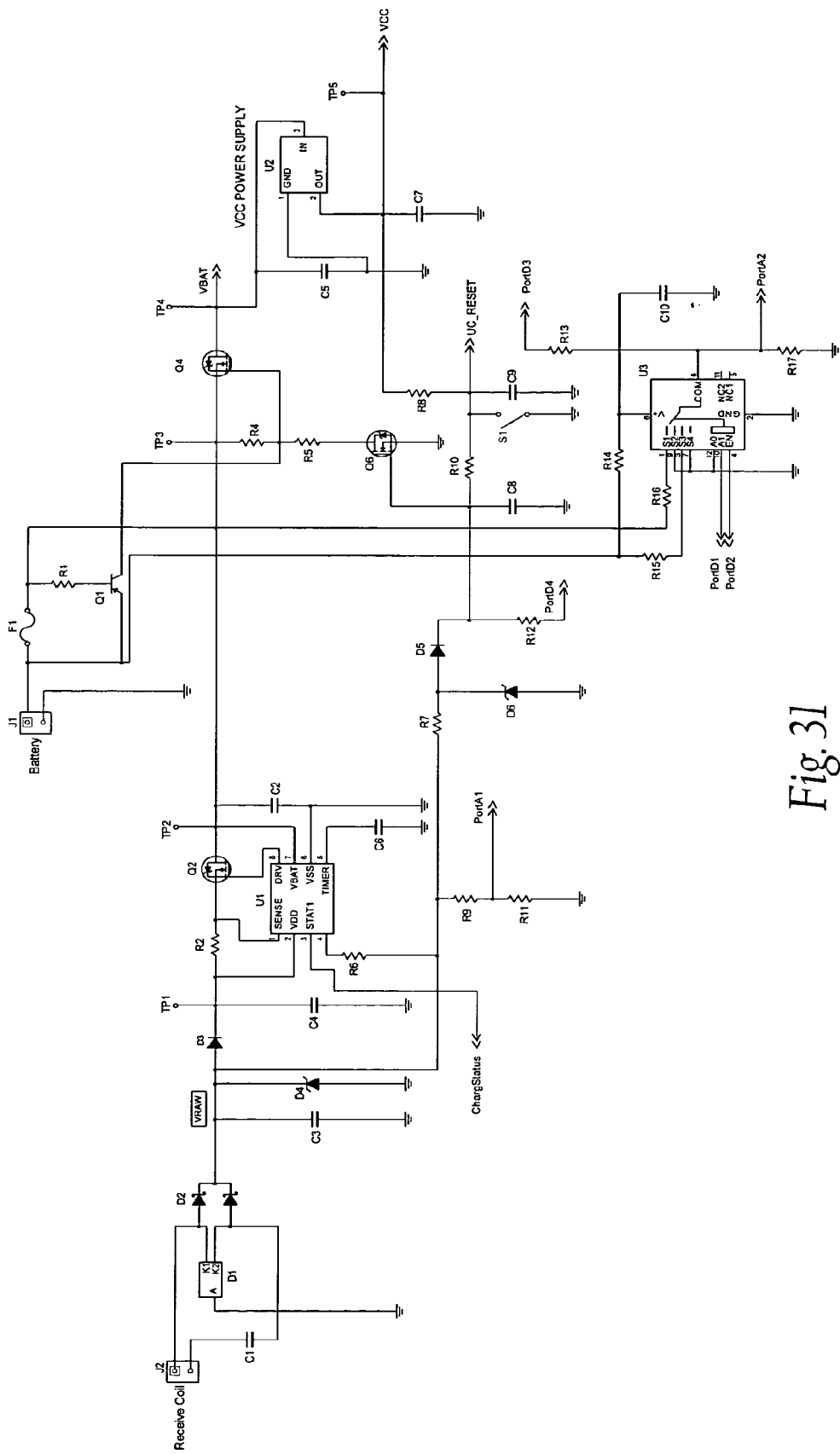
FIG. 31 is a circuit diagram showing a second possible option for a power management sub-circuit where the sub-circuit does not include MOSFET isolation between the battery and charger circuit, the power management sub-circuit being a part of the implantable pulse generator circuit shown in FIG. 24.

According to one desirable technical feature, the implantable pulse generator 18 desirably includes efficient power management circuitry as an element of the implantable pulse generator circuitry 32 shown in FIG. 24. The power management circuitry is generally responsible for the efficient distribution of power and monitoring the battery 34, and for the recovery of power from the RF magnetic field 100 and for charging and monitoring the battery 34. In addition, the operation of the implantable pulse generator 18 can be described in terms of having operating modes as relating to the function of the power management circuitry. These modes may include, but are not limited to IPG Active, IPG Dormant, and, IPG Active and Charging. These modes will be described below in terms of the principles of operation of the power management circuitry using possible circuit diagrams shown in FIGS. 30 and 31. FIG. 30 shows one possible power management sub-circuit having MOSFET isolation between the battery 34 and the charger circuit. FIG. 31 shows another possible power management sub-circuit diagram without having MOSFET isolation between the battery 34 and the charger circuit. In the circuit without the isolation MOSFET (see FIG. 31), the leakage current of the disabled charge control integrated circuit chip (U1) must be very low to prevent this leakage current from discharging the battery 34 in all modes (including the Dormant mode). Except as noted, the description of these modes applies to both circuits.

i. IPG Active Mode

The IPG Active mode occurs when the implantable pulse generator 18 is operating normally. In this mode, the implantable pulse generator may be generating stimulus outputs or it may be waiting to generate stimulus in response to a timed neuromodulation sequence or a telemetry command from an external controller. In this mode, the implantable pulse generator is active (microcontroller 36 is powered and coordinating wireless communications and may be timing & controlling the generation and delivery of stimulus pulses).

i(a) Principles of Operation, IPG Active Mode

In the IPG Active mode, the lack of a RF magnetic field from a charging coil means there will be no DC current from VRAW, which means that Q5 is held off (see FIG. 30). This, in turn, holds Q3 off and a portion of the power management circuitry is isolated from the battery 34. In FIG. 31, the lack of DC current from VRAW means that U1 is disabled either directly or via the microcontroller. This, in turn, keeps the current drain from the battery 34 to an acceptably low level, typically less than one microAmp.

ii. IPG Dormant Mode

The IPG Dormant mode occurs when the implantable pulse generator 18 is completely disabled (powered down). In this mode, power is not being supplied to the microcontroller 36 or other enabled circuitry. This is the mode for the long-term storage of the implantable pulse generator before or after implantation. As a safety feature, the Dormant mode may also be entered by placing a pacemaker magnet 118 (or comparable device) over the implantable pulse generator 18 for a predetermined amount of time, e.g., five seconds. The implantable pulse generator 18 may also be put in the Dormant mode by a wireless telemetry command from an external controller.

The Dormant mode may be exited by placing the implantable pulse generator 18 into the Active and Charging mode by placing the charging coil 104 of a functional implant charger controller 102 in close proximity to the implantable pulse generator 18.

ii(a) Principles of Operation, IPG Dormant Mode

In the IPG Dormant mode, VBAT is not delivered to the remainder of the implantable pulse generator circuitry because Q4 is turned off. The Dormant mode is stable because the lack of VBAT means that VCC is also not present, and thus Q6 is not held on through R8 and R10. Thus the battery 34 is completely isolated from all load circuitry (the VCC power supply and the VHH power supply).

The Dormant mode may be entered through the application of the magnet 118 placement over S1 (magnetic reed switch) or through the reception of a command by the wireless telemetry. In the case of the telemetry command, the PortD4, which is normally configured as a microcontroller input, is configured as a logic output with a logic low (0) value. This, in turn, discharges C8 through R12 and turns off Q6; which, in turn, turns off Q4 and forces the implantable pulse generator into the Dormant mode. Note that R12 is much smaller in value than R10, thus the microcontroller 36 can force C8 to discharge even though VCC is still present.

Figure 13:
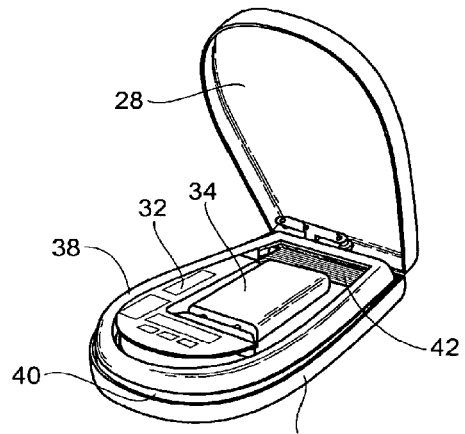

In FIG. 30, the lack of DC current from VRAW means that Q5 is held off. This, in turn, holds Q3 off and a portion of the power management circuitry is isolated from the battery 34. Also, Q4 was turned off. In FIG. 13, the lack of DC current from VRAW means that U1 is disabled. This, in turn, keeps the current drain from the battery 34 to an acceptably low level, typically less than 1 µA.

iii. IPG Active and Charging Mode

In the embodiment having a rechargeable battery, the implantable pulse generator Active and Charging mode occurs when the implantable pulse generator 18 is being charged. In this mode, the implantable pulse generator 18 is active, i.e., the microcontroller 36 is powered and coordinating wireless communications and may be timing and controlling the generation and delivery of stimulus pulses. The implantable pulse generator 18 may use the smart charge feature to communicate with the implant charger controller 102 concerning the magnitude of the battery voltage and the DC voltage recovered from the RF magnetic field 100. The implant charger controller 102 uses this data for two purposes: to provide feedback to the user about the proximity of the charging coil 104 to the implanted pulse generator, and to increase or decrease the strength of the RF magnetic field 100. This, in turn, minimizes the power losses and undesirable heating of the implantable pulse generator.

While in the IPG Active and Charging mode, the power management circuitry 130 serves the following primary functions:

(1) provides battery power to the rest of the implantable pulse generator circuitry 32, (2) recovers power from the RF magnetic field 100 generated by the implant charger controller 102, (3) provides controlled charging current (from the recovered power) to the battery 34, and (4) communicates with the implant charger controller 102 via the wireless telemetry link 112 to provide feedback to the user positioning the charging coil 104 over the implantable pulse generator 18, and to cause the implant charger controller 102 to increase or decrease the strength of its RF magnetic field 100 for optimal charging of the implantable pulse generator battery 34 (Lithium Ion battery).

iii(a) Principles of Operation, IPG Active and Charging Mode iii(a)(1) RF voltage is induced in the receive coil 42 by the RF magnetic field 100 of the implant charger controller 102 iii(a)(2) Capacitor C1 is in series with the receive coil and is selected to introduce a capacitive reactance that compensates (subtracts) the inductive reactance of the receive coil 42 iii(a)(3) D1-D2 form a full wave rectifier that converts the AC voltage recovered by the receive coil 42 into a pulsating DC current flow iii(a)(4) This pulsating DC current is smoothed (filtered) by C3 (this filtered DC voltage is labeled VRAW)

iii(a)(5) D4 is a zener diode that acts as a voltage limiting device (in normal operation, D4 is not conducting significant current)

iii(a)(6) D3 prevents the flow of current from the battery 34 from preventing the correct operation of the power management circuitry 130 once the voltage recovered from the RF magnetic field is removed. Specifically, current flow from the battery [through Q3 (turned ON), in the case for the circuit of FIG. 30] through the body diode of Q2 would hold ON the charge controller IC (U1). This additional current drain would be present in all modes, including Dormant, and would seriously limit battery operating life. Additionally, this battery current pathway would keep Q6 turned ON even if the magnetic reed switch (S1) were closed; thus preventing the isolation of the implantable pulse generator circuitry from the battery in the Dormant mode.

iii(a)(7) U1, Q2, R2, C4, C6, and C2 form the battery charger sub-circuit

U1 is a micropower, Lithium Ion Charge Management Controller chip implementing a constant current phase and constant voltage phase charge regime. This chip desirably incorporates an internal voltage reference of high accuracy (+/−0.5%) to establish the constant voltage charge level. U1 performs the following functions:

monitors the voltage drop across a series resistor R2 (effectively the current charging the battery 34) to control the current delivered to the battery through the external pass transistor Q2. U1 uses this voltage across R2 to establish the current of the constant current phase (typically the battery capacity divided by five hours) and decreases the current charging the battery as required to limit the battery voltage and effectively transition from constant current phase to constant voltage phase as the battery voltage approaches the terminal voltage, iii(a)(8) U1 may also include provisions for timing the duration of the constant current and constant voltage phases and suspends the application of current to the battery 34 if too much time is spent in the phase. These fault timing features of U1 are not used in normal operation.

iii(a)(9) In this circuit, the constant voltage phase of the battery charging sequence is timed by the microcontroller 36 and not by U1. The microcontroller monitors the battery voltage and terminates the charging sequence (i.e., tells the implant charger controller 102 that the implantable pulse generator battery 34 is fully charged) after the battery voltage has been in the constant voltage region for greater than a fixed time period (e.g., 15 to 20 minutes).

iii(a)(10) In FIGS. 30, Q3 and Q5 are turned ON only when the charging power is present. This effectively isolates the charging circuit from the battery 34 when the externally supplied RF magnetic field 100 is not present and providing power to charge the rechargeable battery.

iii(a)(11) In FIG. 31, U1 is always connected to the battery 34, and the disabled current of this chip is a load on the battery 34 in all modes (including the Dormant mode). This, in turn, is a more demanding requirement on the current consumed by U1 while disabled.

iii(a)(12) F1 is a fuse that protects against long-duration, high current component failures. In most transient high current failures, (i.e., soft failures that cause the circuitry to consume high current levels and thus dissipate high power levels; but the failure initiating the high current flow is not permanent and the circuit will resume normal function if the circuit is removed from the power source before damage from overheating occurs), the VBAT circuitry will disconnect the battery 34 from the temporary high load without blowing the fuse. The specific sequence is:

High current flows into a component(s) powered by VBAT (most likely the VHH power supply or an element powered by the VCC power supply).

The voltage drop across the fuse will (prior to the fuse blowing) turn ON Q1 (based on the current flow through the fuse causing a 0.5V to 0.6V drop across the resistance of F1).

The collector current from Q1 will turn off Q4.

VBAT drops very quickly and, as a direct result, VCC falls. In turn, the voltage on the PortD4 IO pin from the microcontroller voltage falls as VCC falls, through the parasitic diodes in the microcontroller 36. This then pulls down the voltage across C6 as it is discharged through R12.

The implantable pulse generator 18 is now stable in the Dormant mode, i.e., VBAT is disconnected from the battery 34 by a turned OFF Q4. The only load remaining on the battery is presented by the leakage current of the charging circuit and by the analog multiplexer (switches) U3 that are used to direct an analog voltage to the microcontroller 36 for monitoring the voltage after the resistance of F1) an estimate of the current consumption of the entire circuit. A failure of these voltage monitoring circuits is not protected by the fuse, but resistance values limit the current flow to safe levels even in the event of component failures. A possible source of a transient high-current circuit failure is the SCR latchup or supply-to-ground short failure of a semiconductor device directly connected to VBAT or VCC.

iii(a)(13) R9 & R11 form a voltage divider to convert VRAW (0V to 8V) into the voltage range of the microcontroller's A-D inputs (used for closed loop control of the RF magnetic field strength), iii(a)(14) R8 and C9 form the usual R-C reset input circuit for the microcontroller 36; this circuit causes a hardware reset when the magnetic reed switch (S1) is closed by the application of a suitable static magnetic field for a short duration, iii(a)(15) R10 and C8 form a much slower time constant that allows the closure of the reed switch by the application of the static magnetic field for a long duration to force the implantable pulse generator 18 into the Dormant mode by turning OFF Q6 and thus turning OFF Q4. The use of the magnetic reed switch for resetting the microcontroller 36 or forcing a total implantable pulse generator shutdown (Dormant mode) may be a desirable safety feature.

2. Representative Implant Pulse

Generator Circuitry

Figure 25:
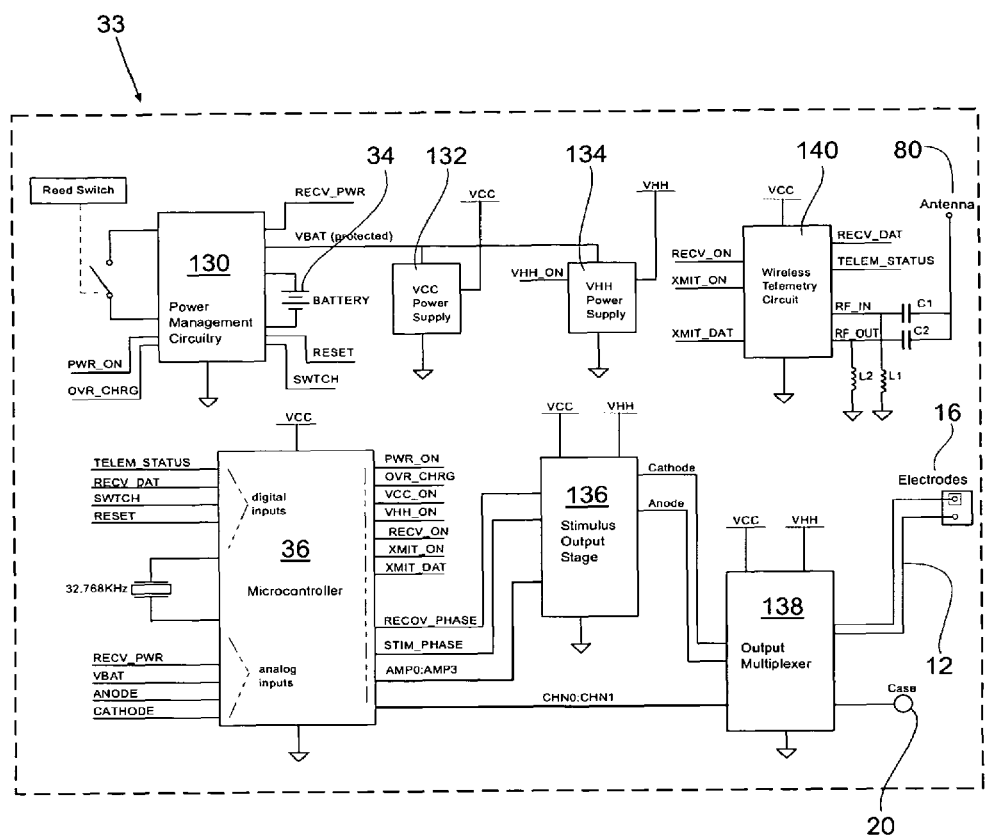
FIG. 25 is an alternative embodiment of the block diagram shown in FIG. 24, and shows a block circuit diagram that an implantable pulse generator shown in FIGS. 3C and 3D and having a primary battery may utilize.

FIG. 24 shows an embodiment of a block diagram circuit 32 for the rechargeable implantable pulse generator 18 that takes into account the desirable technical features discussed above. FIG. 25 shows an embodiment of a block diagram circuit 33 for the implantable pulse generator 88 that also takes into account the desirable technical features discussed above.

Both the circuit 32 and the circuit 33 can be grouped into functional blocks, which generally correspond to the association and interconnection of the electronic components. FIGS. 24 and 25 show alternative embodiments of a block diagram that provides an overview of a representative desirable implantable pulse generator design. As can be seen, there may be re-use of the circuit 32, or alternatively, portions of the circuit 32 of the rechargeable implantable pulse generator 18, with minimal modifications, e.g., a predetermined selection of components may be included or may be exchanged for other components, and minimal changes to the system operating software (firmware). Re-use of a majority of the circuitry from the rechargeable implantable pulse generator 18 and much of the firmware allows for a low development cost for the rechargeable and primary cell implantable pulse generator.

In FIGS. 24 and 25, seven functional blocks are shown: (1) The Microprocessor or Microcontroller 36; (2) the Power Management Circuit 130; (3) the VCC Power Supply 132; (4) the VHH Power Supply 134; (5) the Stimulus Output Stage(s) 136; (6) the Output Multiplexer(s) 138; and (7) the Wireless Telemetry Circuit 140.

For each of these blocks, the associated functions, possible key components, and circuit description are now described.

a. The Microcontroller

The Microcontroller 36 is responsible for the following functions:

(1) The timing and sequencing of the stimulus output stage 136 and the VHH power supply 134 used by the stimulus output stage, (2) The sequencing and timing of power management functions, (3) The monitoring of the battery voltage, the stimulator voltages produced during the generation of stimulus pulses, and the total circuit current consumption, VHH, and VCC, (4) The timing, control, and interpretation of commands to and from the wireless telemetry circuit 140, (5) The logging (recording) of patient usage data as well as clinician programmed stimulus parameters and configuration data, and (6) The processing of commands (data) received from the user (patient) via the wireless link to modify the characteristics of the stimulus being delivered or to retrieve logged usage data.

The use of a microcontroller incorporating flash programmable memory allows the operating system software of the implantable pulse generator as well as the stimulus parameters and settings to be stored in non-volatile memory (data remains safely stored even if the battery 34 becomes fully discharged; or if the implantable pulse generator is placed in the Dormant mode). Yet, the data (operating system software, stimulus parameters, usage history log, etc.) can be erased and reprogrammed thousands of times during the life of the implantable pulse generator. The software (firmware) of the implantable pulse generator must be segmented to support the operation of the wireless telemetry routines while the flash memory of the microcontroller 36 is being erased and reprogrammed. Similarly, the VCC power supply 132 must support the power requirements of the microcontroller 36 during the flash memory erase and program operations.

Although the microcontroller 36 may be a single component, the firmware is developed as a number of separate modules that deal with specific needs and hardware peripherals. The functions and routines of these software modules are executed sequentially; but the execution of these modules are timed and coordinated so as to effectively function simultaneously. The microcontroller operations that are associated directly with a given hardware functional block are described with that block.

The Components of the Microcontroller Circuit may include:

(1) A single chip microcontroller 36. This component may be a member of the Texas Instruments MSP430 family of flash programmable, micro-power, highly integrated mixed signal microcontroller. Likely family members to be used include the MSP430F1610, MSP430F1611, MSP430F1612, MSP430F168, and the MSP430F169. Each of these parts has numerous internal peripherals, and a micropower internal organization that allows unused peripherals to be configured by minimal power dissipation, and an instruction set that supports bursts of operation separated by intervals of sleep where the microcontroller suspends most functions.

(2) A miniature, quartz crystal (X1) for establishing precise timing of the microcontroller. This may be a 32.768 KHz quartz crystal.

(3) Miscellaneous power decoupling and analog signal filtering capacitors.

b. Power Management Circuit

The Power Management Circuit 130 (including associated microcontroller actions) is responsible for the following functions:

(1) monitor the battery voltage, (2) suspend stimulation when the battery voltage becomes very low, and/or suspend all operation (go into the Dormant mode) when the battery voltage becomes critically low, (3) communicate (through the wireless telemetry link 112) with the external equipment the charge status of the battery 34, (4) prevent (with single fault tolerance) the delivery of excessive current from the battery 34, (5) provide battery power to the rest of the circuitry of the implantable pulse generator, e.g., VCC and VHH power supplies, (6) provide isolation of the Lithium Ion battery 34 from other circuitry while in the Dormant mode, (7) provide a hard microprocessor reset and force the implantable pulse generator 18 into the Dormant mode in the presence of long pacemaker magnet 118 application (or comparable device), (8) provide the microcontroller 36 with analog voltages with which to measure the magnitude of the battery voltage and the appropriate battery current flow (drain and charge), (9) recover power from the receive coil 42,

(10) control delivery of the receive coil power to recharge the Lithium Ion battery 34,

(11) monitor the battery voltage during charge and discharge conditions,

(12) communicate (through the wireless telemetry link 112) with the externally mounted or worn implant charger controller 102 to increase or decrease the strength of the RF magnetic field 100 for optimal charging of the battery 34,

(13) disable (with single fault tolerance) the delivery of charging current to the battery 34 in overcharge conditions, and

(14) provide the microcontroller 36 with analog voltages with which to measure the magnitude of the recovered power from the RF magnetic field 100.

The Components of the Power Management Circuit may include:

(1) Low on resistance, low threshold P channel MOSFETs with very low off state leakage current (Q2, Q3, and Q4).

(2) Analog switches (or an analog multiplexer) U3.

(3) Logic translation N-channel MOSFETs (Q5 & Q6) with very low off state leakage current.

(4) The receive coil 42 (see FIGS. 4B, 4C, and 4D), which desirably is a multi-turn, fine copper wire coil near the inside perimeter of the implantable pulse generator 18. Preferably, the receive coil includes a predetermined construction, e.g., 300 turns, each of four strands of #40 enameled magnetic wire, or the like. The maximizing of the coil's diameter and reduction of its effective RF resistance allows necessary power transfer at and beyond the typical implant depth of about one centimeter.

As can be seen in FIG. 4C, the receive coil 42 is generally rectangular in cross sectional shape, with a height H greater than its width W. In one embodiment, the height H is about five millimeters to about six millimeters, and the width W is about two millimeters to three millimeters.

The receive coil 42 also includes a maximum outside dimension X of about seventeen millimeters to about twenty millimeters, for example, as shown in FIG. 4D. The maximum outside dimension X may be measured from the midpoint on a straight line that bisects the coil into two equal parts. Although there may be more than one line that bisects the coil 42, the dimension X is to be the longest dimension X possible from the midpoint of the bisection line to the coil's outside edge.

(5) A micropower Lithium Ion battery charge management controller IC (integrated circuit); such as the MicroChip MCP73843-41, or the like.

c. The VCC Power Supply

The VCC Power Supply 132 is generally responsible for the following functions:

(1) Some of the time, the VCC power supply passes the battery voltage to the circuitry powered by VCC, such as the microcontroller 36, stimulus output stage 136, wireless telemetry circuitry 140, etc.

(2) At other times, the VCC power supply fractionally steps up the voltage to about 3.3V; (other useable voltages include 3.0V, 2.7V, etc.) despite changes in the Lithium Ion battery 34 voltage. This higher voltage is required for some operations such as programming or erasing the flash memory in the microcontroller 36, (e.g., in circuit programming).

The voltage converter/switch part at the center of the VCC power supply may be a charge pump DC to DC converter. Typical choices for this part may include the Maxim MAX1759, the Texas Instruments TPS60204, or the Texas Instruments REG710, among others. In the embodiment having a rechargeable battery 34, the VCC power supply may include a micropower, low drop out, linear voltage regulator; e.g., Microchip NCP1700T-3302, Maxim Semiconductor MAX1725, or Texas Instruments TPS79730.

The characteristics of the VCC Power Supply might include:

(1) high efficiency and low quiescent current, i.e., the current wasted by the power supply in its normal operation. This value should be less than a few microamperes; and (2) drop-out voltage, i.e., the minimal difference between the VBAT supplied to the VCC power supply and its output voltage. This voltage may be less than about 100 mV even at the current loads presented by the transmitter of the wireless telemetry circuitry 140.

(3) The VCC power supply 132 may allow in-circuit reprogramming of the implantable pulse generator firmware.

d. VHH Power Supply

Figure 32:
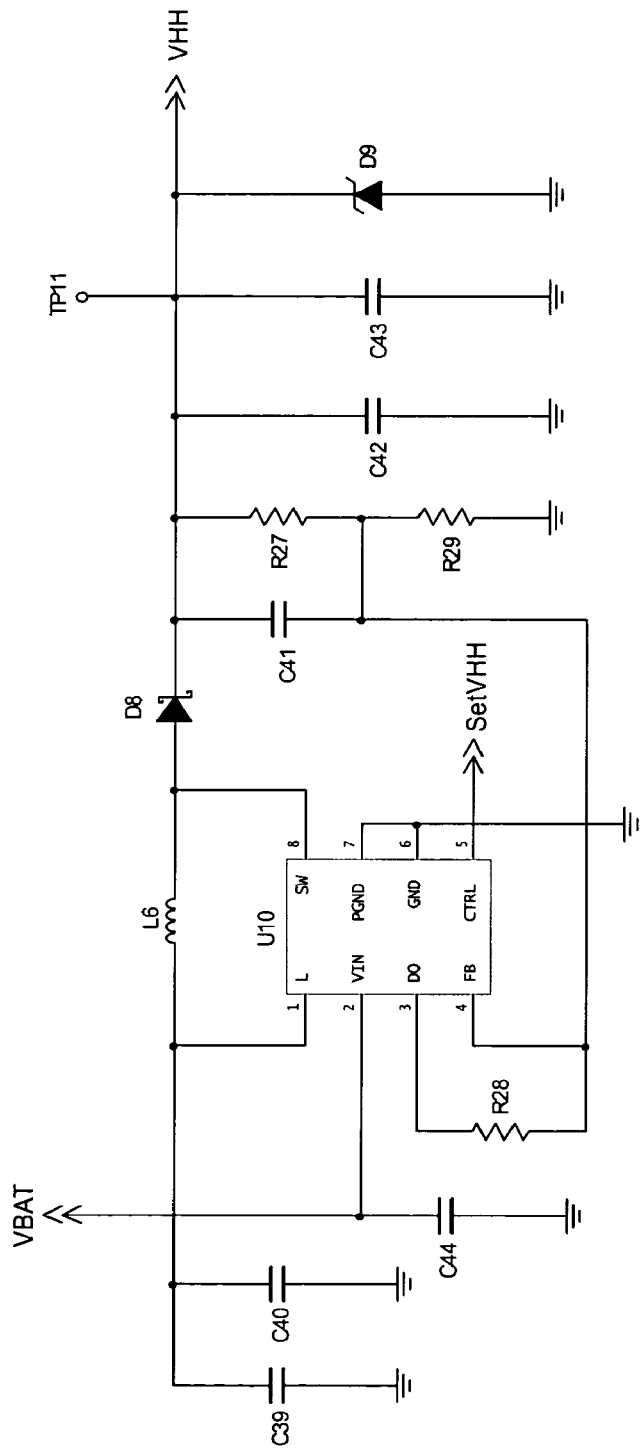
FIG. 32 is a circuit diagram showing a possible circuit for the VHH power supply feature used with the implantable pulse generator shown in FIGS. 3A through 3D.

A circuit diagram showing a desired configuration for the VHH power supply 134 is shown in FIG. 32. It is to be appreciated that modifications to this circuit diagram configuration which produce the same or similar functions as described are within the scope of the invention. The VHH power supply 134 is generally responsible for the following functions:

(1) Provide the Stimulus Output Stage 136 and the Output Multiplexer 138 with a programmable DC voltage between the battery voltage and a voltage high enough to drive the required cathodic phase current through the electrode circuit plus the voltage drops across the stimulator stage, the output multiplexer stage, and the output coupling capacitor. VHH is typically 12 VDC or less for neuromodulation applications; and 25V or less for muscle stimulation applications, although it may be higher for very long lead lengths.

The Components of the VHH Power Supply might include:

(1) Micropower, inductor based (fly-back topology) switch mode power supply (U10); e.g., Texas Instruments TPS61045, Texas Instruments TPS61041, or Linear Technology LT3464 with external voltage adjustment components.

(2) L6 is the flyback energy storage inductor.

(3) C42 & C43 form the output capacitor.

(4) R27, R28, and R29 establish the operating voltage range for VHH given the internal DAC which is programmed via the SETVHH logic command from the microcontroller 36.

(5) Diode D9 serves no purpose in normal operation and is added to offer protection from over-voltage in the event of a VHH circuit failure.

(6) The microcontroller 36 monitors VHH for detection of a VHH power supply failure, system failures, and optimizing VHH for the exhibited electrode circuit impedance.

e. Stimulus Output Stage

The Stimulus Output Stage(s) 136 is generally responsible for the following functions:

(1) Generate the identified biphasic stimulus current with programmable (dynamically adjustable during use) cathodic phase amplitude, pulse width, and frequency. The recovery phase may incorporate a maximum current limit; and there may be a delay time (most likely a fixed delay) between the cathodic phase and the recovery phase (see FIG. 28). Typical currents (cathodic phase) vary from about 0.5 mA to about 20 mA based on the electrode construction and the nature of the tissue being stimulated. Electrode circuit impedances can vary with the electrode and the application, but are likely to be less than 2,000 ohms and greater than 100 ohms across a range of electrode types.

The Components of the Stimulus Output Stage may include:

(1) The cathodic phase current through the electrode circuit is established by a high gain (HFE) NPN transistor (Q7) with emitter degeneration. In this configuration, the collector current of the transistor (Q7) is defined by the base drive voltage and the value of the emitter resistor (R24).

Two separate configurations are possible: In the first configuration (as shown in FIG. 27), the base drive voltage is provided by a DAC peripheral inside the microcontroller 36 and is switched on and off by a timer peripheral inside the microcontroller. This switching function is performed by an analog switch (U8). In this configuration, the emitter resistor (R24) is fixed in value and fixed to ground.

In a second alternative configuration, the base drive voltage is a fixed voltage pulse (e.g., a logic level pulse) and the emitter resistor is manipulated under microcontroller control. Typical options may include resistor(s) terminated by microcontroller IO port pins that are held or pulsed low, high, or floating; or an external MOSFET that pulls one or more resistors from the emitter to ground under program control. Note that the pulse timing need only be applied to the base drive logic; the timing of the emitter resistor manipulation is not critical.

The transistor (Q7) desirably is suitable for operation with VHH on the collector. The cathodic phase current through the electrode circuit is established by the voltage drop across the emitter resistor. Diode D7, if used, provides a degree of temperature compensation to this circuit.

(2) The microcontroller 36 (preferably including a programmable counter/timer peripheral) generates stimulus pulse timing to generate the cathodic and recovery phases and the interphase delay. The microcontroller 36 also monitors the cathode voltage to confirm the correct operation of the output coupling capacitor, to detect system failures, and to optimize VHH for the exhibited electrode circuit impedance; i.e., to measure the electrode circuit impedance. Additionally, the microcontroller 36 can also monitor the pulsing voltage on the emitter resistor; this allows the fine adjustment of low stimulus currents (cathodic phase amplitude) through changes to the DAC value.

f. The Output Multiplexer

The Output Multiplexer 138 is generally responsible for the following functions:

(1) Route the Anode and Cathode connections of the Stimulus Output Stage 136 to the appropriate electrode based on addressing data provided by the microcontroller 36.

(2) Allow recharge (recovery phase) current to flow from the output coupling capacitor C36 back through the electrode circuit with a programmable delay between the end of the cathodic phase and the beginning of the recovery phase (the interphase delay).

The circuit shown in FIG. 27 may be configured to provide monopolar stimulation (using the case 20 as the return electrode) to Electrode 1, to Electrode 2, or to both at the same time (sharing the current), or separately—perhaps with different stimulus parameters —through time multiplexing. This circuit could also be configured as a single bipolar output channel by changing the hardwire connection between the circuit board 32 and the electrode; i.e., by routing the case 20 connection to Electrode 1 or Electrode 2. The use of four or more channels per multiplexer stage (i.e., per output coupling capacitor) is possible.

The Components of the Output Multiplexer might include:

(1) An output coupling capacitor in series with the electrode circuit. This capacitor is desirably located such that there is no DC across the capacitor in steady state. This capacitor is typically charged by the current flow during the cathodic phase to a voltage range of about ¼th to ⅟10th of the voltage across the electrode circuit during the cathodic phase. Similarly, this capacitor is desirably located in the circuit such that the analog switches do not experience voltages beyond their ground of power supply (VHH).

(2) The analog switches (U7) must have a suitably high operating voltage, low ON resistance, and very low quiescent current consumption while being driven from the specified logic levels. Suitable analog switches include the Vishay/Siliconix DG412HS, for example.

(3) Microcontroller 36 selects the electrode connections to carry the stimulus current (and time the interphase delay) via address lines.

(4) Other, analog switches (U9) may be used to sample the voltage of VHH 134, the case 20, and the selected Electrode. The switched voltage, after the voltage divider formed by R25 and R26, is monitored by the microcontroller 36.

g. Wireless Telemetry Circuit

The Wireless Telemetry circuit 140 is responsible for the following functions:

(1) Provide reliable, bidirectional communications (half duplex) with an external controller—e.g., clinical programmer 108 or a implant charger controller 102, for example, via a VHF-UHF RF link (likely in the 402 MHZ to 405 MHz MICS band per FCC 47 CFR Part 95 and the Ultra Low Power—Active Medical Implant (AMI) regulations of the European Union). This circuit will look for RF commands at precisely timed intervals (e.g., twice a second), and this function must consume very little power. Much less frequently this circuit will transmit responses to commands sent by the external controller. This function should also be as low power as possible, but will represent a lower total energy demand than the receiver in most of the anticipated applications because wireless telemetry transmissions by the implantable pulse generator 18 will typically be rare events. The RF carrier is amplitude modulated (on-off keyed) with the digital data. Serial data is generated by the microcontroller 36 already formatted and timed. The wireless telemetry circuit 140 converts the serial data stream into a pulsing carrier signal during the transmit process; and it converts a varying RF signal strength into a serial data stream during the receive process (see FIG. 26B).

The Components of the Wireless Telemetry Circuit might include:

(1) a crystal controlled, micropower transceiver chip such as the AMI Semiconductor AMIS-52100 (U6). This chip is responsible for generating the RF carrier during transmissions and for amplifying, receiving, and detecting (converting to a logic level) the received RF signals. The transceiver chip must also be capable of quickly starting and stopping operation to minimize power consumption by keeping the chip disabled (and consuming very little power) the majority of the time; and powering up for only as long as required for the transmitting or receiving purpose. The transceiver chip may be enabled only when the stimulus output stage is not generating stimulus current.

(2) The transceiver chip has separate transmit and receive ports that must be switched to a single antenna/feedthru. This function is performed by the transmit/receive switch (U5) under microcontroller control via the logic line XMIT. The microcontroller 36 controls the operation of the transceiver chip via an I$^2$C (2-wire serial interface) serial communications link. The serial data to and from the transceiver chip may be handled by a UART or a SPI peripheral of the microcontroller. The message encoding/decoding and error detection may be performed by a separate, dedicated microcontroller; else this processing will be time shared with the other tasks of the only microcontroller.

The various inductor and capacitor components (U6) surrounding the transceiver chip and the transmit/receive switch (U5) are impedance matching components and harmonic filtering components, except as follows:

(1) X2, C33, and C34 are used to generate the crystal controlled reference frequency, desirably tuned to ⅟32 of the desired RF carrier frequency, (2) L4 and C27 form the tuned elements of a VCO (voltage controlled oscillator) operating at twice the carrier frequency, and (3) R20, C29, and C30 are filter components of the PLL (phase locked loop) filter used to generate the carrier (transmitter) or local oscillator (receiver) frequencies from the reference frequency.

B. Lead and Electrode

As previously described, the system 10 includes an implantable pulse generator 18, a lead 12, and an electrode 16. Two possible types of electrodes will be described below, although any number of electrode types may be used.

In one embodiment, the lead 12 and electrode 16 are sized and configured to be inserted into and to rest in tissue (see FIG. 2A), such as in the lower abdomen for example, without causing pain or discomfort or impact body image. Desirably, the lead 12 and electrode 16 can be inserted using a small (e.g., smaller than 16 gauge) introducer 158 (see FIG. 36) with minimal tissue trauma. The lead 12 and electrode 16 are formed from a biocompatible and electrochemically suitable material and possess no sharp features that can irritate tissue during extended use. Furthermore, the lead 12 and electrode 16 possess mechanical characteristics including mechanical compliance (flexibility) to flexibly respond to dynamic stretching, bending, and crushing forces that can be encountered within tissue in a wide variety of body regions without damage or breakage, and to accommodate relative movement of the pulse generator 18 coupled to the lead 12 without imposing force or torque to the electrode 16 which tends to dislodge the electrode.

Figure 33:
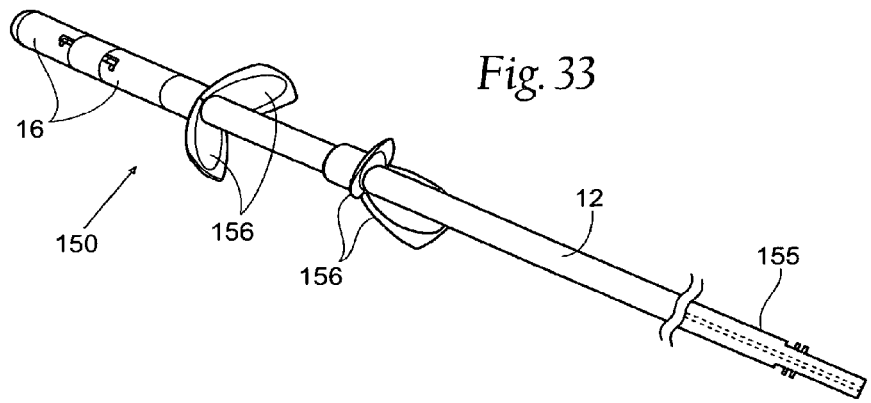
FIG. 33 is a perspective view of the lead and electrode associated with the system shown in FIGS. 1 and 2A.

Furthermore, the lead 12 and electrode 16 desirably include an anchoring means 150 for providing retention strength to resist migration within or extrusion from tissue in response to force conditions normally encountered during periods of extended use (see FIG. 33). In addition, the anchoring means 150 is desirably sized and configured to permit the electrode 16 position to be adjusted easily during insertion, allowing placement at the optimal location where selective stimulation may occur. The anchoring means 150 functions to hold the electrode at the implanted location despite the motion of the tissue and small forces transmitted by the lead 12 due to relative motion of the coupled implantable pulse generator 18 due to changes in body posture or external forces applied to the implant region. However, the anchoring means 150 should allow reliable release of the electrode 16 at higher force levels, to permit withdrawal of the implanted electrode 16 by purposeful pulling on the lead 12 at such higher force levels, without breaking or leaving fragments, should removal of the implanted electrode 16 be desired.

The lead 12 and electrode 16 is sized and configured to be anchored in soft adipose tissue, with no dependence on support or stability from muscle tissue. The lead 12 and electrode 16 are particularly well suited for placement in this soft adipose tissue because of the unique shape, size, spacing, and orientation of the anchoring means 150, which allows the lead 12 and electrode 16 to be used for other indications, such as in the field of urology (e.g., stimulation of nerves in adipose tissue for the treatment of incontinence and/or sexual restoration).

1. The Lead

Figure 34A:
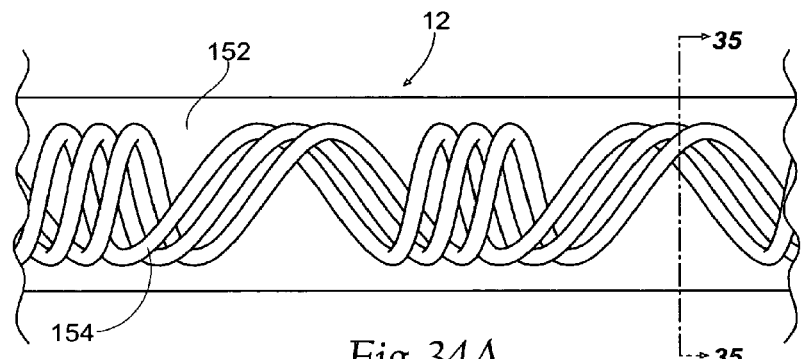
FIGS. 34A and 34B are side interior views of representative embodiments of a lead of the type shown in FIG. 33.

FIG. 33 shows a representative embodiment of a lead 12 and electrode 16 that provide the foregoing features. The implantable lead 12 comprises a molded or extruded component 152, which may encapsulate or enclose (in the case of a tubular construction) a coiled stranded wire element 154, and a plug or connector 155 (shown in FIG. 33). The lead 12 may be composed of one wire 154 connecting a single electrode 16 to contact(s) of the connector 155. Alternatively, the lead 12 may be composed of several individually insulated wires 154 connecting multiple electrodes 16 to multiple contacts of the connector 155. Each wire may be a single strand of metal, such as MP35N nickel-cobalt, or 316L stainless steel, or a more complex structure such as drawn tube of MP35N or 316L filled with silver. Alternatively, each separate insulated wire may be composed of multiple strands of wire (three such strands are shown in FIG. 34A), with each strand electrically connected in parallel at the electrode end and at the connector end. Examples of suitable electrical insulation include polyimide, parylene, and polyurethane. The molded or extruded lead 12 can have an outside diameter as small as about one (1) mm. The lead 12 may be approximately 10 cm to 40 cm in length, although lengths extending the length of the body are possible. The lead 12 provides electrical continuity between the connector 155 and the electrode 16.

Figure 34B:
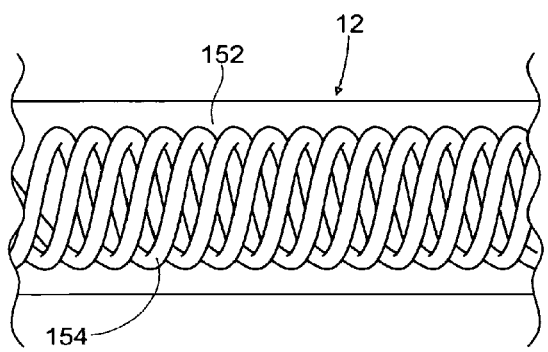
Figure 35:
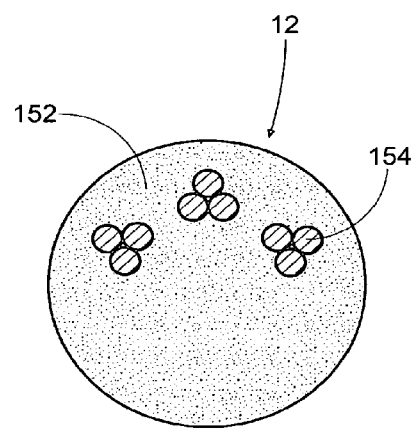
FIG. 35 is an end section view of the lead taken generally along line 35-35 in FIG. 34A.

The coil's pitch can be constant, as FIG. 34B shows, or the coil's pitch can alternate from high to low spacing to allow for flexibility in both compression and tension, as FIG. 34A shows. The tight pitch will allow for movement in tension, while the open pitch will allow for movement in compression.

A standard IS-1 or similar type connector 155 at the proximal end provides electrical continuity and mechanical attachment to the implantable pulse generator's connector jack 82. The lead 12 and connector 155 all may include provisions for a guidewire that passes through these components and the length of the lead 12 to the conductive electrode 16 at the distal end. Such a guidewire or stylet would allow the easy deployment of the lead 12 through an introducer.

2. The Electrode

The electrode 16 may comprise one or more electrically conductive surfaces. Two conductive surfaces are show in FIG. 33. The two conductive surfaces can be used either A) as two individual stimulating (cathodic) electrodes in monopolar configuration using the case 20 of the implantable pulse generator 18 as the return (anodic) electrode or B) in bipolar configuration with one electrode functioning as the stimulating (cathodic) electrode and the other as the return (anodic) electrode.

In general, bipolar stimulation is more spatially specific than monopolar stimulation—the area of stimulation is much smaller—which is good if the electrode 16 is close to a targeted tissue region, e.g., a nerve. But if the electrode 16 is farther from the target tissue region, then a monopolar configuration could be used because with the implantable pulse generator 18 acting as the return electrode, activation of the tissue is less sensitive to exact placement than with a bipolar configuration.

Often in use, a physician may first attempt to place the electrode 16 close to the target tissue region so that it could be used in a bipolar configuration, but if bipolar stimulation failed to activate the target tissue region, then the electrode 16 could be switched to a monopolar configuration. Two separate conductive surfaces on the electrode 16 provide an advantage because if one conductive surface fails to activate the target tissue region because it is too far from the target tissue region, then stimulation with the second conductive surface could be tried, which might be closer to the target tissue region. Without the second conductive surface, a physician would have to reposition the electrode to try to get closer to the target tissue region. This same concept may be extended to more than two conductive surfaces as well.

The electrode 16, or electrically conductive surface or surfaces, can be formed from PtIr (platinum-iridium) or, alternatively, 316L stainless steel or titanium, and possess a conductive surface of approximately 10 $mm^2$ to 20 $mm^2$. This surface area provides current densities up to 2 $mA/mm^2$ with per pulse charge densities less than 0.5 $\mu C/mm^2$. These dimensions and materials deliver a charge safely within the stimulation levels supplied by the implantable pulse generator.

Each conductive surface has an axial length in the range of about one millimeter to about five millimeters in length. When two or more conductive surfaces are used, either in the monopolar or bipolar configurations as described, there will be an axial spacing between the conductive surfaces in the range of about one millimeter to about ten millimeters separation.

3. The Anchoring Means

In the illustrated embodiment (see FIG. 33), the lead is anchored by anchoring means 150 specifically designed to secure the electrode 16 in a targeted tissue region, e.g., the layer of adipose tissue, without the support of muscle tissue. The anchoring means 150 takes the form of an array of shovel-like blades or scallops 156 proximal to the proximal-most electrode 16 (although a blade 156 or blades could also be proximal to the distal most electrode 16, or could also be distal to the distal most electrode 16). The blades 156 desirably present relatively large, generally planar surfaces, and are placed in multiple rows axially along the lead 12. The blades 156 may also be somewhat arcuate as well, or a combination of arcuate and planar surfaces. A row of blades 156 comprises two blades 156 spaced 180 degrees apart. The blades 156 may have an axial spacing between rows of blades in the range of six to fourteen millimeters, and each row may be spaced apart 90 degrees. The blades 156 are normally biased toward a radially outward condition into tissue. In this condition, the large surface area and orientation of the blades 156 allow the lead 12 to resist dislodgement or migration of the electrode 16 out of the correct location in the surrounding tissue. In the illustrated embodiment, the blades 156 are biased toward a proximal-pointing orientation, to better resist proximal migration of the electrode 16 with lead tension. The blades 156 are desirably made from a polymer material, e.g., high durometer silicone, polyurethane, or polypropylene, bonded to or molded with the lead 12.

The blades 156 can be deflected toward a distal direction in response to exerting a pulling force on the lead 12 at a threshold axial force level, which is greater than expected day-to-day axial forces. The blades 156 are sized and configured to yield during proximal passage through tissue in result to such forces, causing minimal tissue trauma, and without breaking or leaving fragments, despite the possible presence of some degree of tissue in-growth. This feature permits the withdrawal of the implanted electrode 16, if desired, by purposeful pulling on the lead 12 at the higher axial force level.

Desirably, the anchoring means 150 is prevented from fully engaging body tissue until after the electrode 16 has been deployed. The electrode 16 is not deployed until after it has been correctly located during the implantation (installation) process.

More particularly, and as described below, the lead 12 and electrode 16 are intended to be percutaneously introduced through a sleeve or introducer 158 shown in FIG. 36. As shown, the blades 156 assume a collapsed condition against the lead 12 body when within the sleeve 158. In this condition, the blades 156 are shielded from contact with tissue. Once the location is found, the sleeve 158 can be withdrawn, holding the lead 12 and electrode 16 stationary. Free of the sleeve 158, the blades 156 spring open to assume their radially deployed condition in tissue, fixing the electrode 16 in the desired location.

The position of the electrode 16 relative to the anchoring means 150, and the use of the sleeve 158, allows for both advancement and retraction of the electrode delivery sleeve 158 during implantation while simultaneously delivering test stimulation. During this phase of the implantation process, the distal tip of the lead 12 may be exposed to direct tissue contact, or alternatively, the lead 12 may be replaced by a metallic introducing needle that would extend beyond the end of the insulating delivery sleeve 158. The proximal end of the introducing needle (or the connector 155 of the lead 12) would be connected to a test stimulator. The sleeve 158 can be drawn back relative to the lead 12 to deploy the electrode 16 anchoring means 150, but only when the physician determines that the desired electrode location has been reached. The withdrawal of the sleeve 158 from the lead 12 causes the anchoring means 150 to deploy without changing the position of electrode 16 in the desired location (or allowing only a small and predictable, set motion of the electrode). Once the sleeve 158 is removed, the flexible, silicone-coated or polyurethane-coat lead 12 and electrode 16 are left implanted in the targeted tissue region.

4. Molded Nerve Cuff

In an alternative embodiment, a lead 12 and a cuff electrode 16' may be used. As FIG. 37 shows, the cuff electrode 16' includes at least one electrically conductive surface 160. It is to be appreciated that the cuff electrode 16' may be a spiral cuff, as shown, or may also be a split cylinder cuff. In the illustrated embodiment, there are three individually controllable electrically conductive surfaces 160, although more or less may be used. The surface 160 may be solid or the surface may be segmented into isolated conductive segments electrically coupled by a wire. It is to be appreciated that additional alternative configurations are possible as well. These surfaces may be manufactured using a thin film of metal deposited on a liquid crystal polymer substrate, or from strips of platinum, for example.

As FIG. 37 shows, the cuff electrode 16' comprises a body 162 and a strain relief boot 164 that may be molded from a low durometer elastomer material (e.g., silicone, such as a two part, translucent, pourable silicone elastomer, e.g., Nusil MED-4211). The electrically conductive surfaces 160 are integrated with the body 162 during the molding process. The boot 164 strengthens the junction, to resist the effect of torque forces that might be applied during implantation and use along the lead 12. In addition, the strain relief boot 164 helps to prevent tension and/or motion from damaging the lead to cuff interface for a longer flex life.

The molded body 162 of the cuff electrode 16' is shaped or formed during the molding process to normally assume a curled or tubular spiral or rolled configuration. As shown in FIG. 37, in its normal coiled condition, the body 162 extends in a spiral having a range of greater than 360 degrees from end to end, and in one embodiment about 540 degrees from end to end. The body 162 can be elastically uncoiled to increase its inner diameter, i.e., to be initially fitted about the periphery of a target nerve N, and in response to post-operative changes in the diameter of the target nerve N that might occur due to swelling. The elasticity of the body 162 wraps the electrically conductive surfaces gently against the periphery of the targeted nerve N. The elasticity of the body 162 is selected to gently wrap about the target nerve N without causing damage or trauma. To this end, it is believed desirable that the elastic memory of the cuff electrode 16' exhibits a predictable and repeatable pressure vs. diameter relationship that gradually increases pressure with increase in diameter to allow the electrode to fit snuggly about the periphery of a nerve, but not too tightly to cause damage (i.e., exerts a maximum pressure about the target nerve N that does not exceed about 20 mmHg).

II. Operating System

The implantable pulse generator operating system software 200 (operating on the microcontroller 36) controls the sequencing and operation of the implantable pulse generator hardware. As can be seen in FIG. 38, the operating system software 200 can be broadly grouped into two categories: the system software 202 and the application software 204.

A. System Software

The system software 202 constitutes a majority of the software code controlling the implantable pulse generator 18. As an example, the system software may constitute about 85 percent to 95 percent of the operating system software 200, and, the application software 204 may constitute about five percent to fifteen percent of the operating system software. Structurally, the system software 202 ranges from the low level peripheral drivers 206 that directly interface with the implantable pulse generator hardware to the higher level software drivers 208 that manages the timing of wireless telemetry communications 112 and the encoding and decoding of the wireless messages in accordance with the communications protocol.

The system software 202 is responsible for monitoring and controlling all the hardware of the implantable pulse generator 18. Key activities may include:

The activation and disabling of hardware components or sub-systems as they are required to be functional or are no longer required. For example, the wireless telemetry hardware is only enabled when it is required, as a power management technique. The stimulus power supply is only enabled immediately before and during the delivery of a stimulus pulse, as a power management and noise control technique.

The generation of precisely timed interrupts or software events. These software events are used to invoke the application software 204, update the current time data, and to schedule and perform regular or periodic "house cleaning" activities and the interface of system resources, such as, wireless telemetry communications, time and date information, storage and retrieval of usage data and operational settings, and monitoring battery voltage, etc.

Configure the wireless telemetry circuitry to "sniff" for any communications or interference on the wireless telemetry 112.

Configure the wireless telemetry circuitry 140 to receive a command and to send a response.

Process any general (not application specific) commands and generate the associated response (this includes the retrieval of log data).

Generate a stimulus pulse of specified amplitude and pulse duration.

Measure the cathodic phase voltage during a stimulus pulse and optimize the value of VHH as appropriate.

Direct a stimulus pulse to the desired channel(s).

Monitor the battery voltage and shut down operations as necessary in low battery and critical low battery conditions.

Monitor the magnitude of the voltage recovered from the power management (charging) circuitry 130 and the battery voltage to provide correct information to the implant charger controller 102 (through the wireless telemetry link 112) and to control the charging process.

Measure the value of the VHH power supply and take corrective actions if necessary.

The system software 204 is also responsible for performing the basic functions that are required by all, or most, applications. These functions may include:

Invocation of and interface to the application software (code) 204.

Making implantable pulse generator and system status information available to the application software; and similarly, the system software accepts data generated by the application software and performs the actions associated with that data (e.g., store information into non-volatile memory, generate a stimulus pulse of specified parameters, modify the delay time until the next stimulus pulse, change status data for subsequent communications with external hardware, etc.).

The execution of the application software on a time or event scheduled basis (e.g., to be executed every ⅟₃₀th second or whenever a command is received via the wireless telemetry 112).

Decode and authenticate (i.e., check for accuracy and legitimacy) commands received by the wireless telemetry 112.

Pass along to the application software any valid, application specific command received.

Encode and transmit any responses made by the application software

Update log entries based on changes to operating modes, charging, etc.

Update log entries in response to data passed by the application software 204 to the system software 202.

B. Application Software

The application software 204 is implemented as a separate module(s) that interfaces with the implantable pulse generator resources (hardware) through calls to software units in the system software 202. This allows the application software 204 to be written in relative isolation from the details of the implantable pulse generator hardware and the details of how the system software 202 manages the hardware. Thus the application software 204 utilizes a clearly defined (and limited) interface 203 to the system software 204 and implantable pulse generator resources (hardware and software) through the use of calls to system software units (functions).

The application software 204 is responsible for performing the activities that are specific to the particular application for which the implantable pulse generator is being used. These functions may include:

Determining what actions the implantable pulse generator 18 will take to implement the desired clinical, therapeutic, diagnostic, or other physiological process for which the implantable pulse generator was implanted.

Defining application status information that will be communicated to external hardware via the wireless telemetry 112.

Determining what usage, history, or diagnostic information should be stored or retrieved for use by the application or for telemetry to the external hardware.

Establish the stimulus frequency desired. This decision may make use of the current time information provided by the system software 202.

Establish the amplitude and pulse duration of the next stimulus pulse to be generated. This decision may also make use of the current time information provided by the system software.

Interpretation of application specific commands received from the system software 202 and generation of the response to the application specific commands to the system software.

Update entries to any application specific logs.

III. Representative Indications

Due to their technical features, the implantable pulse generator 18 and 88 can be used to provide beneficial results in diverse therapeutic and functional restorations indications.

For example, in the field of urology, possible indications for use of the implantable pulse generators 18 and 68 include the treatment of (i) urinary and fecal incontinence; (ii) micturition/retention; (iii) restoration of sexual function; (iv) defecation/constipation; (v) pelvic floor muscle activity; and/or (vi) pelvic pain.

The implantable pulse generators 18 and 88 can be used for deep brain stimulation in the treatment of (i) Parkinson's disease; (ii) multiple sclerosis; (iii) essential tremor; (iv) depression; (v) eating disorders; (vi) epilepsy; and/or (vii) minimally conscious state.

The implantable pulse generators 18 and 88 can be used for pain management by interfering with or blocking pain signals from reaching the brain, in the treatment of, e.g., (i) peripheral neuropathy; and/or (ii) cancer.

The implantable pulse generators 18 and 88 can be used for vagal nerve stimulation for control of epilepsy, depression, or other mood/psychiatric disorders.

The implantable pulse generators 18 and 88 can be used for the treatment of obstructive sleep apnea.

The implantable pulse generators 18 and 88 can be used for gastric stimulation to prevent reflux or to reduce appetite or food consumption.

The implantable pulse generators 18 and 88 can be used to compensate for various cardiac dysfunctions, such as rhythm disorders.

The implantable pulse generators 18 and 88 can be used in functional restorations indications such as the restoration of motor control, to restore (i) impaired gait after stroke or spinal cord injury (SCI); (ii) impaired hand and arm function after stroke or SCI; (iii) respiratory disorders; (iv) swallowing disorders; (v) sleep apnea; and/or (vi) neurotherapeutics, allowing individuals with neurological deficits, such as stroke survivors or those with multiple sclerosis, to recover functionally.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method comprising:
    transcutaneously recharging a rechargeable battery within a housing of an implantable electrical stimulation generator via an externally generated radio frequency magnetic field, wherein the radio frequency magnetic field is generated via a first circuitry of an external controller and a charging coil coupled to the first circuitry, wherein the externally generated radio frequency magnetic field is received via a power receiving coil carried within the housing of the implantable electrical stimulation generator to recharge the rechargeable battery;
    wirelessly communicating with an antenna and second circuitry of the implantable electrical stimulation generator via the first circuitry of the external controller using at least one of UHF signals or VHF signals, wherein transcutaneously recharging the rechargeable battery comprises transcutaneously recharging the rechargeable battery during a battery recharge period, wherein wirelessly communicating comprises wirelessly receiving, during the battery recharge period, status information from the implantable electrical stimulator to allow the external controller to automatically adjust the magnitude of the radio frequency magnetic field; and
    automatically adjusting a magnitude of the radio frequency magnetic field based on the received status information.

2. The method of claim 1, further comprising instructing a user to reposition the charging coil based on the status information.

3. The method of claim 1, wherein automatically adjusting the magnitude of the radio frequency magnetic field comprises automatically adjusting the magnitude of the radio frequency magnetic field up to about 300 percent of an initial magnitude.

4. The method of claim 1, wherein the status information includes an indication of a battery charge status and an indication of a magnitude of power recovered by the power receiving coil.

5. The method of claim 1, wherein the status information includes a magnitude of a voltage of the battery.

6. The method of claim 1, wherein the radio frequency magnetic field comprises a frequency between about 30 KHz and about 300 KHz.

7. The method of claim 1, wherein wirelessly communicating with the antenna and the first circuitry of the implantable electrical stimulation generator via the second circuitry of the external controller using at least one of the UHF signals or the VHF signals comprises wirelessly communicating with the antenna and the first circuitry of the implantable electrical stimulation generator via the second circuitry of the external controller using signals in the Medical Implant Communications Service (MICS) band between about 402 MHz and about 405 MHz.

8. The method of claim 1, wherein wirelessly communicating comprises wirelessly receiving, from the implantable electrical stimulation generator, instructions to increase or decrease a strength of the magnetic field during the recharging of the battery, while at the same time, generating the radio frequency magnetic field to recharge the rechargeable battery.

9. The method of claim 1, wherein the antenna is carried within the housing of the implantable electrical stimulation generator.

10. The method of claim 1, wherein an outside diameter of the charging coil is between about 40 millimeters and about 70 millimeters, and a thickness of the charging coil as measured perpendicular to the diameter of the charging coil is between about three millimeters and about eleven millimeters.

11. The method of claim 1, wherein automatically adjusting the magnitude of the radio frequency magnetic field based on the received status information comprises automatically increasing the magnitude of the radio frequency magnetic field based on the received status information.

* * * * *